US011123415B2

(12) United States Patent
Gourapura et al.

(10) Patent No.: US 11,123,415 B2
(45) Date of Patent: Sep. 21, 2021

(54) **NANOPARTICLE COMPOSITIONS FOR *SALMONELLA* VACCINES**

(71) Applicant: Ohio State Innovation Foundation, Columbus, OH (US)

(72) Inventors: Renukaradhya Gourapura, Wooster, OH (US); Ramesh Selvaraj, Wooster, OH (US); Sankar Renu, Wooster, OH (US)

(73) Assignee: Ohio State Innovation Foundation, Columbus, OH (US)

( * ) Notice: Subject to any disclaimer, the term of this patent is extended or adjusted under 35 U.S.C. 154(b) by 0 days.

(21) Appl. No.: 16/639,311

(22) PCT Filed: Aug. 16, 2018

(86) PCT No.: PCT/US2018/000238
§ 371 (c)(1),
(2) Date: Feb. 14, 2020

(87) PCT Pub. No.: WO2019/035963
PCT Pub. Date: Feb. 21, 2019

(65) Prior Publication Data
US 2021/0093705 A1 Apr. 1, 2021

Related U.S. Application Data

(60) Provisional application No. 62/546,164, filed on Aug. 16, 2017.

(51) Int. Cl.
*A61K 39/112* (2006.01)
*A61K 39/116* (2006.01)
*A61K 9/51* (2006.01)
*A61K 39/00* (2006.01)

(52) U.S. Cl.
CPC ........ *A61K 39/0275* (2013.01); *A61K 9/5161* (2013.01); *A61K 39/116* (2013.01); *A61K 2039/542* (2013.01); *A61K 2039/55555* (2013.01)

(58) Field of Classification Search
None
See application file for complete search history.

(56) References Cited

U.S. PATENT DOCUMENTS

| | | |
|---|---|---|
| 4,436,727 A | 3/1984 | Ribi |
| 4,866,034 A | 9/1989 | Ribi |
| 4,877,611 A | 10/1989 | Cantrell |
| 4,912,094 A | 3/1990 | Myers et al. |
| 5,856,462 A | 1/1999 | Agrawal |
| 6,303,347 B1 | 10/2001 | Johnson et al. |
| 6,355,257 B1 | 3/2002 | Johnson et al. |
| 2009/0297561 A1 | 12/2009 | Pasternack et al. |
| 2011/0206717 A1 | 8/2011 | Cunningham |
| 2011/0293723 A1 | 12/2011 | Bratzler et al. |
| 2015/0231232 A1* | 8/2015 | Grandi .................... A61P 31/10 424/244.1 |
| 2017/0080078 A1 | 3/2017 | Gourapura et al. |

FOREIGN PATENT DOCUMENTS

| | | |
|---|---|---|
| IN | 2015/DEL/4150 A | 1/2018 |
| WO | 94/00153 | 1/1994 |
| WO | 95/17210 | 6/1995 |
| WO | 96/02555 | 2/1996 |
| WO | 96/33739 | 10/1996 |
| WO | 99/33488 | 7/1999 |
| WO | 99/52549 | 10/1999 |
| WO | 00/09159 | 2/2000 |
| WO | 2011/150249 A1 | 12/2011 |
| WO | 2013/084070 A2 | 6/2013 |

OTHER PUBLICATIONS

Gao et al. In: Infectious Microbes & Diseases, vol. 2, pp. 3-9, Mar. 2020.*
Agueros M, Areses P, Campanero MA, Salman H, Quincoces G, Penuelas I, et al. Bioadhesive properties and biodistribution of cyclodextrin-poly(anhydride) nanoparticles. Eur J Pharm Sci. 2009;37:231-40.
Annamalai T, Pina-Mimbela R, Kumar A, Binjawadagi B, Liu Z, Renukaradhya GJ, et al. Evaluation of nanoparticle-encapsulated outer membrane proteins for the control of Campylobacter jejuni colonization in chickens. Poult Sci. 2013;92:2201-11.
Arbos P, Campanero MA, Arangoa MA, Renedo MJ, Irache JM. Influence of the surface characteristics of PVM/MA nanoparticles on their bioadhesive properties. J Control Release. 2003;89:19-30.
Astete CE, Sabliov CM. Synthesis and characterization of PLGA nanoparticles. J Biomater Sci Polym Ed. 2006,17:247-89.
Azizi A, Kumar A, Diaz-Mitoma F, Mestecky J. Enhancing oral vaccine potency by targeting intestinal M cells. PLoS Pathog. 2010;6:e1001147.
Barrow PA. *Salmonella* infections: immune and non-immune protection with vaccines. Avian Pathol. 2007;36:1-13.
Berthelot-Herault F, Mompart F, Zygmunt MS, Dubray G, Duchet-Suchaux M. Antibody responses in the serum and gut of chicken lines differing in cecal carriage of *Salmonella enteritidis*. Vet Immunol Immunopathol. 2003;96:43-52.
Binjawadagi B, Dwivedi V, Manickam C, Ouyang K, Torrelles JB, Renukaradhya GJ. An innovative approach to induce cross-protective immunity against porcine reproductive and respiratory syndrome virus in the lungs of pigs through adjuvanted nanotechnology-based vaccination. Int J Nanomedicine. 2014;9:1519-35.
Binjawadagi B, Dwivedi V, Manickam C, Ouyang K, Wu Y, Lee LJ, et al. Adjuvanted poly(lactic-co-glycolic) acid nanoparticle-entrapped inactivated porcine reproductive and respiratory syndrome virus vaccine elicits cross-protective immune response in pigs. Int J Nanomedicine. 2014;9:679-94.
Bowman K, Leong KW. Chitosan nanoparticles for oral drug and gene delivery. Int J Nanomedicine. 2006;1:117-28.
Burkholder KM, Thompson KL, Einstein ME, Applegate TJ, Patterson JA. Influence of stressors on normal intestinal microbiota, intestinal morphology, and susceptibility to *Salmonella enteritidis* colonization in broilers. Poult Sci. 2008;87:1734-41.

(Continued)

*Primary Examiner* — Sarvamangala Devi
(74) *Attorney, Agent, or Firm* — Meunier Carlin & Curfman LLC

(57) ABSTRACT

The present disclosure relates to nanoparticle compositions for use as vaccines against *Salmonella*.

14 Claims, 26 Drawing Sheets

(56) References Cited

OTHER PUBLICATIONS

Camacho AI, Da Costa Martins R, Tamayo I, de Souza J, Lasarte JJ, Mansilla C, et al. Poly(methyl vinyl ether-co-maleic anhydride) nanoparticles as innate immune system activators. Vaccine. 2011;29:7130-5.

Cerchiara T, Luppi B, Chidichimo G, Bigucci F, Zecchi V. Chitosan and poly(methyl vinyl ether-co-maleic anhydride) microparticles as nasal sustained delivery systems. Eur J Pharm Biopharm. 2005;61:195-200.

Dhakal S, Goodman J, Bondra K, Lakshmanappa YS, Hiremath J, Shyu DL, et al. Polyanhydride nanovaccine against swine influenza virus in pigs. Vaccine. 2017;35:1124-31.

Dhakal S, Hiremath J, Bondra K, Lakshmanappa YS, Shyu DL, Ouyang K, et al. Biodegradable nanoparticle delivery of inactivated swine influenza virus vaccine provides heterologous cell-mediated immune response in pigs. J Control Release. 2017;247:194-205.

Dodane V, Amin Khan M, Merwin JR. Effect of chitosan on epithelial permeability and structure. Int J Pharm. 1999;182:21-32.

Dubey S, Avadhani K, Mutalik S, Sivadasan SM, Maiti B, Girisha SK, et al. Edwardsiella tarda OmpA Encapsulated in Chitosan Nanoparticles Shows Superior Protection over Inactivated Whole Cell Vaccine in Orally Vaccinated Fringed-Lipped Peninsula Carp (*Labeo fimbriatus*). Vaccines (Basel). 2016;4.

Fabrega A, Vila J. *Salmonella enterica* serovar Typhimurium skills to succeed in the host: virulence and regulation. Clin Microbiol Rev. 2013;26:308-41.

Ferreira AJ, Ferreira CS, Knobl T, Moreno AM, Bacarro MR, Chen M, et al. Comparison of three commercial competitive-exclusion products for controlling *Salmonella* colonization of broilers in Brazil. J Food Prot. 2003;66:490-2.

Gao P, Xia G, Bao Z, Feng C, Cheng X, Kong M, et al. Chitosan based nanoparticles as protein carriers for efficient oral antigen delivery. Int J Biol Macromol. 2016;91:716-23.

Garland MJ, Singh TR, Woolfson AD, Donnelly RF. Electrically enhanced solute permeation across poly(ethylene glycol)-crosslinked poly(methyl vinyl ether-co-maleic acid) hydrogels: effect of hydrogel crosslink density and ionic conductivity. Int J Pharm. 2011;406:91-8.

George, Anna, et al. "Route-Related Variation in the Immunogenicity of Killed *Salmonella enteritidis* Vaccine: Role of Antigen Presenting Cells." Microbiology and immunology 33.6 (1989): 479-488.

Greig JD, Ravel A. Analysis of foodborne outbreak data reported internationally for source attribution. Int J Food Microbiol. 2009;130:77-87.

Gutjahr A, Phelip C, Coolen AL, Monge C, Boisgard AS, Paul S, et al. Biodegradable Polymeric Nanoparticles-Based Vaccine Adjuvants for Lymph Nodes Targeting. Vaccines (Basel). 2016;4.

Hamid N, Jain SK. Characterization of an outer membrane protein of *Salmonella enterica* serovar typhimurium that confers protection against typhoid. Clin Vaccine Immunol. 2008;15:1461-71.

Humphrey T, Jorgensen F. Pathogens on meat and infection in animals—Establishing a relationship using campylobacter and *Salmonella* as examples. Meat science. 2006;74:89-97.

Huntimer L, Ramer-Tait AE, Petersen LK, Ross KA, Walz KA, Wang C, et al. Evaluation of biocompatibility and administration site reactogenicity of polyanhydride-particle-based platform for vaccine delivery. Advanced healthcare materials. 2013;2:369-78.

Ilium L. Nanoparticulate systems for nasal delivery of drugs: a real improvement over simple systems? J Pharm Sci. 2007;96:473-83.

Kamble NM, Lee JH. Homologous prime-boost immunization with live attenuated *Salmonella enterica* serovar Senftenberg and its preventive efficacy against experimental challenge with various strains of S. Senftenberg. BMC Vet Res. 2017;13:39.
Khan MI, Fadl AA, Venkitanarayanan KS. Reducing colonization of *Salmonella enteritidis* in chicken by targeting outer membrane proteins. J Appl Microbiol. 2003;95:142-5.
Kim SY, Doh HJ, Jang MH, Ha YJ, Chung SI, Park HJ. Oral immunization with Helicobacter pylori-loaded poly(D, L-lactide-co-glycolide) nanoparticles. Helicobacter. 1999;4:33-9.
Komoriya K, Shibano N, Higano T, Azuma N, Yamaguchi S, Aizawa SI. Flagellar proteins and type III-exported virulence factors are the predominant proteins. secreted into the culture media of *Salmonella typhimurium*. Mol Microbiol. 1999;34:767-79.
Koppolu B, Zaharoff DA. The effect of antigen encapsulation in chitosan particles on uptake, activation and presentation by antigen presenting cells. Biomaterials. 2013;34:2359-69.
Lee JS, Jung ID, Lee CM, Park JW, Chun SH, Jeong SK, et al. Outer membrane protein a of *Salmonella enterica* serovar Typhimurium activates dendritic cells and enhances Th1 polarization. BMC Microbiol. 2010;10:263.
Lee SK, Chon JW, Song KY, Hyeon JY, Moon JS, Seo KH. Prevalence, characterization, and antimicrobial susceptibility of *Salmonella gallinarum* isolated from eggs produced in conventional or organic farms in South Korea. Poult Sci. 2013;92:2789-97.
Lee YJ, Mo IP, Kang MS. Protective efficacy of live *Salmonella gallinarum* 9R vaccine in commercial layer flocks. Avian Pathol. 2007;36:495-8.
Liu L, Yao W, Rao Y, Lu X, Gao J. pH-Responsive carriers for oral drug delivery: challenges and opportunities of current platforms. Drug Deliv. 2017;24:569-81.
Liu, Qiong, et al. Outer membrane vesicles derived from *Salmonella enteritidis* protect against the virulent wild-type strain infection in a mouse model. J Microbiol Biotechnol 27.8 (2017): 1519-28.
Majowicz SE, Musto J, Scallan E, Angulo FJ, Kirk M, O'Brien SJ, et al. The global burden of nontyphoidal *Salmonella gastroenteritis*. Clin Infect Dis. 2010;50:882-9.
McSorley, Stephen J., et al. "Bacterial flagellin is an effective adjuvant for CD4+ T cells in vivo." The Journal of Immunology 169.7 (2002): 3914-3919.
Meenakshi M, Bakshi CS, Butchaiah G, Bansal MP, Siddiqui MZ, Singh VP. Adjuvanted outer membrane protein vaccine protects poultry against infection with *Salmonella enteritidis*. Vet Res Commun. 1999;23:81-90.
Miller H, Zhang J, Kuolee R, Patel GB, Chen W. Intestinal M cells: the fallible sentinels? World J Gastroenterol. 2007;13:1477-86.
Morachis JM, Mahmoud EA, Almutairi A. Physical and chemical strategies for therapeutic delivery by using polymeric nanoparticles. Pharmacol Rev. 2012;64:505-19.
Nagarajan AG, Balasundaram SV, Janice J, Karnam G, Eswarappa SM, Chakravortty D. SopB of *Salmonella enterica* serovar Typhimurium is a potential DNA vaccine candidate in conjugation with live attenuated bacteria. Vaccine. 2009;27:2804-11.
Ochoa J, Irache JM, Tamayo I, Walz A, DelVecchio VG, Gamazo C. Protective immunity of biodegradable nanoparticle-based vaccine against an experimental challenge with *Salmonella enteritidis* in mice. Vaccine. 2007;25:4410-9.
Okamura M, Lillehoj HS, Raybourne RB, Babu U, Heckert R. Antigen-specific lymphocyte proliferation and interleukin production in chickens immunized with killed *Salmonella enteritidis* vaccine or experimental subunit vaccines. Avian Dis. 2003;47:1331-8.
Okamura M, Tachizaki H, Kubo T, Kikuchi S, Suzuki A, Takehara K, et al. Comparative evaluation of a bivalent killed *Salmonella vaccine* to prevent egg contamination with *Salmonella enterica* serovars Enteritidis, Typhimurium, and Gallinarum biovar Pullorum, using 4 different challenge models. Vaccine. 2007;25:4837-44.
Panel ES. Opinion of the Scientific Panel on Biological Hazards on a request from the Commission related to the use of vaccines for the control of *Salmonella* in poultry. The EFSA Journal. 2004;114:1-74.
Piskin E. Biodegradable polymers as biomaterials. J Biomater Sci Polym Ed. 1995;6:775-95.
Pore D, Mahata N, Pal A, Chakrabarti MK. Outer membrane protein A (OmpA) of Shigella flexneri 2a, induces protective immune response in a mouse model. PLoS One. 2011;6:e22663.
Prejit, Agarwal RK, Porteen K, Dubal ZB, Asha K, Shweta S, et al. Evaluation of recombinant outer membrane protein based vaccine against *Salmonella typhimurium* in birds. Biologicals : journal of the International Association of Biological Standardization. 2013;41:162-8.
Quan S, Hiniker A, Collet JF, Bardwell JC. Isolation of bacteria envelope proteins. Methods Mol Biol. 2013;966:359-66.

(56) References Cited

OTHER PUBLICATIONS

Reboucas Jde S, Irache JM, Camacho AI, Esparza I, Del Pozo V, Sanz ML, et al. Development of poly(anhydride) nanoparticles loaded with peanut proteins: the influence of preparation method on the immunogenic properties. Eur J Pharm Biopharm. 2012;82:241-9.
Reddy ST, van der Vlies AJ, Simeoni E, Angeli V, Randolph GJ, O'Neil CP, et al. Exploiting lymphatic transport and complement activation in nanoparticle vaccines. Nat Biotechnol. 2007;25:1159-64.
Renukaradhya GJ, Narasimhan B, Mallapragada SK. Respiratory nanoparticle-based vaccines and challenges associated with animal models and translation. J Control Release. 2015;219:622-31.
Ricke, Steven C., Anita Khatiwara, and Young Min Kwon. Application of microarray analysis of foodborne Salmonella in poultry production: a review. Poultry science 92.9 (2013): 2243-2250.
Salman HH, Gamazo C, Campanero MA, Irache JM. Salmonella-like bioadhesive nanoparticles. J Control Release. 2005;106:1-13.
Salman HH, Irache JM, Gamazo C. Immunoadjuvant capacity of flagellin and mannosamine-coated poly(anhydride) nanoparticles in oral vaccination. Vaccine. 2009;27:4784-90.
Samal SK, Dash M, Van Vlierberghe S, Kaplan DL, Chiellini E, van Blitterswijk C, et al. Cationic polymers and their therapeutic potential. Chem Soc Rev. 2012;41:7147-94.
Sankar R, Karthik S, Subramanian N, Krishnaswami V, Sonnemann J, Ravikumar V. Nanostructured delivery system for Suberoylanilide hydroxamic acid against lung cancer cells. Materials science & engineering C, Materials for biological applications. 2015;51:362-8.
Sankar R, Ravikumar V. Biocompatibility and biodistribution of suberoylanilide hydroxamic acid loaded poly (DL-lactide-co-glycolide) nanoparticles for targeted drug delivery in cancer. Biomed Pharmacother. 2014;68:865-71.
Sato, Yukio, et al. "Immunostimulatory DNA sequences necessary for effective intradermal gene immunization." Science 273.5273 (1996): 352-354.
Satzer P, Svec F, Sekot G, Jungbauer A. Protein adsorption onto nanoparticles induces conformational changes: Particle size dependency, kinetics, and mechanisms. Engineering in life sciences. 2016;16:238-46.
Scallan E, Hoekstra RM, Angulo FJ, Tauxe RV, Widdowson MA, Roy SL, et al. Foodborne illness acquired in the United States—major pathogens. Emerg Infect Dis. 2011;17:7-15.
Schipper NG, Varum KM, Artursson P. Chitosans as absorption enhancers for poorly absorbable drugs. 1: Influence of molecular weight and degree of acetylation on drug transport across human intestinal epithelial (Caco-2) cells. Pharm Res. 1996;13:1686-92.
Shanmugasundaram R, Kogut MH, Arsenault RJ, Swaggerty CL, Cole K, Reddish JM, et al. Effect of Salmonella infection on cecal tonsil regulatory T cell properties in chickens. Poult Sci. 2015;94:1828-35.
Sheela RR, Babu U, Mu J, Elankumaran S, Bautista DA, Raybourne RB, et al. Immune responses against Salmonella enterica serovar enteritidis infection in virally immunosuppressed chickens. Clin Diagn Lab Immunol. 2003;10:670-9.
Singh B, Maharjan S, Jiang T, Kang SK, Choi YJ, Cho CS. Combinatorial Approach of Antigen Delivery Using M Cell-Homing Peptide and Mucoadhesive Vehicle to Enhance the Efficacy of Oral Vaccine. Mol Pharm. 2015;12:3816-28.
Slutter B, Plapied L, Fievez V, Sande MA, des Rieux A, Schneider YJ, et al. Mechanistic study of the adjuvant effect of biodegradable nanoparticles in mucosal vaccination. J Control Release. 2009;138:113-21.
Sood S, Rishi P, Vohra H, Sharma S, Ganguly NK. Cellular immune response induced by Salmonella enterica serotype Typhi iron-regulated outer-membrane proteins at peripheral and mucosal levels. J Med Microbiol. 2005;54:815-21.
Tennant SM, Levine MM. Live attenuated vaccines for invasive Salmonella infections. Vaccine. 2015;33 Suppl 3:C36-41.
Tran TQ, Quessy S, Letellier A, Desrosiers A, Boulianne M. Immune response following vaccination against Salmonella enteritidis using 2 commercial bacterins in laying hens. Can J Vet Res. 2010;74:185-92.
Ulery BD, Nair LS, Laurencin CT. Biomedical Applications of Biodegradable Polymers. Journal of polymer science Part B, Polymer physics. 2011;49:832-64.
Van der Lubben IM, Verhoef JC, Borchard G, Junginger HE. Chitosan for mucosal vaccination. Adv Drug Deliv Rev. 2001;52:139-44.
Van Ginkel FW, Nguyen HH, McGhee JR. Vaccines for mucosal immunity to combat emerging infectious diseases. Emerg Infect Dis. 2000;6:123-32.
Varmuzova K, Faldynova M, Elsheimer-Matulova M, Sebkova A, Polansky O. Havlickova H, et al. Immune protection of chickens conferred by a vaccine consisting of attenuated strains of Salmonella enteritidis, Typhimurium and Infantis. Vet Res. 2016;47:94.
Vasserman Y, Pitcovski J. Genetic detoxification and adjuvant-activity retention of Escherichia coli enterotoxin LT. Avian Pathol. 2006;35:134-40.
Wang JJ, Zeng ZW, Xiao RZ, Xie T, Zhou GL, Zhan XR, et al. Recent advances of chitosan nanoparticles as drug carriers. Int J Nanomedicine. 2011;6:765-74.
Wolfenden RE, Layton SL, Wolfenden AD, Khatiwara A, Gaona-Ramirez G, Pumford NR, et al. Development and evaluation of candidate recombinant Salmonella-vectored Salmonella vaccines. Poult Sci. 2010;89:2370-9.
Zhang F, Hao C, Zhang S, Li A, Zhang Q, Wu W, et al. Oral immunization with recombinant enterovirus 71 VP1 formulated with chitosan protects mice against. lethal challenge. Virol J. 2014;11:80.
Zhao K, Chen G, Shi XM, Gao TT, Li W, Zhao Y, et al. Preparation and efficacy of a live newcastle disease virus vaccine encapsulated in chitosan nanoparticles. PLoS One. 2012;7:e53314.
International Preliminary Report on Patentability issued for Application No. PCT/US2018/000238, dated Feb. 27, 2020.
International Search Report and Written Opinion issued by the International Searching Authority (ISA/US) in PCT Application No. PCT/US2018/000238 dated Nov. 20, 2018. 10 pages.
Ochoa-Repáraz, Javier, et al. "Humoral immune response in hens naturally infected with Salmonella enteritidis against outer membrane proteins and other surface structural antigens." Veterinary research 35.3 (2004): 291-298.
Okamura, M., et al. "Immunization with outer membrane protein a from Salmonella enterica serovar Enteritidis induces humoral immune response but no protection against homologous challenge in chickens." Poultry science 91.10 (2012): 2444-2449.
Strindelius, Lena, Lena Degling Wikingsson, and Ingvar Sjöholm. "Extracellular antigens from Salmonella enteritidis induce effective immune response in mice after oral vaccination." Infection and immunity 70.3 (2002): 1434-1442.

* cited by examiner

1. Mock
2. Mock + Ch.
3. OMPs and flagellar + Ch.
4. OMPs-F-PNPs + Ch.

1. Mock
2. Mock + Ch.
3. OMPs and flagellar + Ch.
4. OMPs-F-CS NPs + Ch.

1. Mock
2. Mock + Ch.
3. OMPs and flagellar + Ch.
4. OMPs-F-CS NPs + Ch.

1. Mock + Ch.
2. OMPs and flagellar+ Ch.
3. OMPs-F-CS NPs in oral delivery + Ch.
4. OMPs-F-CS NPs in drinking water delivered + Ch.
5. OMPs-F-CS NPs in feed delivered + Ch.

1. Mock + Ch.
2. KAg+ Ch.
3. KAg-F-PNPs + Ch.
4. KAg-F-CS NPs + Ch.

NANOPARTICLE COMPOSITIONS FOR *SALMONELLA* VACCINES

CROSS-REFERENCE TO RELATED APPLICATIONS

This application is a national stage application filed under 35 U.S.C. § 371 of PCT/US2018/000238 filed Aug. 16, 2018, which claims the benefit of U.S. Provisional Patent Application Ser. No. 62/546,164 filed Aug. 16, 2017, each of which r expressly incorporated herein by reference.

STATEMENT REGARDING FEDERALLY SPONSORED RESEARCH

This invention was made with Government Support under Grant No. 2011-02925 awarded by the United States Department of Agriculture. The Government has certain rights to the invention.

FIELD

The present disclosure relates to nanoparticle compositions for use as vaccines against *Salmonella*.

BACKGROUND

Salmonellosis in poultry remains a major health problem in the United States and globally. Salmonellosis is a zoonotic disease caused by the Gram-negative enteric bacterium *Salmonella*. *Salmonella enterica* serovar *enteritidis* (*S. enteritidis*) is a rod-shaped bacterium and has emerged as a major food-borne pathogen in the United States. The World Health Organization has estimated that annually 1.3 billion cases of acute gastroenteritis and diarrhea are due to non-typhoidal salmonellosis with 3 million deaths. During the last few decades a considerable alarm was raised against *Salmonella* infections globally. Poultry and poultry derived products are epidemiologically attributed as a major reservoir of *S. enteritidis* infection in humans. Moreover, *S. enteritidis* causes notable economic losses to the poultry industry in addition to human health. Thus, effective control of *S. enteritidis* infection in poultry is required to develop a healthy environment for both birds and humans.

Vaccination is one of the possible ways of reducing *S. enteritidis* shedding in infected poultry. Various forms of live attenuated and killed *Salmonella* vaccines are currently used to mitigate Salmonellosis. However, the current vaccines only marginally decrease rather than eliminate the *Salmonella* colonization in chickens under field conditions. Killed whole bacterial vaccine provides only partial protection due to loss of antigenicity during the preparation stage and are unable to induce cell-mediated immunity. Furthermore, the killed vaccines have to be injected manually which makes delivery impractical in big farms with millions of birds. Live *Salmonella* vaccine, though effective, has a high chance of reversal to virulence, and the altered vaccine strain may thus spread to the environment and humans. Therefore, developing a potent killed and/or subunit oral *Salmonella* vaccine which can induce robust mucosal IgA and cell-mediated responses is warranted to control Salmonellosis in poultry.

Oral vaccination is simple and preferable in poultry for mass application; and it directly delivers antigens to gut associated lymphoid tissues (GALTs) resulting in initiation of higher mucosal IgA response compared to intramuscular vaccination. However, orally delivered vaccine antigens have high chance of degradation by gastric pH and thus show weak uptake by mucosal M cells and antigen presenting cells (APCs) in the GALT. Therefore, a novel vaccine antigen delivery and adjuvant system are critical to overcome these hurdles in an oral *Salmonella* vaccine.

The compositions and methods disclosed herein address these and other needs.

SUMMARY

Disclosed herein are nanoparticle compositions for use as vaccines against *Salmonella enteritidis* in poultry. The inventors have developed novel *Salmonella* vaccines comprising: highly immunogenic protein antigens (outer membrane proteins (OMPs) or *Salmonella enteritidis* killed whole antigenic extracted (KAg) protein) and flagellar protein, which are entrapped in polyanhydride or chitosan nanoparticles. These vaccine compositions are delivered orally in birds, target the vaccine antigens to the gastrointestinal tract, and induce the robust mucosal and cellular immune responses required to reduce colonization and clearance of *Salmonella*.

In one aspect, disclosed herein is a composition comprising: a *Salmonella enteritidis* outer membrane protein (OMP) or *Salmonella enteritidis* killed whole antigenic extracted (KAg) protein; and a polyanhydride or chitosan nanoparticle. In some embodiments, the nanoparticle further comprises flagellar protein. In some embodiments, the flagellar protein is both entrapped within the nanoparticle and is present on the surface of the nanoparticle. In some embodiments, the nanoparticle is immunogenic. In some embodiments, the nanoparticle comprises polyanhydride. In some embodiments, the nanoparticle comprises chitosan.

In some embodiments, the composition further comprises an adjuvant. In some embodiments, the *Salmonella enteritidis* OMP protein or KAg protein is entrapped within the nanoparticle. In some embodiments, the composition is formulated for oral delivery.

In some aspects, disclosed herein is a vaccine comprising: a composition comprising a *Salmonella enteritidis* OMP protein or *Salmonella enteritidis* killed whole antigenic extracted (KAg) protein; a polyanhydride or chitosan nanoparticle; and a pharmaceutically acceptable carrier.

In some aspects, disclosed herein is a vaccine comprising: a composition comprising a *Salmonella enteritidis* OMP protein or *Salmonella enteritidis* killed whole antigenic extracted (KAg) protein; a *Salmonella enteritidis* flagellar protein; a polyanhydride or chitosan nanoparticle; and a pharmaceutically acceptable carrier.

In some embodiments, the vaccine is administered orally.

In other aspects, disclosed herein is a method of eliciting an immune response against *Salmonella enteritidis* in a bird comprising: administering to the bird a vaccine comprising a composition comprising a *Salmonella enteritidis* OMP protein or *Salmonella enteritidis* killed whole antigenic extracted (KAg) protein; a polyanhydride or chitosan nanoparticle; and a pharmaceutically acceptable carrier.

In other aspects, disclosed herein is a method of eliciting an immune response against *Salmonella enteritidis* in a bird comprising: administering to the bird a vaccine comprising a composition comprising a *Salmonella enteritidis* OMP protein or *Salmonella enteritidis* killed whole antigenic extracted (KAg) protein; a *Salmonella enteritidis* flagellar protein; a polyanhydride or chitosan nanoparticle; and a pharmaceutically acceptable carrier.

BRIEF DESCRIPTION OF THE DRAWINGS

The accompanying figures, which are incorporated in and constitute a part of this specification, illustrate several aspects described below.

(FIG. 1C) SDS-PAGE analyses—Lane 1: Standard protein marker; Lane 2: Flagellar; Lane 3: OMPs (The position of some known proteins bands are shown by arrows).

(FIG. 4A) Hemolysis assay in chicken RBCs: 1. Positive control; 2. Negative control; 3-6. Increasing concentration of PNPs. (FIG. 4B) Microscopy images of chicken RBCs incubated with (a) TRITON® x-100 (Positive control); (b) PBS (Negative control); (c) PNPs (1000 μg/ml). (FIG. 4C) PNPs stability in different pH conditions over a period of 3 h, the percentage of absorbance reduction was measured by ELISA at 405 nm.

(FIG. 5A) Hemolysis assay in chicken RBCs: 1. Positive control; 2. Negative control; 3-6. Increasing concentration of CS NPs. (FIG. 5B) Microscopy images of chicken RBCs incubated with (a) TRITON® x-100 (Positive control); (b) PBS (Negative control); (FIG. 5C) CS NPs (1000 μg/ml). (C) CS NPs stability in different pH conditions over a period of 3 h, the percentage of absorbance reduction was measured by ELISA at 405 nm.

FIGS. 9A-9F. Post-challenge OMPs-specific antibody response in chickens vaccinated orally with OMPs-F-PNPs. Layer chickens vaccinated orally three times with mock saline (group 1 & 2) or OMPs and flagellar proteins (group 3) or entrapped in NPs (OMPs-F-PNPs) (group 4). Except mock group other groups were challenged orally with $10^9$ CFU/mL of live S. enteritidis, and euthanized at day 10 post-challenge. Samples collected from birds were analyzed for: (FIG. 9A) IgG in serum; (FIG. 9B) IgG in bile; (FIG. 9C) IgA in bile; (FIG. 9D) IgA in cloacal swab; (FIG. 9E) IgA in small intestinal wash; (FIG. 9F) IgA in tracheal wash. Each bar is the mean±SEM of 8 to 10 chickens, and the data were analyzed by non-parametric Kruskal-Wallis test followed by p value differences in between the groups were determined by Mann-Whitney test. Asterisk refers to statistical difference between two indicated groups ($*P<0.05$, $P<0.01$ and $*P<0.001$).

FIGS. 11A-11E. Post-challenge OMPs-specific antibody response in chickens vaccinated orally with OMPs-F-CS NPs. Layer chickens vaccinated orally three times with mock saline (group 1 & 2) or OMPs and flagellar proteins (group 3) or entrapped in NPs (OMPs-F-CS NPs) (group 4). Except mock group other groups were challenged orally with $10^9$ CFU/mL of live S. enteritidis, and euthanized at day 10 post-challenge. Samples collected from birds were analyzed for: (FIG. 11A) IgA in serum; (FIG. 11B) IgA in bile; (FIG. 11C) IgA in cloacal swab; (FIG. 11D) IgA in tracheal wash and (FIG. 11E) IgA in small intestinal wash. Each bar is the mean±SEM of 8 to 10 chickens, and the data were analyzed by non-parametric Kruskal-Wallis test followed by p value differences in between the groups were determined by Mann-Whitney test. Asterisk refers to statistical difference between two indicated groups ($*P<0.05$, $P<0.01$ and $*P<0.001$).

(FIG. 12A) Serum IFN-γ levels estimated by ELISA. OMPs-specific lymphocytes proliferation measured as stimulation index values in (FIG. 12B) PBMC and (FIG. 12C) Splenocytes, determined by a calorimetric assay. Each bar is the mean±SEM of 8 to 10 chickens, and the data were analyzed by non-parametric Kruskal-Wallis test followed by p value differences in between the groups were determined by Mann-Whitney test.

(FIG. 13A) Serum was estimated for IFN-γ production by ELISA. On the day of necropsy PBMC and splenocytes were isolated restimulated with OMPs to measure antigen specific cell proliferation SI in (FIG. 13B) PBMC and (FIG. 13C) Splenocytes by a calorimetric assay. The SI was calculated by the mean OD of OMPs stimulated proliferation/mean OD of non-stimulated proliferation. Each bar is the mean±SEM of 9 to 10 chickens, and the data were analyzed by non-parametric Kruskal-Wallis test followed by p value differences in between the groups were determined by Mann-Whitney test.

(FIG. 14B) TLR-4; (FIG. 14C) TGF-ß; (FIG. 14D) IL-4 and (FIG. 14E) IFN-γ. Each bar is the mean±SEM of 7 to 10 chickens, and the data were analyzed by non-parametric Kruskal-Wallis test followed by p value differences in between the groups were determined by Mann-Whitney test. Asterisk refers to statistical difference between two indicated groups (*P<0.05).

(FIG. 15B) TLR-4; (FIG. 15C) IFN-γ; (FIG. 15D) TGF-ß; (FIG. 15E) IL-4; (FIG. 15F) IL-1ß; and (FIG. 15G) iNOS were normalized to the expression of ß-actin. Each bar is the mean±SEM of 9 to 10 chickens, and the data were analyzed by non-parametric Kruskal-Wallis test followed by p value differences in between the groups were determined by Mann-Whitney test.

DETAILED DESCRIPTION

Figure 1A:
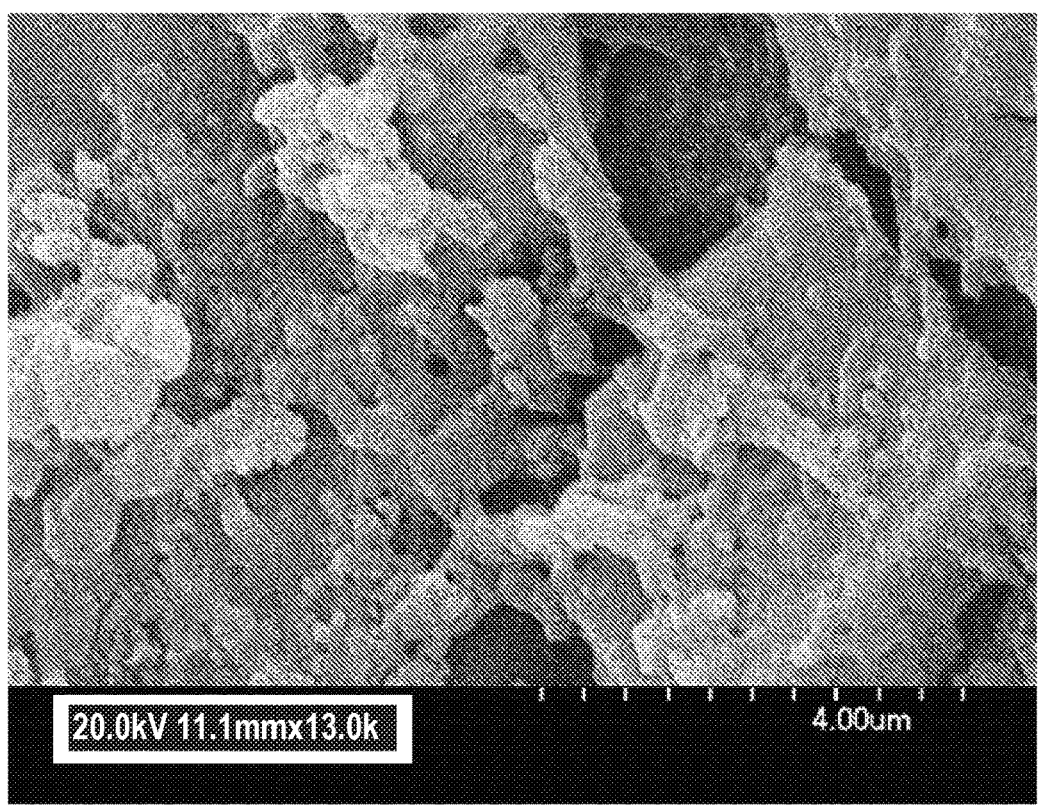
FIGS. 1A-1C. Confirmation of S. enteritidis extracted proteins. SEM analysis of (FIG. 1A) Flagellar protein (FIG. 1B) OMPs, (Scale bar: 13 Kx and 4 um)

Disclosed herein are nanoparticle compositions for use as vaccines against *Salmonella enteritidis* in poultry. The inventors have developed novel *Salmonella* vaccines comprising: highly immunogenic protein antigens (outer membrane proteins (OMPs) or *Salmonella enteritidis* killed whole antigenic extracted (KAg) protein) and flagellar protein, which are entrapped in polyanhydride or chitosan nanoparticles. These vaccine compositions are delivered orally in birds, target the vaccine antigens to the gastrointestinal tract, and induce the robust mucosal and cellular immune responses required to reduce colonization and clearance of *Salmonella*.

Reference will now be made in detail to the embodiments of the invention, examples of which are illustrated in the drawings and the examples. This invention may, however, be embodied in many different forms and should not be construed as limited to the embodiments set forth herein.

Unless defined otherwise, all technical and scientific terms used herein have the same meaning as commonly understood to one of ordinary skill in the art to which this disclosure belongs. The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments and are also disclosed.

The following definitions are provided for the full understanding of terms used in this specification.

Terminology

As used herein, the article "a," "an," and "the" means "at least one," unless the context in which the article is used clearly indicates otherwise.

The term "subject" or "host" refers to any individual or animal who is the target of administration or treatment. The subject can be a vertebrate, for example, a mammal. Thus, the subject can be a human or veterinary subject. In some embodiments, the subject can be a bird. In some embodiments, the subject can be a swine.

The term "variant" or "derivative" as used herein refers to an amino acid sequence derived from the amino acid sequence of the parent protein having one or more amino acid substitutions, insertions, and/or deletions.

An "immunogenic composition" is a composition of matter suitable for administration to a human or animal subject (e.g., in an experimental setting) that is capable of eliciting a specific immune response, e.g., against a pathogen, such as *Salmonella enteritidis*. As such, an immunogenic composition includes one or more antigens (for example, antigenic subunits, e.g., polypeptides; or whole killed bacterial antigenic extracted protein or live modified strain or a combination of both) or antigenic epitopes. An immunogenic composition can also include one or more additional components capable of eliciting or enhancing an immune response, such as an excipient, carrier, and/or adjuvant. In certain instances, immunogenic compositions are administered to elicit an immune response that protects the subject against symptoms or conditions induced by a pathogen. In some cases, symptoms or disease caused by a pathogen is prevented (or treated, e.g., reduced or ameliorated) by inhibiting replication of the pathogen following exposure of the subject to the pathogen. In the context of this disclosure, the term immunogenic composition will be understood to encompass compositions that are intended for administration to a subject or population of subjects for the purpose of eliciting a protective immune response against the pathogen (that is, vaccine compositions or vaccines).

An "antigen" is a compound, composition, or substance that can stimulate the production of antibodies and/or a T cell response in an animal, including compositions that are injected, absorbed or otherwise introduced into an animal. The term "antigen" includes all related antigenic epitopes. The term "epitope" or "antigenic determinant" refers to a site on an antigen to which B and/or T cells respond. The "dominant antigenic epitopes" or "dominant epitope" are those epitopes to which a functionally significant host immune response, e.g., an antibody response or a T-cell response, is made. Thus, with respect to a protective immune response against a pathogen, the dominant antigenic epitopes are those antigenic moieties that when recognized by the host immune system result in protection from disease caused by the pathogen. The term "T-cell epitope" refers to an epitope that when bound to an appropriate MHC molecule is specifically bound by a T cell (via a T cell receptor). A "B-cell epitope" is an epitope that is specifically bound by an antibody (or B cell receptor molecule). An antigen can also affect the innate immune response.

An "immune response" is a response of a cell of the immune system, such as a B cell, T cell, or monocyte, to a stimulus. An immune response can be a B cell response, which results in the production of specific antibodies, such as antigen specific neutralizing antibodies. An immune response can also be a T cell response, such as a CD4+ T cell response or a CD8+ T cell response. In some cases, the response is specific for a particular antigen (that is, an "antigen-specific response"). An immune response can also include the innate response. If the antigen is derived from a pathogen, the antigen-specific response is a "pathogen-specific response." A "protective immune response" is an immune response that inhibits a detrimental function or activity of a pathogen, reduces infection by a pathogen, or decreases symptoms (including death) that result from infection by the pathogen. A protective immune response can be measured, for example, by the inhibition of viral replication or plaque formation in a plaque reduction assay or ELISA-neutralization assay, or by measuring resistance to pathogen challenge in vivo.

The immunogenic compositions disclosed herein are suitable for preventing, ameliorating and/or treating disease caused by infection of the pathogen.

The term "treatment" or "treating" refers to the medical management of a subject with the intent to cure, ameliorate, or stabilize a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. This term includes administration of the compositions disclosed herein to a subject, by any appropriate delivery method.

The term "prevent" or "prevention" refers to a treatment that forestalls or slows the onset of a disease or condition or reduces the severity of the disease or condition. Thus, if a treatment can treat a disease in a subject having symptoms of the disease, it can also prevent that disease in a subject who has yet to suffer some or all of the symptoms.

Compositions and Methods

In one aspect, disclosed herein is a composition comprising: 1) a *Salmonella enteritidis* outer membrane protein (OMP) or *Salmonella enteritidis* killed whole antigenic extracted (KAg) protein; and 2) a polyanhydride or chitosan nanoparticle. In some embodiments, the nanoparticle further comprises flagellar protein.

In one embodiment, disclosed herein is a composition comprising: 1) a *Salmonella enteritidis* outer membrane protein (OMP); and 2) a polyanhydride or chitosan nanoparticle. In one embodiment, disclosed herein is a composition comprising: 1) *Salmonella enteritidis* killed whole antigenic extracted (KAg) protein; and 2) a polyanhydride or chitosan nanoparticle In one aspect, disclosed herein is a composition comprising: 1) a *Salmonella enteritidis* outer membrane protein (OMP) or *Salmonella enteritidis* killed whole antigenic extracted (KAg) protein; 2) a *Salmonella enteritidis* flagellar protein; and 3) a polyanhydride or chitosan nanoparticle.

In one embodiment, disclosed herein is a composition comprising: 1) a *Salmonella enteritidis* outer membrane protein (OMP); 2) a *Salmonella enteritidis* flagellar protein; and 3) a polyanhydride or chitosan nanoparticle. In one embodiment, disclosed herein is a composition comprising: 1) *Salmonella enteritidis* killed whole antigenic extracted (KAg) protein; 2) a *Salmonella enteritidis* flagellar protein; and 3) a polyanhydride or chitosan nanoparticle.

In some embodiments, the composition further comprises an adjuvant. In some embodiments, the *Salmonella enteritidis* outer membrane protein (OMP) or *Salmonella enteritidis* killed whole antigenic extracted (KAg) protein is entrapped within the nanoparticle. In some embodiments, the composition is formulated for oral delivery.

In some aspects, disclosed herein is a vaccine comprising: a composition comprising a *Salmonella enteritidis* outer membrane protein (OMP) or *Salmonella enteritidis* killed whole antigenic extracted (KAg) protein; a polyanhydride or chitosan nanoparticle; and a pharmaceutically acceptable carrier.

In some aspects, disclosed herein is a vaccine comprising: a composition comprising a *Salmonella enteritidis* OMP protein or *Salmonella enteritidis* killed whole antigenic extracted (KAg) protein; a *Salmonella enteritidis* flagellar protein; a polyanhydride or chitosan nanoparticle; and a pharmaceutically acceptable carrier.

In some embodiments, the vaccine is administered orally.

In other aspects, disclosed herein is a method of eliciting an immune response against *Salmonella enteritidis* in a subject comprising: administering to the subject a vaccine comprising a composition comprising: a *Salmonella enteritidis* OMP protein or *Salmonella enteritidis* killed whole antigenic extracted (KAg) protein; and a polyanhydride or chitosan nanoparticle: and a pharmaceutically acceptable carrier.

In other aspects, disclosed herein is a method of eliciting an immune response against *Salmonella enteritidis* in a subject comprising: administering to the subject a vaccine comprising a composition comprising: a *Salmonella enteritidis* OMP protein or *Salmonella enteritidis* killed whole antigenic extracted (KAg) protein; a *Salmonella enteritidis* flagellar protein; and a polyanhydride or chitosan nanoparticle; and a pharmaceutically acceptable carrier.

In other aspects, disclosed herein is a method of eliciting an immune response against *Salmonella enteritidis* in a bird comprising: administering to the bird a vaccine comprising a composition comprising: a *Salmonella enteritidis* OMP protein or *Salmonella enteritidis* killed whole antigenic extracted (KAg) protein; and a polyanhydride or chitosan nanoparticle: and a pharmaceutically acceptable carrier.

In other aspects, disclosed herein is a method of eliciting an immune response against *Salmonella enteritidis* in a bird comprising: administering to the bird a vaccine comprising a composition comprising: a *Salmonella enteritidis* OMP protein or *Salmonella enteritidis* killed whole antigenic extracted (KAg) protein; a *Salmonella enteritidis* flagellar protein; and a polyanhydride or chitosan nanoparticle; and a pharmaceutically acceptable carrier.

In one aspect, disclosed herein is a composition comprising: 1) one or more *Salmonella enteritidis* outer membrane proteins (OMP) or *Salmonella enteritidis* killed whole antigenic extracted (KAg) protein; and 2) a polyanhydride or chitosan nanoparticle. In some embodiments, the nanoparticle further comprises flagellar protein.

In one aspect, disclosed herein is a composition comprising: 1) one or more *Salmonella enteritidis* outer membrane proteins (OMP) or *Salmonella enteritidis* killed whole antigenic extracted (KAg) protein; 2) one or more *Salmonella enteritidis* flagellar proteins; and 3) a polyanhydride or chitosan nanoparticle.

In one aspect, disclosed herein is a composition comprising: 1) a *Salmonella enteritidis* outer membrane protein (OMP) or *Salmonella enteritidis* killed whole antigenic extracted (KAg) protein; and 2) a polyanhydride nanoparticle. In some embodiments, the nanoparticle further comprises flagellar protein.

In one aspect, disclosed herein is a composition comprising: 1) a *Salmonella enteritidis* outer membrane protein (OMP) or *Salmonella enteritidis* killed whole antigenic extracted (KAg) protein; 2) a *Salmonella enteritidis* flagellar protein; and 3) a polyanhydride nanoparticle.

In one aspect, disclosed herein is a composition comprising: 1) a *Salmonella enteritidis* outer membrane protein (OMP) or *Salmonella enteritidis* killed whole antigenic extracted (KAg) protein; and 2) a chitosan nanoparticle. In some embodiments, the nanoparticle further comprises flagellar protein.

In one aspect, disclosed herein is a composition comprising: 1) a *Salmonella enteritidis* outer membrane protein (OMP) or *Salmonella enteritidis* killed whole antigenic extracted (KAg) protein; 2) a *Salmonella enteritidis* flagellar protein; and 3) a chitosan nanoparticle.

Figure 1B:
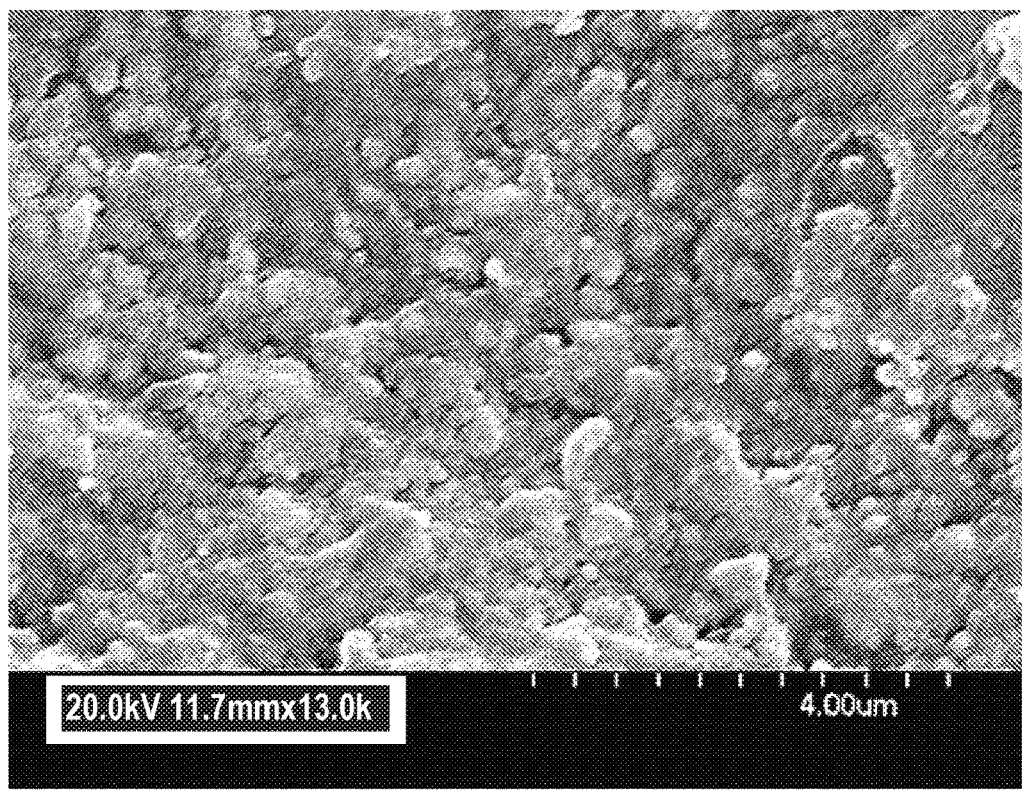
Figure 1C:
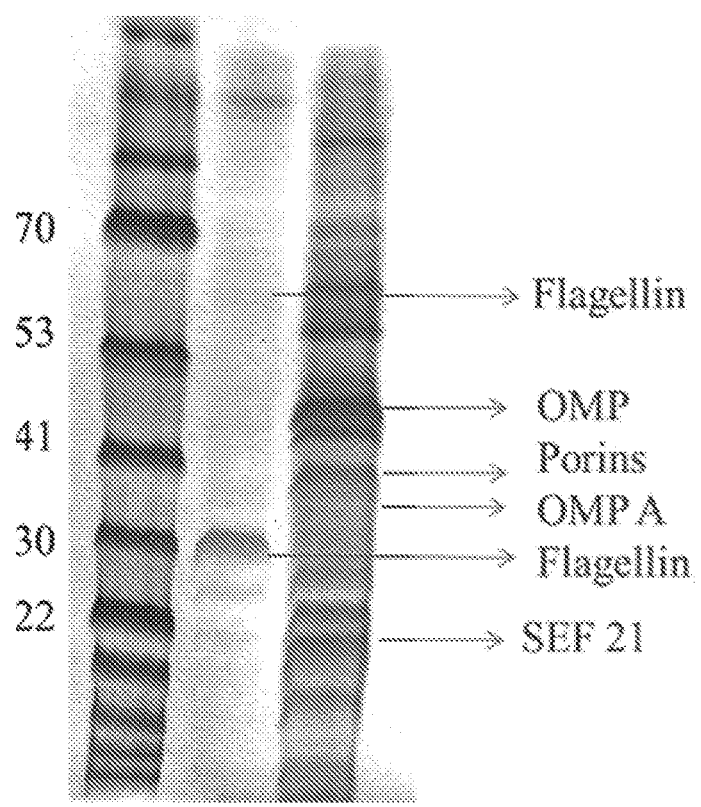

The outer membrane proteins (OMPs) of *salmonella* are highly immunogenic as it is easily identified by the host immune system. When compared to killed bacterial extract, partially purified OMPs induce better protective response against virulent *Salmonella* infection. Enriched OMPs delivered with a potent adjuvant elicits strong immune response and decrease the *Salmonella* shedding in poultry. The OMPs function in adhesion, immune targeting and activation of professional antigen presenting cells (APCs) essential for induction of immunity. The OMPs from *S. enteritidis* can be isolated using a sequential detergent extraction method as described previously (Ochoa-Reparaz J, et al. Vet Res. 2004; 35:291-8) with some modifications as described herein. For preparation of CS NPs, the OMPs from *S. enteritidis* can be isolated using Tris-sucrose-EDTA (TSE) buffer as described previously (Quan S, et al. Methods Mol Biol. 2013; 966: 359-66) with some modifications as described herein. In some embodiments, the OMP protein extract used herein is shown in FIG. 1C (lane 3).

In some embodiments, the OMP protein is an OMP protein extract from *S. enteritidis*. In some embodiments, the OMP protein is an OMP protein extract from *S. enteritidis* isolated using a sequential detergent extraction. In some embodiments, the OMP protein is an OMP protein extract from *S. enteritidis* comprising at least one protein selected from OMP, OMP A, Porins, and/or SEF 21 (for example, OMP, NCBI Protein Accession No. KOX82125).

In some embodiments, other related *Salmonella* serotype proteins can also be used, for example, *Salmonella enteritidis* killed whole bacterium antigenic extracted protein, *Salmonella typhimurium* outer membrane protein or killed whole bacterium antigenic extracted protein, *Salmonella heidelberg* outer membrane protein or killed whole bacterium antigenic extracted protein or a combination thereof.

In some embodiments, additional antigens from other serovars of *Salmonella* such as *S. typhimurium, S. typhi, S. kentucky, S. heidelberg, S. gallinarum, S. abortusequi, S. cholerasuis, S. dublin, S. newport*, etc., can be included in the vaccine formulation, depending on the requirement to increase the breadth of immunity in birds of all ages.

The killed whole bacterium soluble protein antigens of *Salmonella* sp. was extracted by using the sonication method as described previously (Anna George, et al. Microbiol. Immuno. 1989; 33: 479-488; incorporated by reference herein in its entirety) with some modifications as described herein (NCBI Nucleotide Accession No. CP007267.2).

In some embodiments, the nanoparticle is immunogenic. In some embodiments, the nanoparticle comprises polyanhydride. In some embodiments, the nanoparticle comprises chitosan. In some embodiments, the *Salmonella enteritidis* OMP protein is entrapped within the nanoparticle. In some embodiments, the *Salmonella enteritidis* killed whole antigenic extracted (KAg) protein is entrapped within the nanoparticle.

In some embodiments, the nanoparticle further comprises flagellar protein. In some embodiments, the nanoparticle comprises flagellar protein on the surface of the nanoparticle. In some embodiments, the flagellar protein is both entrapped within the nanoparticle and is present on the surface of the nanoparticle. In some embodiments, the flagellar protein is cross-linked with the nanoparticle. In some embodiments, the flagellar protein is coated on the surface of the nanoparticle without any chemical activation. In some embodiments, the nanoparticle further comprises a flagellar protein extract. In some embodiments, the nanoparticle further comprises a flagellar protein extract from *Salmonella enteritidis*. In some embodiments, the nanoparticle further comprises a flagellar protein is extracted as described herein from an *S. enteritidis* bacterial culture. In some embodiments, the flagellar protein extract used herein is shown in FIG. 1C (lane 2) (for example, Flagellin/Flagellar Protein, NCBI Protein Accession No ANF18340). In some embodiments, the flagellar protein is both entrapped within the nanoparticle and is present on the surface of the nanoparticle.

The morphology of isolated *Salmonella* antigens, OMPs and flagellar protein, is determined by SEM analysis. Both OMPs and flagellin/flagellar protein can be in spherical and irregular shapes and aggregated in the form of a matrix (FIG. 1A&1B). Complex proteins present in OMPs enriched extract of *S. enteritidis* have been reported (Hamid N, Jain S K. Clin Vaccine Immunol. 2008; 15:1461-71). SDS-PAGE analysis of isolated OMPs revealed a complex electrophoretic profile containing greater than 12 different proteins ranging from 14 to 70 kDa. Among them the major well characterized antigenic proteins are having the molecular weight 22, 23, 28, 34, 36, 45, 46, 55, 65, 68 and 70 kDa (FIG. 1C). The flagellar enriched extract was having the flagella specific proteins based on the molecular weight (Komoriya K, et al. Mol Microbiol. 1999; 34:767-79 which is incorporated herein by reference in its entirety): FlgD 28 kDa, FlgL 35 kDa, FlgE 42 kDa, FlgD 50 kDa, FlgK 58 kDa and also surface appendages protein SEF21 21 kDa (FIG. 1C). In some embodiments, the OMP protein is an OMP protein extract from *S. enteritidis* comprising at least one protein selected from the major well characterized antigenic proteins are having the molecular weight 22, 23, 28, 34, 36, 45, 46, 55, 65, 68 and 70 kDa, as shown in FIG. 1C (lane 3). In some embodiments, the flagellar protein (flagellin) comprises at least one protein selected from FlgD 28 kDa, FlgL 35 kDa, FlgE 42 kDa, FlgD 50 kDa, FlgK 58 kDa and/or the surface appendages protein SEF21 21 kDa, as shown in FIG. 1C (lane 2).

Biodegradable polymeric nanoparticles can be used in the vaccine compositions and delivery systems disclosed herein. Because of the nanoscale size, feasible physicochemical properties, more surface area, biocompatibility, and biodistribution, the nanoparticles protect the loaded cargo from biological barriers and can deliver the vaccines to mucosal immune cells. Orally delivered polymeric nanoparticle vaccines should be mucoadhesive and bioavailable for prolonged period of time without getting degraded at the mucosal surfaces in the gastrointestinal (GI) tract.

One example of a biodegradable polymer for oral delivery of vaccines includes poly (methyl vinyl ether-co-maleic anhydride) (called polyanhydride), which is well characterized and it possesses a great potential in biomedical applications. Copolymerization of polyvinyl methyl ether and maleic acid at appropriate levels provides a natural bioadhesive and biocompatible properties. Polyanhydride polymer hydrolytically degrades, and the cleaved anhydride has a carboxylic acid group which forms a hydrogen bond with the components of mucosal surface.

Poly(methyl vinyl ether-alt-maleic anhydride) structure

Chitosan structure

In some embodiments, other related mucosal adhesive polymers can also be used, for example: Methylglycol chitosan, Glycol chitosan, High molecular weight chitosan, Collagen, Albumin, Gelatin, Alginates, Cyclodextrines, Dextran, Agarose, Hyaluronic acid, Starch, Cellulose, Polylactic acid, Polyglycolic acid, Polyhydroxyl butyrate, Polycaprolactone, Poly Doxanones, Polyadipic acid, Polyterphthalicacid, Polysebacic acid, Poly iminocarbonates, Poly amino acids, Polyphosphates, Polyphosphonates, Polyphosphazenes, Poly cyanocrylates, Poly urethanes, Poly ortho esters, Polyacetals, or a combination thereof.

In some embodiments, other related cross linkers for chitosan nanoparticle formation can also be used, for example: Curdlan sulfate, sodium citrate, sulfosuccinic acid, oxalic acid, glutaraldehyde, epichlorohydrin, trimethylpropane triglycidyl ether, and ethylene glycol diglycidyl ether or a combination thereof.

In some embodiments, the microorganisms derived adhesive factors like flagellar protein and specific sugars decorated (for example, mannose) on the surface of the nanoparticles can further enhance the bioadhesive nature and targeting of the vaccine to GI tract Peyer's patches (PPs). Fluorescent labelled and flagellar protein coated polyanhydride nanoparticles (PNPs) delivered orally adhere to the GI tract and actively uptaken by ileum PPs M cells of rats. Ovalbumin loaded and surface flagellar protein coated PNPs delivered orally induce balanced Th1 and Th2 immune response in mice.

Another example biodegradable agent is chitosan, which is a natural cationic copolymer derived from the partial deacetylation of chitin, primarily resourced from crustacean and insect shells. Chitosan is composed of randomly distributed N-acetyl glucosamine and D-glucosamine, which offers positive charge to the polymer. Chitosan is biocompatible and because of its cationic nature it has strong mucoadhesive and membrane permeability enhancing properties. Chitosan has amino and carboxyl groups which interact with mucus glycoprotein and form a hydrogen bond and provides adhesive effect. Moreover, chitosan interacts directly with the cell membrane through mucus layer and decreases the trans-epithelial electrical resistance of cell monolayers as well as increase the paracellular permeability. Chitosan nanoparticles (CS NPs) can also elicit robust immune response by activating macrophages and dendritic cells and secretion of cytokines.

Nanoparticles can aid the delivery of the *Salmonella* OMPs and/or can also be immunogenic. Delivery can be to a particular site of interest, e.g. the mucosa. In some embodiments, the nanoparticle can create a timed release of the *Salmonella* OMPs to enhance and/or extend the immune response. In some embodiments, the nanoparticle is associated with the *Salmonella* OMPs such that the composition can elicit an immune response. The association can be, for example, wherein the *Salmonella* OMPs are entrapped or encapsulated with the nanoparticle. By entrapped is meant that there is a physical encasing of the *Salmonella* OMPs in the nanoparticles. In some embodiments, the *Salmonella* OMPs are entrapped within the nanoparticle by a water/oil/water emulsion method. In some embodiments, the nanoparticle is formulated by a solvent displacement method as described (Salman H H, et al. Vaccine. 2009; 27:4784-90). In some embodiments, the nanoparticle is formulated by an ionic gelation method (See, for example, Zhao K, et al. Preparation and efficacy of a live newcastle disease virus vaccine encapsulated in chitosan nanoparticles. PLoS One. 2012; 7:e53314).

In some embodiments, the composition further comprises an adjuvant. In some embodiments, the composition is formulated for oral delivery.

In some aspects, disclosed herein is a vaccine comprising: a composition comprising a *Salmonella enteritidis* OMP protein and a polyanhydride or chitosan nanoparticle; and a pharmaceutically acceptable carrier.

Disclosed herein are illustrative immunogenic compositions, e.g., vaccine compositions. Additionally, the compositions described herein can comprise one or more immunostimulants. An immunostimulant refers to essentially any substance that enhances or potentiates an immune response (antibody or cell-mediated) to an exogenous antigen. One preferred type of immunostimulant comprises an adjuvant. Many adjuvants contain a substance designed to protect the antigen from rapid catabolism, such as aluminum hydroxide or mineral oil, and a stimulator of immune responses, such as lipid A, Bortadella pertussis or *Mycobacterium tuberculosis* derived proteins. Certain adjuvants are commercially available as, for example, Freund's Incomplete Adjuvant and Complete Adjuvant (Difco Laboratories, Detroit, Mich.); Merck Adjuvant 65 (Merck and Company, Rahway, N.J.); AS-2 (GlaxoSmithKline, Philadelphia, Pa.); aluminum salts such as aluminum hydroxide gel (alum) or aluminum phosphate; salts of calcium, iron or zinc; an insoluble suspension of acylated tyrosine; acylated sugars; cationically or anionically derivatized polysaccharides; polyphosphazenes; biodegradable microspheres; monophosphoryl lipid A and quil A. Cytokines, such as GM-CSF, interleukin-2, -7, -12, and other like growth factors, or combinations of one or more. may also be used as adjuvants.

The adjuvant composition can be a composition that induces an anti-inflammatory immune response (antibody or cell-mediated). Accordingly, high levels of anti-inflammatory cytokines (anti-inflammatory cytokines may include, but are not limited to, interleukin 4 (IL-4), interleukin 5 (IL-5), interleukin 10 (IL-10), and transforming growth factor beta (TGFβ). Optionally, an anti-inflammatory response would be mediated by CD4+T helper cells. Bacterial flagellin has been shown to have adjuvant activity (McSorley et al., J. Immunol. 169:3914-19, 2002). Also disclosed are polypeptide sequences that encode flagellar proteins that can be used in adjuvant compositions.

Polymers used in making the nanoparticle vaccine formulation themselves can also act as an adjuvant in vivo in birds, but additional secondary adjuvants can also be used to boost the immune response in additive or synergistic ways. Thus, in some embodiments, the vaccine formulations can include potent Toll-Like Receptor adjuvants such as CPG-ODN, poly (I:C), etc., in the final formulation.

Optionally, the adjuvants used in conjunction with the disclosed compositions increase lipopolysaccharide (LPS) responsiveness. Illustrative adjuvants include but are not limited to, monophosphoryl lipid A (MPL), aminoalkyl glucosaminide 4-phosphates (AGPs), including, but not limited to RC-512, RC-522, RC-527, RC-529, RC-544, and RC-560 (Corixa, Hamilton, Mont.).

In addition, the adjuvant composition can be one that induces an immune response predominantly of the Th1 type. High levels of Th1-type cytokines (e.g., IFN-γ, TNFα, IL-2 and IL-12) tend to favor the induction of cell mediated immune responses to an administered antigen. In contrast, high levels of Th2-type cytokines (e.g., IL-4, IL-5, IL-6 and IL-10) tend to favor the induction of humoral immune responses. Following application of a vaccine as provided herein, a subject supports an immune response that includes Th1- and Th2-type responses. Optionally, the level of Th1-type cytokines can increase to a greater extent than the level of Th2-type cytokines. The levels of these cytokines may be readily assessed using standard assays. The level of Th2-type cytokines can increase to a greater extent than the level of Th1-type cytokines. Certain adjuvants for eliciting a predominantly Th1-type response include, for example, a combination of monophosphoryl lipid A, preferably 3-de-O-acylated monophosphoryl lipid A, together with an aluminum salt adjuvants are available from Corixa Corporation (Seattle, Wash.; see, for example, U.S. Pat. Nos. 4,436,727; 4,877,611; 4,866,034 and 4,912,094, which are hereby incorporated by reference for their teaching of the same). CpG-containing oligonucleotides (in which the CpG dinucleotide is unmethylated) also induce a predominantly Th1 response. Such oligonucleotides are well known and are described, for example, in WO 96/02555, WO 99/33488 and U.S. Pat. Nos. 6,008,200 and 5,856,462 Immunostimulatory DNA sequences are also described, for example, by Sato et al., Science 273:352, 1996. Another adjuvant comprises a saponin, such as Quil A, or derivatives thereof, including QS21 and QS7 (Aquila Biopharmaceuticals Inc., Framingham, Mass.); Escin; Digitonin; or *Gypsophila* or *Chenopodium quinoa* saponins. Other formulations can include more than one saponin in the adjuvant combinations, for example combinations of at least two of the following group comprising QS21, QS7, Quil A, β-escin, or digitonin.

Saponin formulations can also be combined with vaccine vehicles composed of chitosan or other polycationic polymers, polylactide and polylactide-co-glycolide particles, poly-N-acetyl glucosamine-based polymer matrix, particles composed of polysaccharides or chemically modified polysaccharides, liposomes and lipid-based particles, particles composed of glycerol monoesters, etc. The saponins can also be formulated in the presence of cholesterol to form particulate structures such as liposomes or immune-stimulating complexes (ISCOMs). Furthermore, the saponins may be formulated together with a polyoxyethylene ether or ester, in either a non-particulate solution or suspension. The saponins can also be formulated with excipients such as CARBOPOL™ (Noveon, Cleveland, Ohio) to increase viscosity, or may be formulated in a dry powder form with a powder excipient such as lactose.

Optionally, the adjuvant system includes the combination of a monophosphoryl lipid A and a saponin derivative, such as the combination of QS21 and 3D-MPL. adjuvant, as described in WO 94/00153, or a less reactogenic composition where the QS21 is quenched with cholesterol, as described in WO 96/33739. Other formulations comprise an oil-in-water emulsion and tocopherol. Another adjuvant formulation employing QS21, 3D-MPL® adjuvant and tocopherol in an oil-in-water emulsion is described in WO 95/17210.

Another enhanced adjuvant system involves the combination of a CpG-containing oligonucleotide and a saponin derivative particularly the combination of CpG and QS21 is disclosed in WO 00/09159. Optionally the formulation additionally comprises an oil in water emulsion and tocopherol.

Additional illustrative adjuvants for use in the disclosed compositions Montamide ISA 720 (Seppic, France), SAF (Chiron, Calif., United States), ISCOMS (CSL), MF-59 (Chiron), the SBAS series of adjuvants (e.g., SBAS-2 or SBAS-4, available from GlaxoSmithKline, Philadelphia, Pa.), Detox (ENHANZYN™) (Corixa, Hamilton, Mont.), RC-529 (Corixa, Hamilton, Mont.) and other aminoalkyl glucosaminide 4-phosphates (AGPs), such as those described in pending U.S. patent application Ser. Nos. 08/853,826 and 09/074,720, the disclosures of which are incorporated herein by reference in their entireties, and polyoxyethylene ether adjuvants such as those described in WO 99/52549A1.

In other aspects, disclosed herein is a method of eliciting an immune response against Salmonella enteritidis in a bird comprising: administering to the bird a vaccine comprising a composition comprising: a Salmonella enteritidis OMP protein or Salmonella enteritidis killed whole antigenic extracted (KAg) protein; a polyanhydride or chitosan nanoparticle; and a pharmaceutically acceptable carrier.

In some embodiments, the vaccine is administered orally.

In some embodiments, the administration of the vaccine reduces bacterial shedding.

The method can further comprise administering to the bird virulent Salmonella to monitor the vaccine efficacy.

The composition or vaccine can be administered for example in a single dose, or in two or more doses. In one embodiment, three doses are administered. In one embodiment, the three doses are administered over a multi-week interval. In one embodiment, the three doses are administered over at three-week intervals between each dose. The composition or vaccine can, for example, be administered orally. Oral vaccination is simple and preferable in poultry for mass application; and it directly delivers antigens to gut associated lymphoid tissues (GALTs) resulting in initiation of higher mucosal IgA response compared to intramuscular vaccination. However, orally delivered vaccine antigens have high chance of degradation by gastric pH, proteolytic enzyme interference and thus weakly uptaken by mucosal M cells and APCs in the GALT. The novel vaccine compositions disclosed herein overcome these hurdles and provide an oral Salmonella vaccine. However, additional examples of alternative routes of immunization and delivery of the nanoparticle compositions disclosed herein can include intramuscular, subcutaneous, injection, subcutaneous, intradermal injection, breast injection or combination of route.

In some embodiments, the vaccine dose ranges from 0.05 to 2 mg per bird per dose.

In some embodiments, the vaccine compositions are administered by inclusion within the subject's feed. In some embodiments, the vaccine compositions are administered by inclusion within a water suspension provided to the subject or combination route.

The term "bird" as used herein refers to males or females of any bird species. The present invention, therefore, may be practiced with any type of bird, including but is not limited to chicken, turkey, duck, goose, quail, pheasant, grouse, or the chicks of any bird species. In some embodiments, the bird is a layer bird. In some embodiments, the bird is a broiler bird. In some embodiments, the bird is a chicken, a turkey, a goose, or a duck. In some embodiments, the bird is a chicken.

In some embodiments, the animal is a swine. The term "swine" as used herein is meant to include domesticated, wild, and feral swine and may be used interchangeably with the term "pig" or "porcine."

EXAMPLES

The following examples are set forth below to illustrate the compositions, methods, and results according to the disclosed subject matter. These examples are not intended to be inclusive of all aspects of the subject matter disclosed herein, but rather to illustrate representative methods and results. These examples are not intended to exclude equivalents and variations of the present invention which are apparent to one skilled in the art.

Example 1. Novel Biodegradable Nanoparticle Based Oral Delivery of Salmonella Vaccines for Poultry Salmonellosis in poultry remains a major health problem in the United States and globally. Significant economic losses reported through mortality and poor growth of Salmonella enteritidis (S. enteritidis) infected chicken. Also, the other major concern is the public health hazard through Salmonella food poisoning by consumption of contaminated meat and egg of poultry. Currently used Salmonella vaccines are not effective in combating the disease problem. Therefore, there is an urgent need to develop an effective vaccine, especially a potent oral Salmonella killed or subunit vaccine which elicits robust local mucosal immunity in the intestines. Biodegradable and biocompatible polymers are proven vehicles for drug and vaccine delivery. Two novel Salmonella vaccines were prepared containing highly immunogenic protein antigens, outer membrane proteins (OMPs) and flagellar protein, which are entrapped in polyanhydride nanoparticles and also surface decorated with flagellar protein (OMPs-F-PNPs), similarly in chitosan nanoparticles (OMPs-F-CS NPs). The physicochemical and biocompatibility properties of OMPs-F-PNPs and OMPs-F-CS NPs such as particle size distribution, surface morphology, protein loading efficiency, pH stability and toxicity analyses were performed. Like how the live Salmonella target the ileum Peyer's patches (PPs) M cells of chicken, fluorescent labelled OMPs-F-PNPs and OMPs-F-CS NPs were targeted to ileum PPs by ex vivo and in vivo studies. Interestingly, layer chickens vaccinated orally with OMPs-F-PNPs induced significantly higher OMPs specific systemic IgG and intestinal IgA response. While in OMPs-F-CS NPs vaccinated chickens had a significantly higher OMPs-specific intestinal IgA (but not systemic IgG) response, associated with enhanced proliferation of specific lymphocytes. Furthermore, OMPs-F-CS NPs induced significantly higher toll-like receptor (TLR)-4, TLR-2 and IFN-γ cytokine mRNA expression, and OMPs-F-PNPs induced significantly higher TLR-4 mRNA expression in the cecal tonsils of vaccinated birds. However, in vaccinated and very high challenge bacterial dose received birds, only OMPs-F-PNPs vaccine completely cleared the S. enteritidis cecal colonization in 33% of birds. In additional experiments, OMPs-F-CS NPs significantly reduced bacterial shedding compared to mock challenge birds. Further, *Salmonella enteritidis* killed whole bacterium antigenic extracted (KAg) protein loaded and surface flagellar coated polyanhydride nanoparticles (KAg—F-PNPs) and KAg protein loaded and surface flagellar coated chitosan nanoparticles (KAg—F-CS NPs) significantly reduced bacterial shedding compared to mock challenge birds. In conclusion, this example shows in birds for the first time demonstrated targeting of oral *Salmonella* nanovaccine to intestines, which induced specific antibody and T cell responses and reduced bacterial burden.

1. BACKGROUND

Salmonellosis is a zoonotic disease caused by the Gram-negative enteric bacterium *Salmonella. Salmonella enterica* serovar *enteritidis* is a rod shaped bacteria, emerged as a major food borne pathogen in the United States [1]. The World Health Organization has estimated that annually 1.3 billion cases of acute gastroenteritis and diarrhea are due to non-typhoidal salmonellosis with 3 million deaths [2]. Approximately 40,000 cases of salmonellosis and 2,000 deaths are reported annually in the United States, although the real number may be 30-fold greater [3]. During the last few decades a considerable alarm was raised against *salmonella* infections globally [4]. Poultry and poultry derived products are epidemiologically attributed as a major reservoir of *S. enteritidis* infection in humans [5]. Moreover, *S. enteritidis* causes notable economic losses to the poultry industry in addition to human health [6]. Thus, effective control of *S. enteritidis* infection in poultry is required to develop a healthy environment for both birds and humans [7].

Vaccination is one of the possible ways of reducing *S. enteritidis* shedding in infected poultry [8]. Various forms of live attenuated and killed *salmonella* vaccines are currently used to mitigate Salmonellosis [9-11]. But they only marginally decrease rather than eliminate the *Salmonella* colonization in chickens under field conditions [12-14]. Killed whole bacterial vaccine provides only partial protection due to loss of antigenicity during preparation stage and inability to induce cell-mediated immunity [15]. Furthermore, the killed vaccines have to be injected manually and thereby making its delivery practically not feasible in big farms with millions of birds. Live *Salmonella* vaccine though effective has a high chance of reversal to virulence [16], and the altered vaccine strain may spread to the environment and humans [17]. Therefore, developing a potent killed or subunit oral *Salmonella* vaccine which can induce robust mucosal IgA and cell-mediated responses is warranted to control Salmonellosis in poultry.

The outer membrane proteins (OMPs) of *salmonella* are highly immunogenic as it is easily identified by the host immune system [18]. When compared to killed bacterial extract, partially purified OMPs induce better protective response against virulent *Salmonella* infection [19]. Enriched OMPs delivered with a potent adjuvant elicits strong immune response and decrease the *Salmonella* shedding in poultry [20]. The OMPs function in adhesion, immune targeting and activation of professional antigen presenting cells (APCs) essential for induction of immunity [21].

Oral vaccination is simple and preferable in poultry for mass application; and it directly delivers antigens to gut associated lymphoid tissues (GALTs) resulting in initiation of higher mucosal IgA response compared to intramuscular vaccination [22, 23]. However, orally delivered vaccine antigens have high chance of degradation by gastric pH, proteolytic enzyme interference and thus weakly uptaken by mucosal M cells and APCs in the GALT [23, 24]. Therefore, a novel vaccine antigens delivery and adjuvant system are critical to overcome those hurdles in an oral *Salmonella* vaccine [22].

Biodegradable polymeric nanoparticles based vaccine delivery system has recently been gaining increased attention for use in food animals [25-27]. Because of the nanoscale size, feasible physicochemical properties, more surface area, biocompatibility, biodistribution, protect the loaded cargo from biological barriers and ability to target deliver vaccine to mucosal immune cells [25, 28-30]. Orally delivered polymeric nanoparticle vaccine should be mucoadhesive and bioavailable for prolonged period of time without getting degraded at the mucosal surfaces in the gastrointestinal (GI) tract [22].

Among different available biodegradable polymers for oral delivery of vaccines, poly (methyl vinyl ether-co-maleic anhydride) called polyanhydride is well characterized and it possesses a great potential in biomedical applications [31]. Copolymerization of polyvinyl methyl ether and maleic acid at appropriate levels provides a natural bioadhesive and biocompatible properties [32]. Polyanhydride polymer hydrolytically degrades, and the cleaved anhydride has a carboxylic acid group which form a hydrogen bond with the components of mucosal surface [33]. Recently, polyanhydride nanoparticles (PNPs) activating Toll-like receptors (TLRs)-2 and -4, innate immunity, complement system and APCs, leading to potent adjuvant properties required for triggering both the antibody and cellular immune responses was demonstrated [22, 34-36]. The microorganisms derived adhesive factors like flagellin and specific sugars decorated on the surface of PNPs further enhance the bioadhesive nature and targeting the vaccine to GI tract Peyer's patches (PPs) [22]. Fluorescent labelled and flagellin coated PNPs delivered orally adhere to the GI tract and actively uptaken by ileum PPs M cells of rats [36]. Ovalbumin loaded and surface flagellin coated PNPs delivered orally induce balanced Th1 and Th2 immune response in mice [22].

Another popular biodegradable agent is chitosan, it is a natural cationic copolymer derived from the partial deacetylation of chitin, primarily resourced from crustacean and insect shells. Chitosan is composed of randomly distributed N-acetyl glucosamine and D-glucosamine, which offers positive charge to the polymer [37, 38]. Chitosan is biocompatible and because of its cationic nature it has strong mucoadhesive and membrane permeability enhancing properties [39]. Chitosan has amino and carboxyl groups which interact with mucus glycoprotein and form a hydrogen bond and provides adhesive effect [40]. Moreover, chitosan interacts directly with the cell membrane through mucus layer and decreases the trans-epithelial electrical resistance of cell monolayers as well as increase the paracellular permeability [41, 42]. Therefore, chitosan nanoparticles (CS NPs) has been extensively investigated for its potential as absorption enhancer across intestinal epithelium for mucosal delivery of drugs, peptides and proteins [43]. Apart from efficiently delivering encapsulated vaccine antigens, CS NPs elicit robust immune response by activating macrophages and dendritic cells and secretion of cytokines [44].

In the present example, it is shown that *S. enteritidis* immunogenic antigens (OMPs and flagellar) loaded and surface flagellar decorated bioadhesive PNPs and CS NPs delivered orally in birds target the vaccine antigens to GI tract PPs, and induce the robust mucosal and cellular immune response required to reduce colonization and clearance of *Salmonella*.

2. MATERIALS AND METHOD

2.1. Isolation of OMPs

OMPs from *S. enteritidis* were isolated using a sequential detergent extraction method as described previously [45] with some modifications. Briefly, the growing stationary phase bacterial culture was washed using phosphate-buffered saline (PBS) pH 7.4 and the cells were lysed by high pressure in a French Press (QIAGEN-TissueLyser LT, MD). The bacterial inner membrane was solubilized by treating with 1% Sarkosyl (Sigma, MO) for 30 min and centrifuged (OPTIMA™ L-100XP Beckman Coulter ultracentrifuge) at 20,000×g for 30 min. The pellet was suspended in 10% sodium dodecyl sulfate (SDS) (In 0.5 M Tris-HCl, pH 6.8) for 30 min and centrifuged at 20,000×g for 30 min, and the supernatant containing soluble OMPs enriched extract was dialyzed against MILLI-Q® water and freeze-dried with 5% sucrose as a cryoprotectant. The protein concentration was estimated using micro BCA protein assay kit (Thermo Scientific, MA) as per the manufacturer's instruction.

For preparation of CS NPs, the OMPs from *S. enteritidis* were isolated using Tris-sucrose-EDTA (TSE) buffer as described previously [46] with some modifications. The stationary phase bacterial culture was washed with 10 mM Tris pH 7.5 and the sediment was suspended in TSE buffer pH 8 and incubated on ice for 90 min. The cell suspension was centrifuged at 16,000×g for 30 min and the collected supernatant was centrifuged at 100,000×g for 60 min. The pellet containing OMPs enriched extract was freeze-dried with 5% sucrose as a cryoprotectant, and the protein concentration was determined using micro BCA protein assay kit.

2.2. Isolation of Flagellar Proteins

*S. enteritidis* bacterial culture grown on TRYPTICASE® soy agar plates was inoculated to brain heart infusion broth and incubated for 48 h at 3TC without shaking. The cells were washed with PBS pH 7.4 and centrifuged at 7000×g for 30 min. The cells pellet was treated with 3M potassium thiocyanate (Sigma, MO) in PBS for 2 h at room temperature under magnetic stirring. Subsequently, the cell suspension was centrifuged at 35,000×g for 30 min and the supernatant containing flagellar enriched extract was dialyzed once against PBS pH 7.4 followed by MILLI-Q® water and freeze-dried with 5% sucrose as a cryoprotectant. The protein concentration was estimated using micro BCA protein assay kit.

2.3. Analyses of OMPs and Flagellar Protein by Sodium Dodeacylsulfate-Polyacrylamide Gel Electrophoresis (SDS-PAGE)

The isolated OMPs and flagellar protein were mixed with a gel loading dye containing ß-mercaptoethanol, denatured at 95° C. for 5 min before loading on to the gel. Separation of the protein was achieved using SDS-PAGE analyses using 5% (v/v) stacking and 10% (v/v) separation gels, followed by staining with Coomassie brilliant blue R-250 for 2 h. The stained gel was destained and the protein molecular weight was determined using a ladder of standard protein Mw marker [235-9 kilodalton (kDa)].

2.4 Isolation of KAg Proteins

*S. enteritidis* bacterial culture grown on TRYPTICASE® soy agar plates was inoculated to nutrient broth and incubated for 48 h at 37° C. with shaking. The cells were washed with PBS pH 7.4 and centrifuged at 7000×g for 30 min. The bacterial pellet was heat killed at 75° C. for 10 min. The killed bacterial pellet was disrupted by pulsed mode sonicator for 3 min on ice. Subsequently, the cell suspension was centrifuged at 6108×g for 10 min and the supernatant containing whole antigenic extract was freeze-dried with 5% sucrose as a cryoprotectant. The protein concentration was estimated using micro BCA protein assay kit.

2.5. Preparation of OMPs and Flagellar Loaded and Flagellar Coated-PNPs (OMPs-F-PNPs)

*Salmonella* OMPs and flagellar loaded and surface flagellar coated PNPs (OMPs-F-PNPs) were formulated by a solvent displacement method as described previously [22] with some modifications. Briefly, 2.5 mg each of both OMPs and flagellar (or 5 mg of KAg) were dispersed in 3 mL of acetone, added into 100 mg of sonicated polyanhydride (Mw ~216,000, Sigma, MO) in dissolved in 2 mL acetone under magnetic stirring. Fifty microliter of SPAN® 80 (Sigma, MO) was added and the organic solution was magnetically stirred for 1 h at room temperature. The polymer was desolvated by addition of 7 mL absolute ethanol followed by 3 mL deionized water containing 2.5 mg of flagellar protein, and magnetic stirring was continued for another 1 h to evaporate the organic solvents.

The formulated nanoparticle suspension with surface adsorbed flagellar was cross-linked by incubation with 100 μg 1,3-diaminopropane for 5 min. OMPs-F-PNPs or KAg—F-PNPs were collected by centrifugation at 27,000×g for 20 min and freeze-dried with 5% sucrose as a cryoprotectant. Empty PNPs and PNPs surface coated with F protein (PNPs-F) and without OMPs were similarly prepared. The PNPs and PNPs-F were tagged with fluorescent dye by incubating with 1.25 mg RITC (Sigma, MO) for 5 min. The fluorescent tagged nanoparticles were obtained by centrifugation at 10,500×g for 10 min and freeze-dried with 5% sucrose. [22].

2.6. Preparation of OMPs and Flagellar Loaded and Flagellar Coated-CS NPs (OMPs-F-CS NPs)

The OMPs-F-CS NPs were prepared by an ionic gelation method as described previously [47] with some modifications. Briefly, nanoparticles were formed by intra- and inter-molecular crosslinking between positively charged chitosan and negatively charged sodium tripolyphosphate (TPP). The 1% (w/v) low molecular weight chitosan (Sigma, MO) solution was prepared by slowly dissolving chitosan in an aqueous solution of 4% acetic acid under magnetic stirring until the solution became transparent. The solution was sonicated and the pH was adjusted to 4.3 and filtered through a 0.44 μm syringe filter. To prepare OMPs-F-CS NPs, 5 mL of 1% chitosan solution was added to 5 mL of deionized water and incubated with 2.5 mg each of both OMPs and flagellar in 1 mL of PBS pH 7.4. Subsequently, 2.5 mL of 1% (w/v) TPP (Sigma, MO) in 2.5 mL deionized water was added into the solution and subjected to magnetic stirring at room temperature. For surface conjugation, 2.5 mg of flagellar protein in PBS was added to the particles and the electrostatic interaction helps in surface labeling of flagellar on CS NPs, and centrifuged at 10,000 rpm for 10 min to collect OMPs-F-CS NPs.

For in vivo particle tracking study in the ileum of chicken, the empty or surface F-protein coated CS NPs (CS NPs-F) were prepared as mentioned above method without the carrier protein using cargo protein, fluorescently labelled by incubation with 1.25 mg Rhodamine B isothiocyanate (RITC) (Sigma, MO) for 5 min as described previously [22]. The formulated nanoparticles were separated by centrifugation at 10,500×g for 10 min and freeze-dried with 5% sucrose as a cryoprotectant.

In another experiment, CS polymer (mg/mL) and TPP (mg/mL) cross linker were used to formulate chitosan nanovaccine. In brief, 50 mg of 1% chitosan solution was added to 50 mL of deionized water and incubated with 2.5 mg each of both OMPs and flagellar (or 5 mg of KAg) in 1 mL of PBS pH 7.4. Subsequently, 12.5 mg of 1% (w/v) TPP (Sigma, MO) in 25 mL deionized water was added into the solution and subjected to magnetic stirring at room temperature. For surface conjugation, 2.5 mg of flagellar protein in PBS was added to the particles and the electrostatic interaction helps in surface labeling of flagellar on CS NPs, and centrifuged at 10,000 rpm for 30 min to collect OMPs-F-CS NPs.

2.7. Scanning Electron Microscope Analyses of OMPs-F-PNPs and OMPs-F-CS NPs

The size and morphological characteristics of the isolated *Salmonella* OMPs and flagellar, empty and vaccine cargo loaded nanoparticles formulations were visualized under the cold field emission HITACHI® S-4700 scanning electron microscope (SEM). The samples were prepared on aluminum stubs and coated with platinum prior to examination. The OMPs-F-PNPs mean particle size and zeta potential distribution, CS NPs and OMPs-F-CS NPs mean particle size distribution was evaluated using Zetasizer Nano ZS90 (Malvern Panalytical).

2.8. Encapsulation Efficiency

The OMPs-F-PNPs were digested in 0.1 M NaOH for 4 h at 3TC, sonicated and dispersed in PBS. The amount of protein released was measured using the micro BCA protein assay kit [35]. The protein loading efficiency was estimated as a difference between the initial amount added and the amount found after digesting the particles. The nanoparticles containing surface bounded protein was also similarly estimated by subtracting the cargo loaded with or without surface coated protein.

The OMPs-F-CS NPs protein loading efficiency was estimated by an indirect method by determining difference between the protein amount found in the formulation supernatant and the initial amount used. The nanoparticles surface bounded protein was estimated similarly by subtracting the cargo loaded with or without surface coated protein.

2.9. Hemolysis Assay

Fresh 2 mL chicken blood in EDTA collected in a sterile tube was centrifuged at 1,000×g for 10 min and collected the red blood cells (RBCs). The RBCs were washed 2-3 times using sterile PBS and suspended in 3 mL PBS, 100 µL of RBCs were treated with 250-1000 µg of empty PNPs, or CS NPs, or as a positive and negative control with TRITON® x-100 and PBS, respectively. Treated RBCs were incubated at 37° C. for 1 h, centrifuged at 12000×g for 10 min and the supernatant containing released hemoglobin was measured at OD 575 nm using an enzyme-linked immunosorbent assay (ELISA) plate reader (Spectramax plus 384, Molecular Devices, CA). The percentage (%) of hemolysis was calculated by the formula: sample treatment optical density (OD)-negative control OD/positive control OD-negative control OD×100 [48]. The treated residual RBCs were suspended and morphological changes were observed under a microscopy at 4× magnification (Invitrogen™ EVOS™ FL Cell Imaging System, WA).

2.10. pH Stability Analyses

The pH stability of empty PNPs and empty CS NPs were evaluated by measuring the turbidity of nanoparticles suspension in different acidic and alkaline pH conditions over a period of 3 h as described previously [35]. Briefly, 6 mg of nanoparticles (empty PNPs or empty CS NPs) were suspended in 4 mL of different pH solutions (3.5, 4, 4.5, 5.5, 6.5 and 7.4) and at stipulated time intervals 100 µL aliquots were taken to measure turbidity at OD 405 nm using a spectrophotometer. All measurements were performed in duplicate and the results were expressed in percent reduction in turbidity at different pH over a period of time. The percent reduction was calculated by: initial OD−different time point OD/initial OD×100.

2.11. In Vivo Bioadhesion Study

The GI tract mucosal adhesive property of RBITC-labelled PNPs-F and CS NPs-F were analyzed in chicken ileum tissue by fluorescence microscopy [36]. For in vivo analyses, healthy layer chickens were orally treated with normal saline, 0.6 mg of RBITC dye solution, 50 mg of RBITC labelled PNPs-F or 25 mg of RBITC labelled CS NPs-F, respectively for 4 h. Animals were sacrificed after 4 h, 1 cm of ileum was removed, processed in 20% sucrose solution for 4 h and washed using PBS. The ileum tissue was processed using the Tissue-Tek O.C.T compound (Sakura Finetek, CA) and frozen in −80° C. The frozen tissue samples were cut into 5 µm section in a cryostat (Leica CM1510S, IL), mounted on poly-L-lysine precoated slides, stained with DAPI and visualized under a cell imaging microscope (Invitrogen™ EVOS™ FL Cell Imaging System, WA) at 2× magnification.

2.12. Experimental Design, Vaccination Schedule, Bacterial Challenge and Collection of Samples Specific pathogen free one day old layer chickens were received at the OARDC animal house facility and used in the present study. All the hens had ad libitum access to water and antibiotic free food. At 6 weeks age chickens were randomly divided into five experimental groups in cages in separate isolation rooms (Table. 1). Using an oral gavage needle chickens were orally vaccinated with soluble OMPs (50 µg)+flagellar (50 µg) in sterile PBS or equivalent protein loaded OMPs-F-PNPs or OMPs-F-CS NPs suspension in 1 mL of sterile PBS. The same dose and route of delivery was repeated during the $2^{nd}$ and $3^{rd}$ vaccinations at 3 weeks interval.

The nalidixic acid-resistant *S. enteritidis* pure culture (Phage type 13a) 100 µL glycerol stock was grown in 10 mL tryptic soy broth (TSB) at 37° C. without shaking. After 8 h of incubation, 100 µL of the bacterial suspension was transferred into 10 mL of fresh TSB and incubated overnight at 37° C. One mL of the bacterial suspension was transferred into 100 mL of fresh TSB and incubated at 37° C. until the culture OD reaches 1.1. The bacteria was washed three times with PBS, serially diluted and plated on Xylose Lactose Tergitol™ 4 (XLT4) agar plate and counted the colony forming units (CFU). Birds were challenged at day post-vaccination (DPV) 63 with 1 mL bacterial suspension containing $1 \times 10^9$ CFU in PBS after 7 to 8 h fasting using an oral gavage needle. Chickens were euthanized at day post-challenge (DPC) 10. Birds were maintained, sample collection and euthanasia procedures were strictly followed as per the Standards of the Institutional Laboratory Animal Care and Use Committee, and Ethics for Animal Experiments at The Ohio State University (Protocol number: 2016A00000060).

Samples of blood and cloacal swabs in 0.5 mL PBS were collected at DPV 0, 21, 42, 63 and 73 (DPC 10). Serum was separated and cloacal swab samples were vortexed and centrifuged at 3000×g for 10 min, aliquots were stored at −80° C. On day of necropsy (DPC 10), 10 cm ileum and trachea were collected in 2 mL PBS, cut into small pieces, vortexed and centrifuged at 3000×g for 10 min and aliquots of supernatant was stored at −80° C. The bile samples were collected from gallbladder using an insulin syringe and aliquots were stored at −80° C. The entire cecum was collected and stored at −80° C. Blood was collected in sterile EDTA tubes for isolation of peripheral blood mononuclear cells (PBMC) and spleen tissue was collected in 2 mL RPMI medium (GE Healthcare Life Sciences, UT) enriched with 10% fetal bovine serum (Sigma), antibiotic-antimycotic (Gibco), sodium pyruvate, 1M HEPES, MEM NEAA and 2-mercaptoethanol, hereafter named as E-RPMI.

2.13. Analyses of Antibody Response

Pre- and post-challenge chicken IgG and IgA antibody response in serum, cloacal swab, bile, small intestinal wash and tracheal wash samples were determined by ELISA. Flat bottom high binding 96 well plates (Greiner Bio-one, NC) were coated with pre-titrated amount of OMPs (2 µg/mL or 7.5 µg/mL for IgG or IgA ELISA, respectively) in 0.05 M sodium carbonate-bicarbonate buffer pH 9.6 and incubated overnight at 4° C. Plates washed three times and blocked with 5% (w/v) skim milk powder in PBS TWEEN®-20 (0.05%) (PBST) for 1 h at room temperature. Plates were washed three times in PBST and 50 µL/well in duplicate pre-diluted serum and bile samples in 2.5% skim milk powder or undiluted cloacal swab, small intestinal wash and tracheal wash samples were added to respective marked wells and incubated for 2 h at room temperature. Plates were washed three times and 50 µL/well of goat anti-chicken IgG conjugated HRP (Southern Biotech, AL) (1:10,000 in 2.5% skim milk powder in PBST) or goat anti-chicken IgA conjugated HRP (Gallus Immunotech, NC) (1:3000 in 2.5% skim milk powder in PBST) secondary antibodies were added and incubated for 2 h at room temperature. Plates were washed three times and 50 µl/well of TMB peroxidase substrate (1:1 mixture of TMB peroxidase substrate and TMB peroxidase substrate solution B) (KPL, MD) was added and the reaction was stopped after 10 to 20 min by adding 1 M phosphoric acid and OD was measured at 450 nm using the ELISA plate reader. The corrected OD was obtained by subtracting different treatment group OD from blank control OD.

Interferon-gamma (IFN-γ) levels in serum samples collected at DPC 10 were determined analyzed with by using a commercial kit (Cytoset™ Chicken IFN-γ ELISA based kit, Invitrogen, USA).

2.14. Lymphocyte Proliferation Assay

PBMC was isolated by using FICOLL®-paque plus (GE Healthcare, PA) as per the manufacture's protocol with slight modifications. Briefly, blood was diluted in PBS (1:1 ratio) and an equal volume of FICOLL®-paque plus solution was added and centrifuged at 450×g for 25 min at 20° C. with breaks on. Lymphocytes at the cells interface was collected, washed two times in PBS and suspended in E-RPMI medium. Splenocytes were isolated by teasing spleen tissue through a cell strainer using PBS and an equal volume of FICOLL®-paque plus solution was added and centrifuged at 450×g for 30 min at 4° C. with breaks on. Splenocytes at the interface were collected, washed two times with PBS and cells were suspended in E-RPMI medium.

In lymphocytes proliferation assay, PBMC and splenocytes 1×10$^6$ cells/well suspended in E-RPMI medium in triplicate wells were seeded in a 96 well flat bottom plate (Greiner bio-one, NC) in 100 µL volume. Cells were restimulated with OMPs (5 µg/mL) in 100 µL E-RPMI medium and incubated for 72 h at 39° C. in a 5% $CO_2$ incubator. After incubation 100 µL supernatant was collected, 20 µL of MTS+PMS solution was added into cells and incubated for 4 h at 37° C. in a 5% $CO_2$ incubator. The OD was taken at 490 nm by the ELISA plate reader. Stimulation index (SI) was calculated by dividing OD of stimulated cells from OD of unstimulated control cells of the same chicken, and the average SI value of 8 to 10 chickens of each group was compared among other groups.

2.15. Reverse Transcriptase Quantitative PCR (RT-qPCR) Analyses

Total RNA was extracted by using the TRIzol reagent (Invitrogen) in the cecal tonsils of chickens. The isolated RNA was dissolved in Tris-EDTA (pH 7.5) buffer and the concentration was determined by using NanoDrop™ 2000c Spectrophotometer (Thermo Fisher Scientific). The cDNA synthesis was achieved with 1 µg of total RNA using the QuantiTect Reverse Transcription Kit (QIAGEN) according to the manufacturer's instructions. The mRNA expression of TLR-2, TLR-4, cytokines IFN-γ, TGF-ß, IL-4, IL-1ß, and iNOS, and the house keeping gene β-actin were analyzed by real-time quantification (7500 Real-Time PCR System, Applied Biosystems, CA) using the iQ™ SYBR® Green Supermix (Bio-Rad, CA). Target gene expression levels were normalized to β-actin and the fold change was determined by dividing the results of the treated samples and untreated control samples.

2.16. Bacteriology

Cecum (0.5 g) was homogenized in 2× concentration of peptone water and incubated for 12 h at 37° C. for initial enrichment of the bacteria. Subsequently, streaked on naladixic acid antibiotic containing XLT plate and incubated for 24 h at 37° C. The black colored *S. enteritidis* colonies in plates were qualitatively confirmed as *salmonella* by following the standard methods [49, 50]

2.17. Statistical Analyses

Data are represented as the mean±standard error of mean (SEM) of 8 to 10 chickens. Date were examined by non-parametric Kruskal-Wallis test in Graphpad Prism 5 (Graphpad software, CA), followed by p value difference between the groups were determined by Mann-Whitney test using the Graphpad Prism 5 (Graphpad software, CA). A p value less than 0.05 was considered statistically significant.

3. RESULTS 3.1. Characterization of *Salmonella* Vaccine Antigens and Nanoparticles Vaccines The morphology of isolated *Salmonella* antigens, OMPs and flagellar protein, was determined by SEM analysis. The results revealed both OMPs and flagellar are both in spherical and irregular shapes and aggregated in the form of a matrix (FIGS. 1 A&B). Complex proteins present in OMPs enriched extract of *S. enteritidis* have been reported [51]. SDS-PAGE analysis of isolated OMPs revealed a complex electrophoretic profile containing greater than 12 different proteins ranging from 14 to 70 kDa. Among them the major well characterized antigenic proteins are having the molecular weight 22, 23, 28, 34, 36, 45, 46, 55, 65, 68 and 70 kDa (FIG. 1 C). The flagellar enriched extract was having the flagella specific proteins based on the molecular weight [52]: FlgD 28 kDa, FlgL 35 kDa, FlgE 42 kDa, FlgD 50 kDa, FlgK 58 kDa and also surface appendages protein SEF21 21 kDa (FIG. 1 C).

Figure 2A:
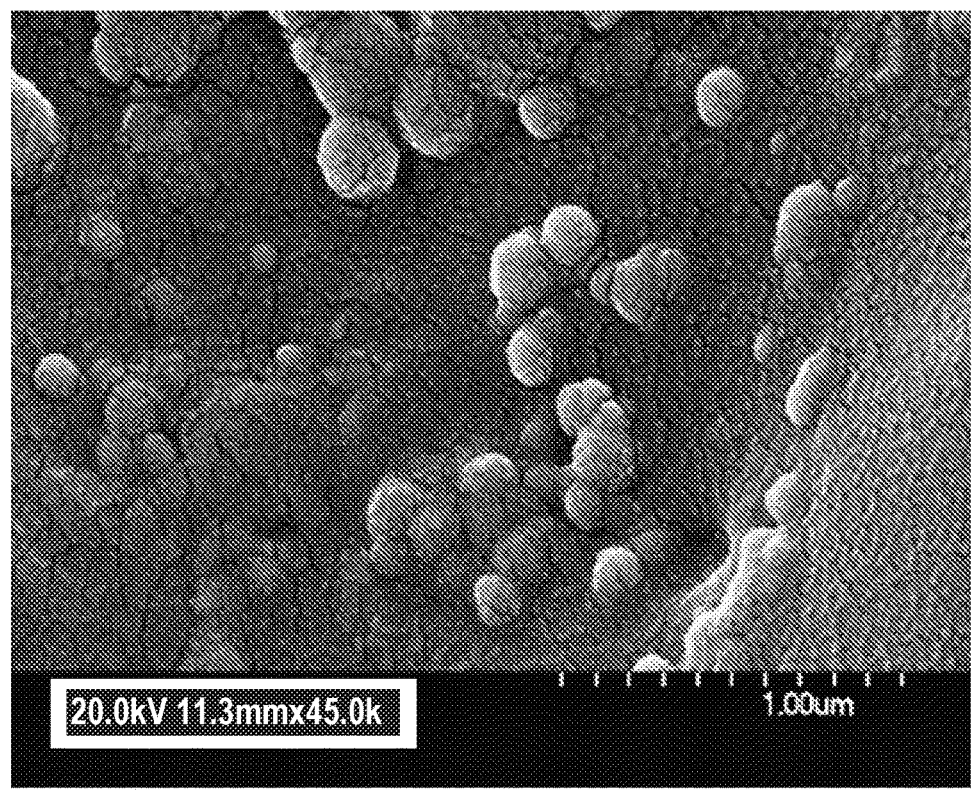
FIGS. 2A-2C. Physicochemical characterization of polyanhydride nanoparticles (PNPs). SEM analysis of OMPs-F-PNPs (FIG. 2A); OMPs-F-PNPs mean particle size distribution (FIG. 2B); Zeta potential distribution by Zetasizer analyses (FIG. 2C).
Figure 2B:
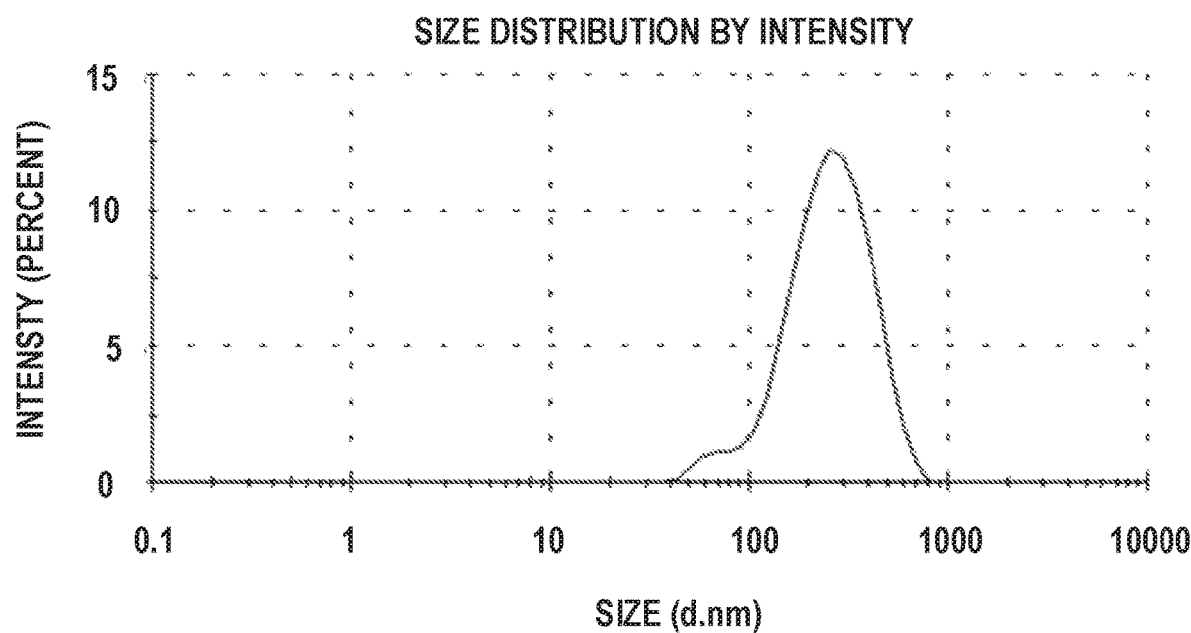
Figure 2C:
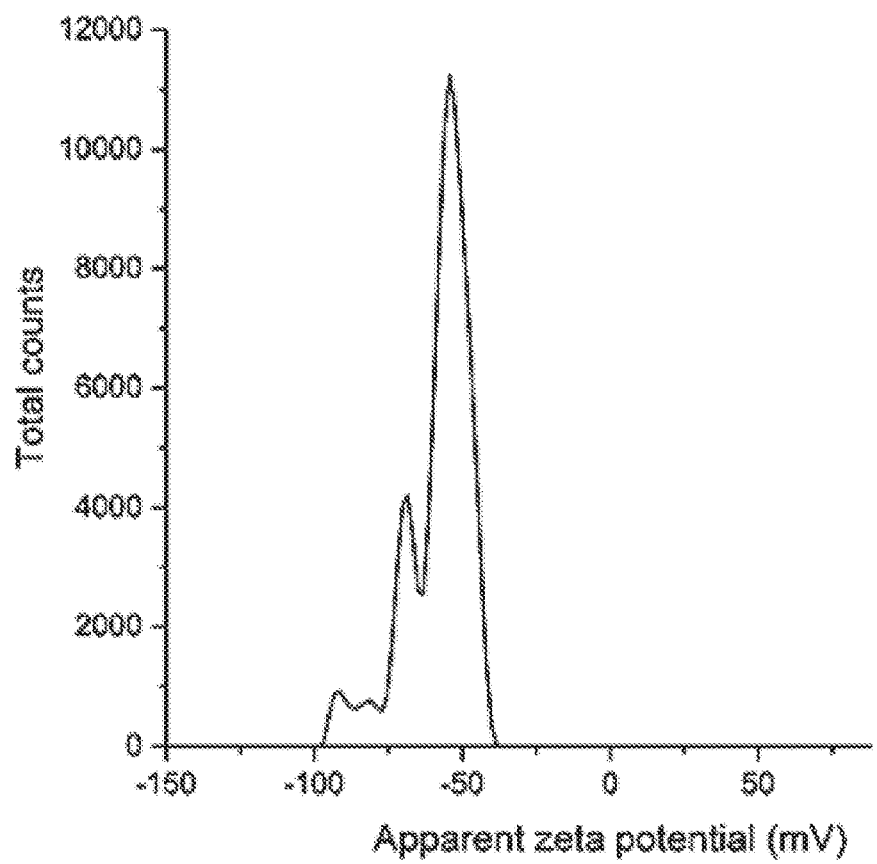
Figure 3A:
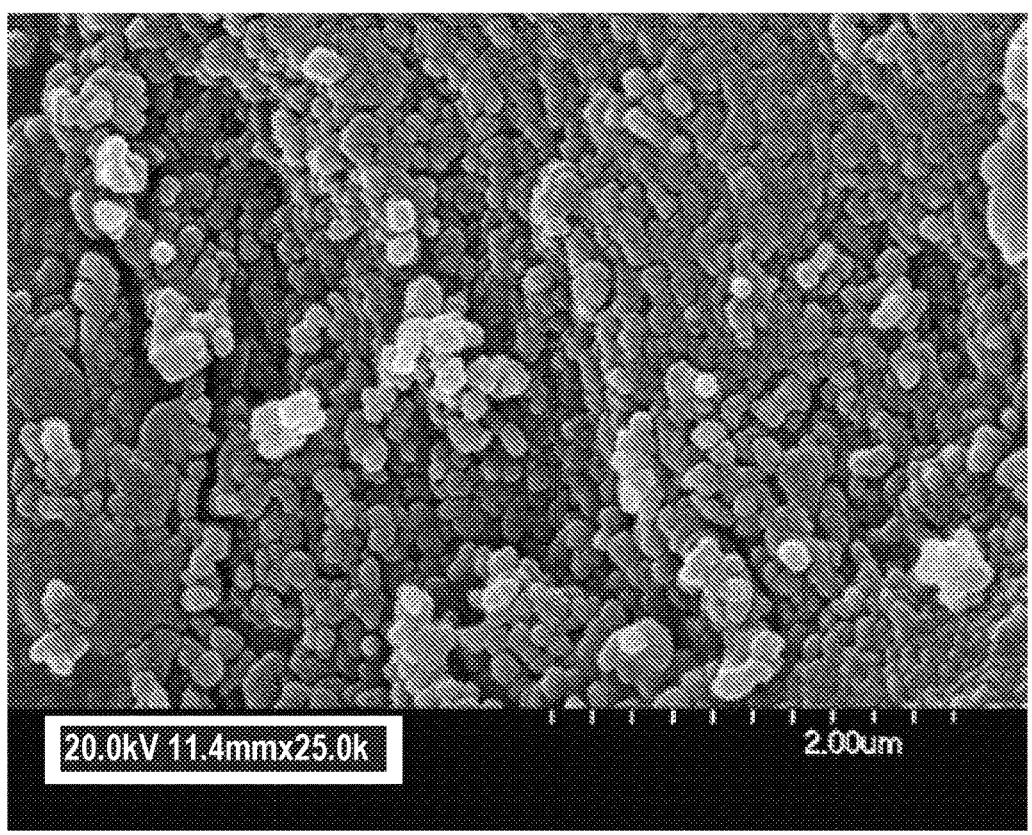
FIGS. 3A-3D. Physicochemical characterization of chitosan nanoparticles (CS NPs). SEM analysis of (FIG. 3A) empty CS NPs and (FIG. 3B) OMPs-F-CS NPs; Mean particle size distribution of (FIG. 3C) empty CS NPs and (FIG. 3D) OMPs-F-CS NPs.
Figure 3B:
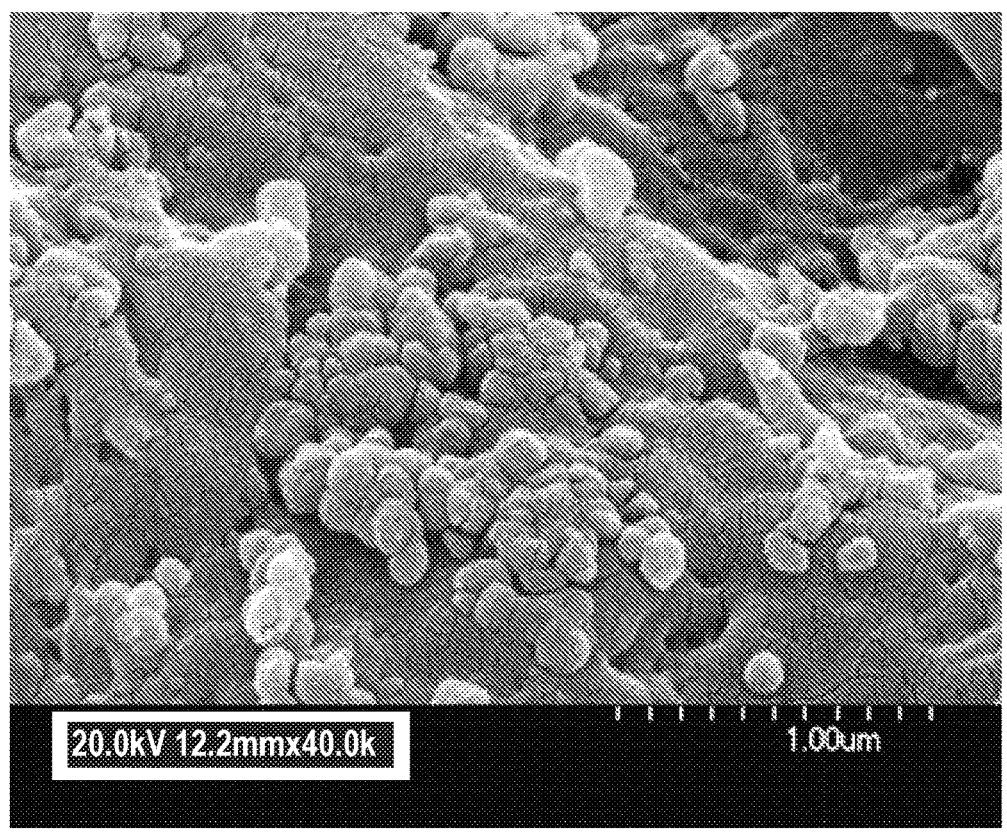
Figure 3C:
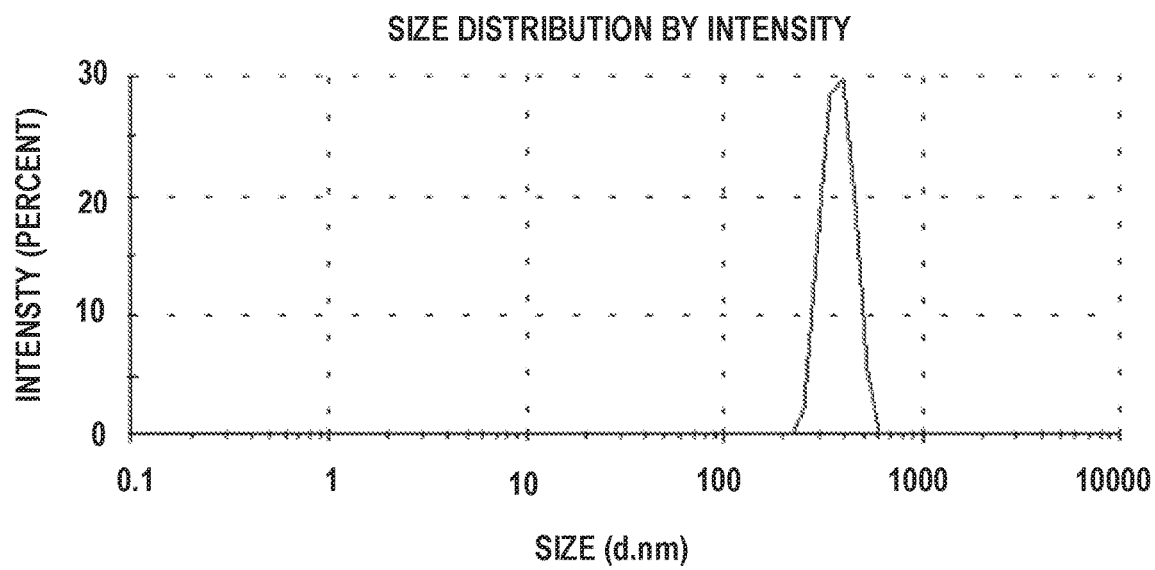
Figure 3D:
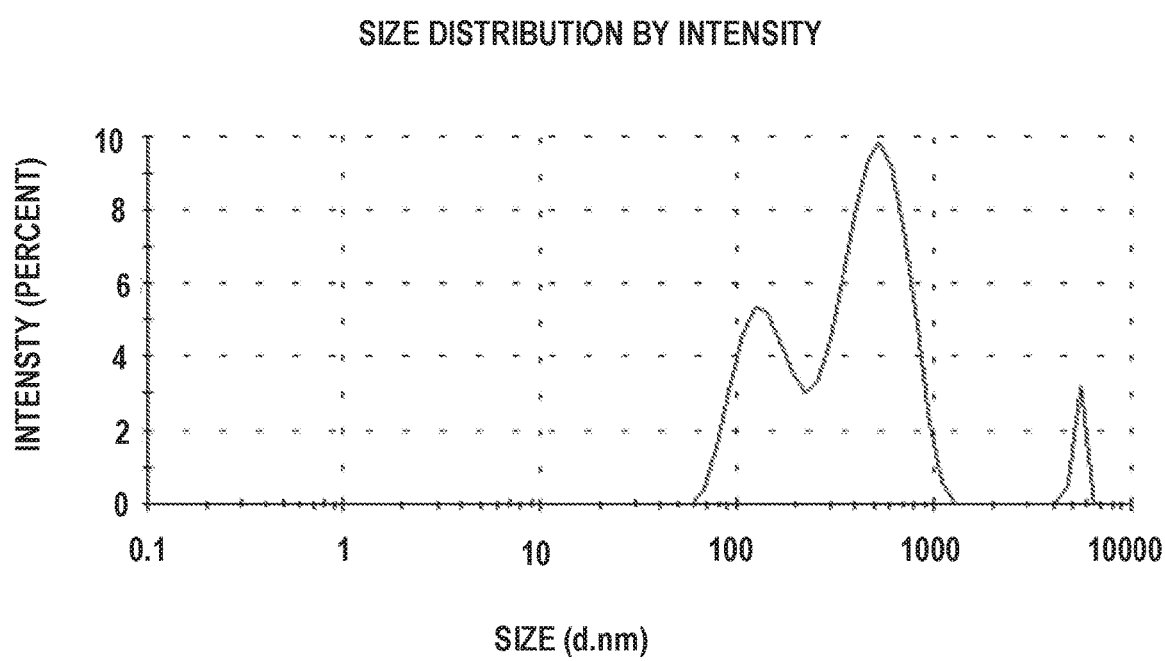

By using solvent displacement and ionic gelation methods, PNPs and CS NPs were formulated with the homogeneous size distribution, high antigen cargo loading efficiency. Moreover, without any chemical activation flagellar was coated on the surface of the polymeric nanoparticles. SEM analyses results showed formulated OMPs-F-PNPs were spherical in shape (FIG. 2A). The OMPs-F-PNPs mean particle size distribution was 215±5 nm with polydispersity index (PDI) of 0.2, negative average zeta potential charge of −38±4 mV (FIGS. 2B and C). Empty CS NPs and OMPs-F-CS NPs were spherical in shape and evenly distributed in the colloidal matrix without any aggregation (FIGS. 3A and 3B). CS NPs and OMPs-F-CS NPs had mean particle size distribution of 380 and 517 nm with PDI of 0.29 and 0.62, respectively under Zetasizer analyses (FIGS. 3C and D). Formulated OMPs-F-PNPs vaccine antigens encapsulation efficiency was 78% and surface conjugation efficiency was 25%. Similarly, the OMPs-F-CS NPs entrapment and surface conjugation efficiencies of antigens were 70% and 40%, respectively.

Figure 4A:
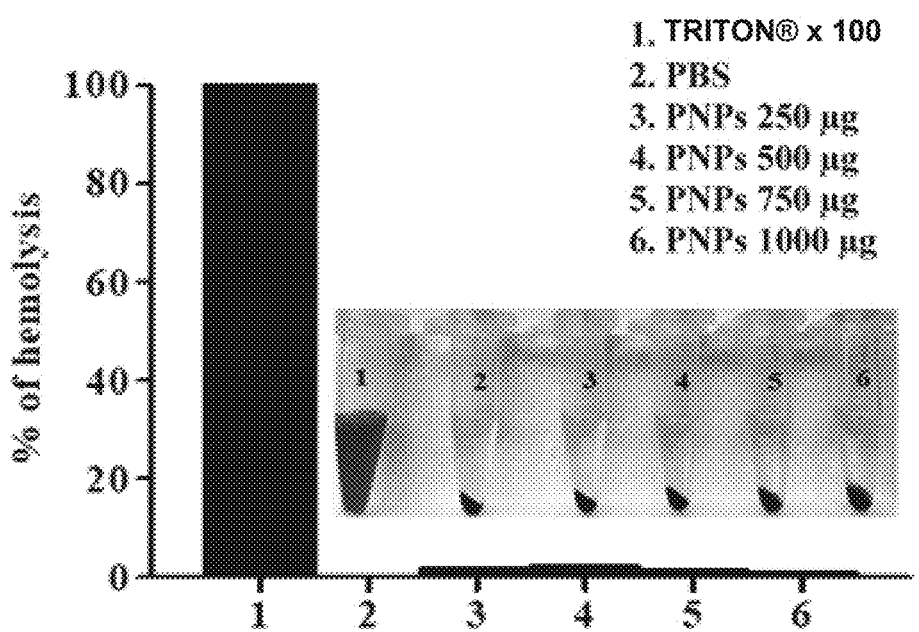
FIGS. 4A-4C. Biocompatibility and pH stability of PNPs.
Figure 4B:
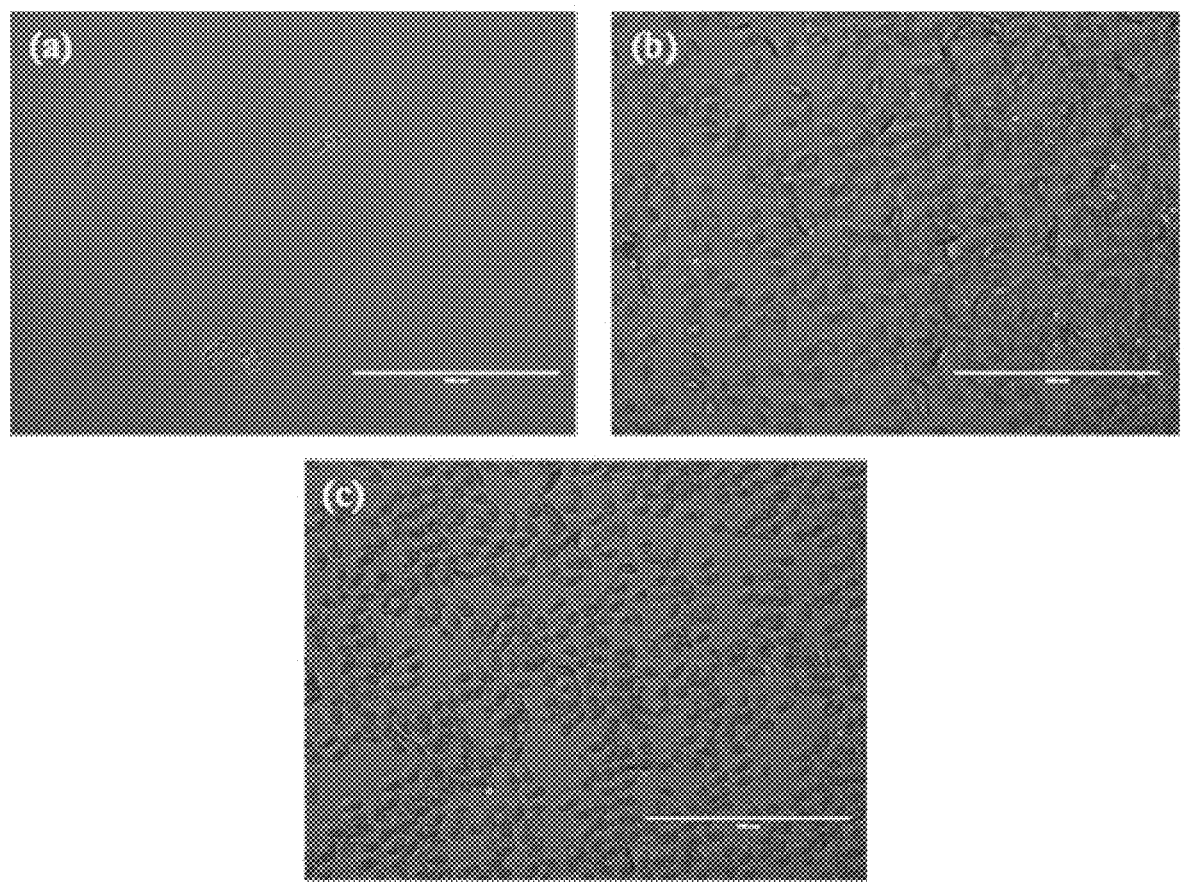
Figure 5A:
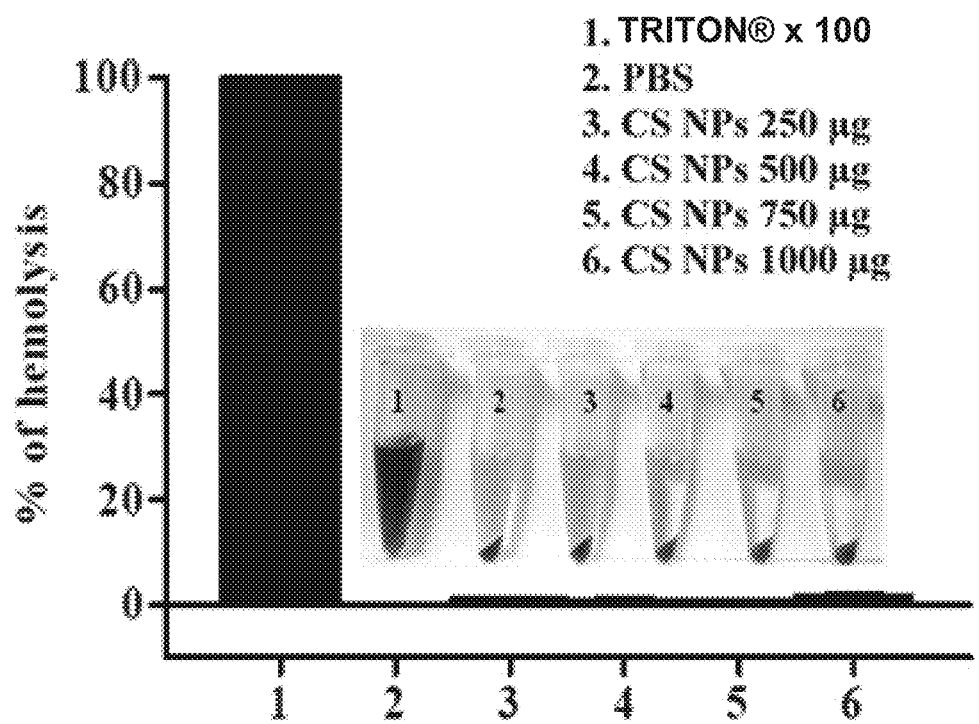
FIGS. 5A-5C. Biocompatibility and pH stability of CS NPs.
Figure 5B:
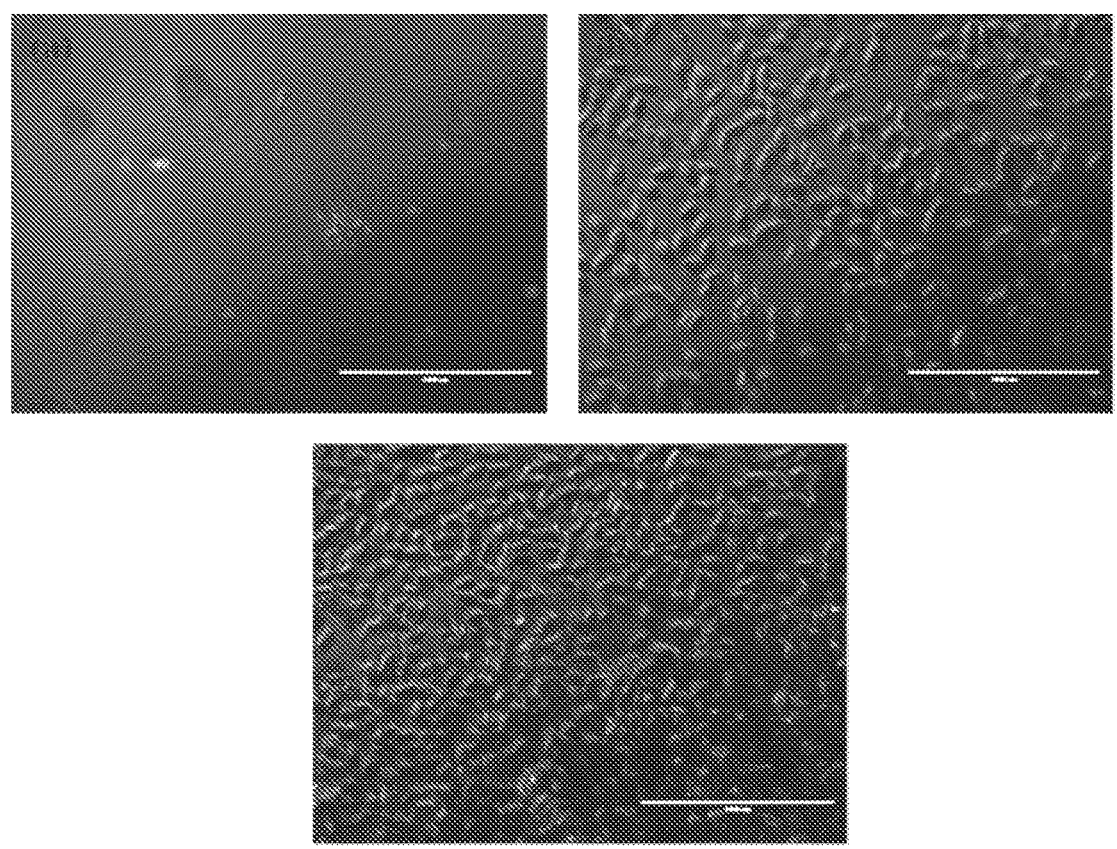

For biocompatibility analysis, hemolysis is one of the well accepted standard assays for estimating the toxicity of nanoparticles. The interaction between nanoparticles and RBCs membrane and the level of nanoparticles spreading on the RBCs is the way of checking nanoparticles mediated toxicity [48]. Formulated PNPs and CS NPs hemocompatibility was analyzed using chicken RBCs. The results showed that the PNPs and CS NPs did not induce lysis of RBCs even with 1000 µg concentration and the absorbance value was comparable to control PBS treated RBCs Whereas treatment with TRITON® x-100 lysed 100% of RBCs. (FIGS. 4A and 5A). Furthermore, nanoparticles interactions with chicken RBCs were confirmed by microscopy analysis. The results indicated absence any direct interaction of nanoparticles with RBCs, while TRITON®×100 interacted with RBCs and lysed most of the cells and formed membrane aggregates (FIGS. 4B and 5B).

Figure 4C:
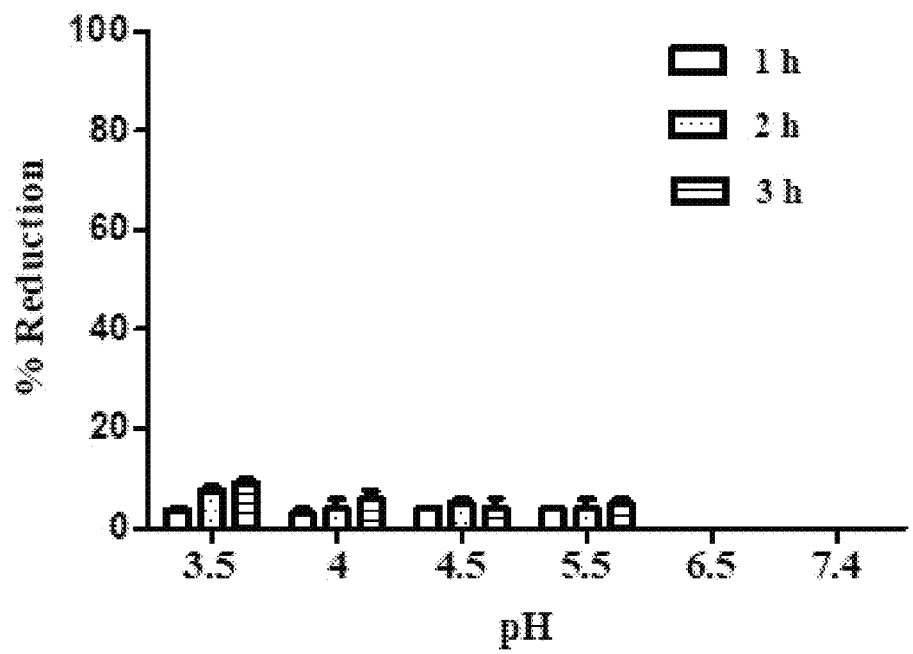
Figure 5C:
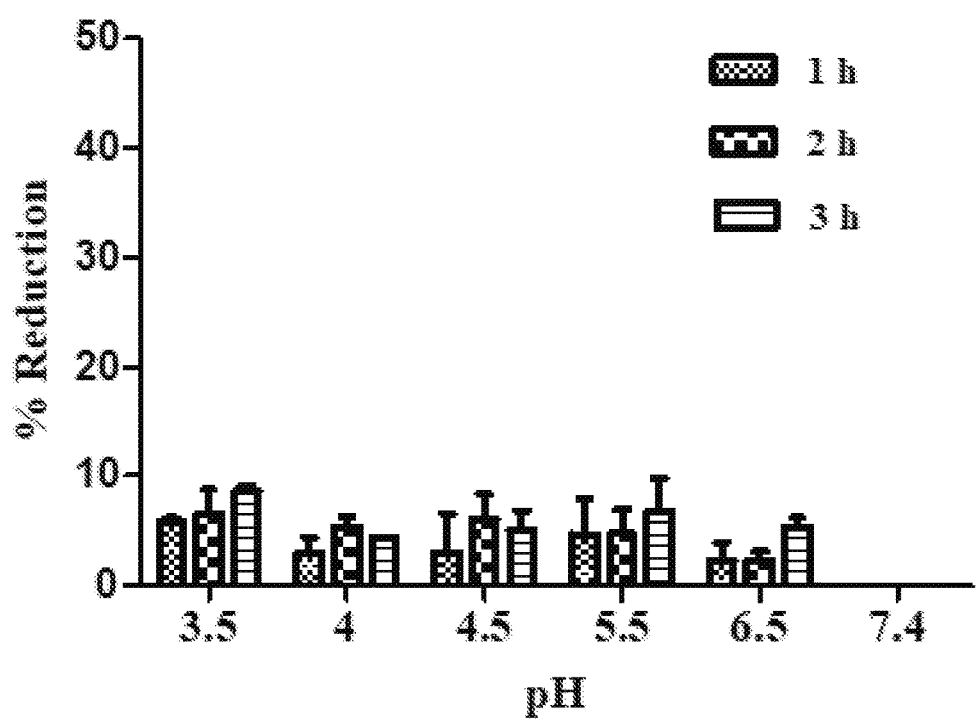

Nanoparticles form turbidity when dispersed in water or saline and turbidity reduction is due to instability, and it is an indirect way of checking nanoparticles stability in various physiological conditions over a period of time [35]. PNPs and CS NPs stability under different acidic to alkaline pH conditions was assessed by turbidity reduction assay. Upon incubation for 3 h both the nanoparticles exhibited less than 10% turbidity reduction in strong acidic environment (pH 3.5), and turbidity reduction gradually decreased with increasing pH. At pH 6.5 and above there was a complete absence of any turbidity reduction (FIGS. 4C and 5C).

3.2. In Vivo and Bioadhesion Study

Figure 6:
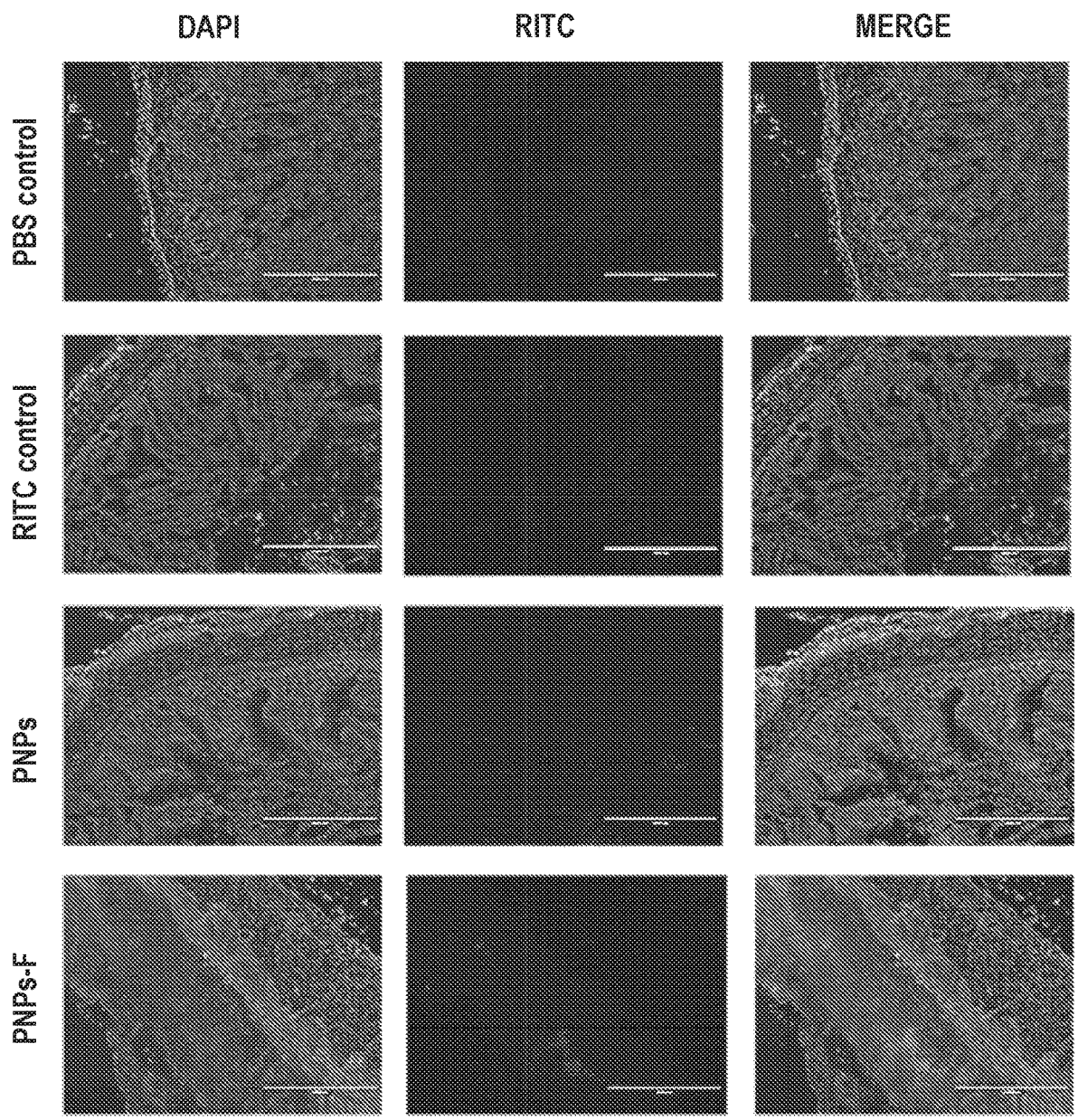
FIG. 6. In vivo mucoadhesive nature and uptake of fluorescent tagged PNPs-F in the ileum of chicken. Layer chickens were treated orally with PBS, RITC dye, RITC dye tagged PNPs or RITC dye tagged PNPs-F for 4 h. Chickens were euthanized and ileum harvested, washed, processed, fixed, sectioned, stained with DAPI and examined under a fluorescent microscope. The images were obtained at 2× objective and scale bar 2 mm.
Figure 7:
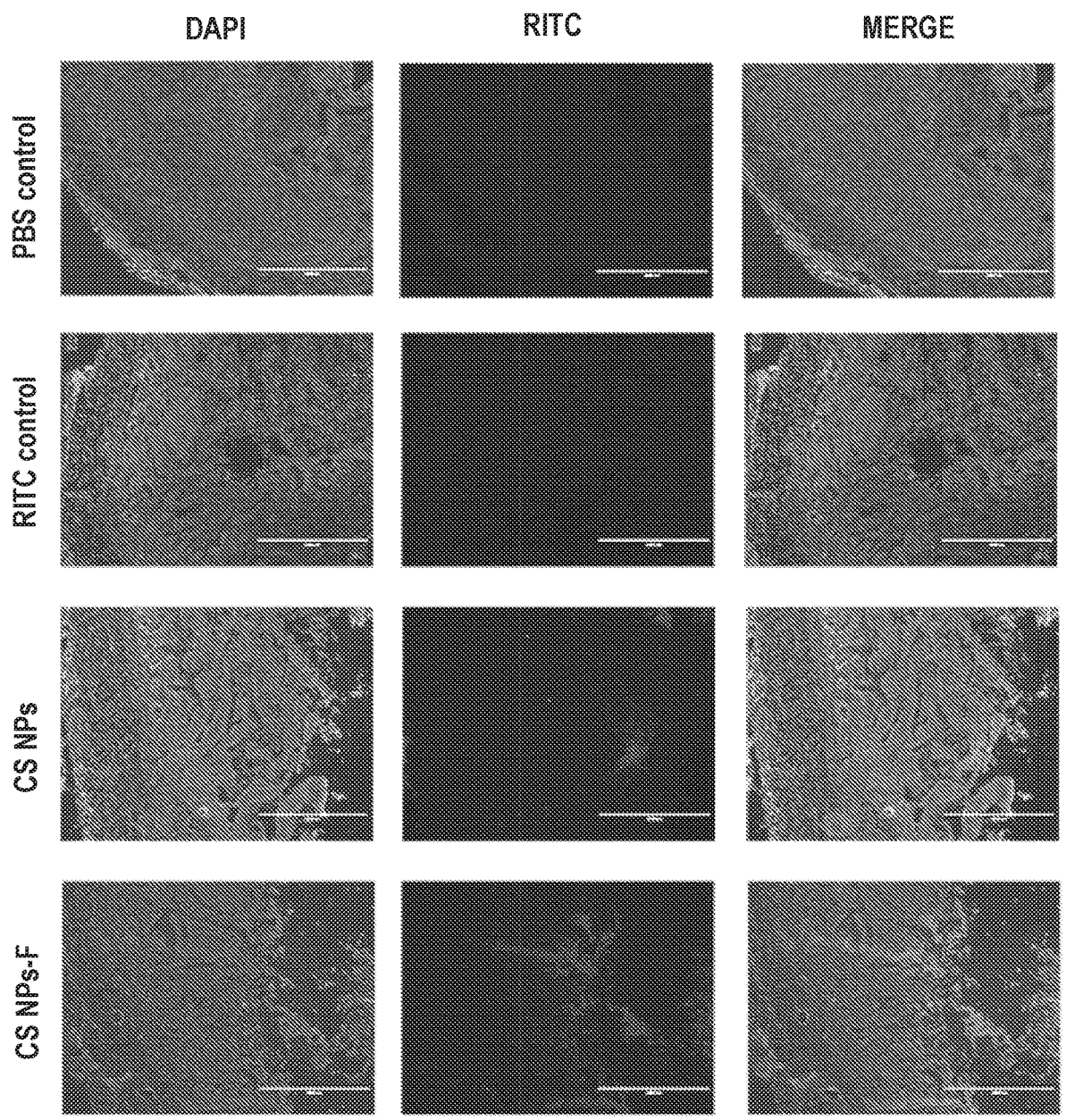
FIG. 7. In vivo analysis of penetration of CS NPs-F in the ileum mucosa of chickens. Layer chickens were orally treated with PBS or RITC dye, or RITC-labelled CS NPs or CS NPs-F. Birds were euthanized after 4 h and ileum was harvested, washed, fixed, sectioned, stained with DAPI and visualized under a fluorescent microscope. The pictures were taken at 2× objective and scale bar 2 mm.

Fluorescent labelled PNPs-F and CS NPs-F mucoadhesive nature in the ileum was evaluated by fluorescence microscopy. The in vivo treated ileum tissues were stained with the nuclear stain DAPI (Blue color), and nanoparticles were characterized in the red channel (RBITC labelled). PNPs-F and CS NPs-F were delivered orally found adhered to mucosal surface and uptaken by ileal PPs and lamina propria immune cells showed by in vivo studies, while nanoparticles without F-protein surface coating was poorly uptaken by PPs cells (FIG. 6 and FIG. 7). In the control groups there was no dateable RBITC signal.

Figure 8A:
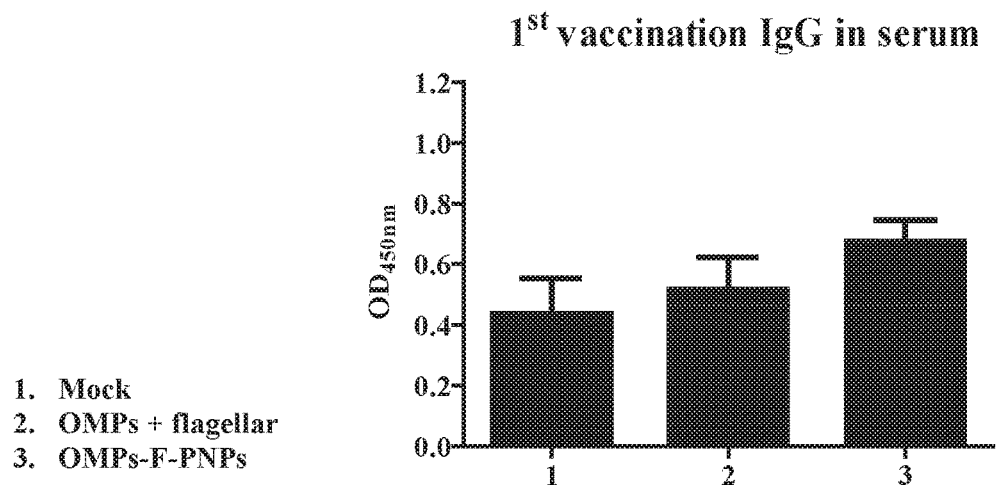
FIGS. 8A-8C. Pre-challenge OMPs-specific antibody response in chickens vaccinated orally with OMPs-F-PNPs. Layer chickens were inoculated orally three times at three 3-week intervals with mock saline (group 1) or OMPs and flagellar proteins (group 2) or the same amount of OMPs and flagellar proteins entrapped in NPs (OMPs-F-PNPs) (group 3). OMPs-specific IgG antibody response in serum (FIG. 8A-FIG. 8C) was analyzed by ELISA. Each bar is the mean±SEM of 8 to 10 chickens, and the data were analyzed by non-parametric Kruskal-Wallis test followed by p value differences in between the groups were determined by Mann-Whitney test. Asterisk refers to statistical difference between two indicated groups ($*P<0.05$ and $**P<0.01$).
Figure 8B:
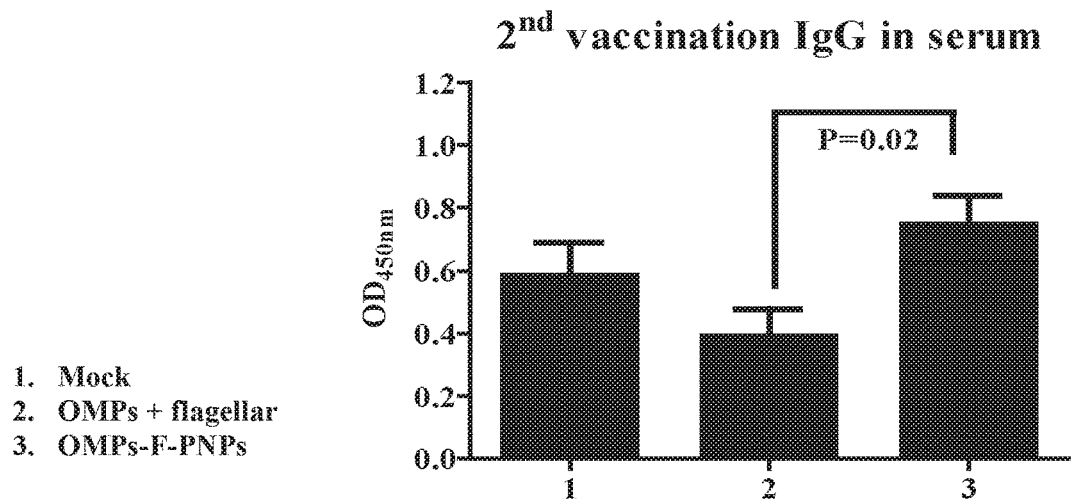
Figure 8C:
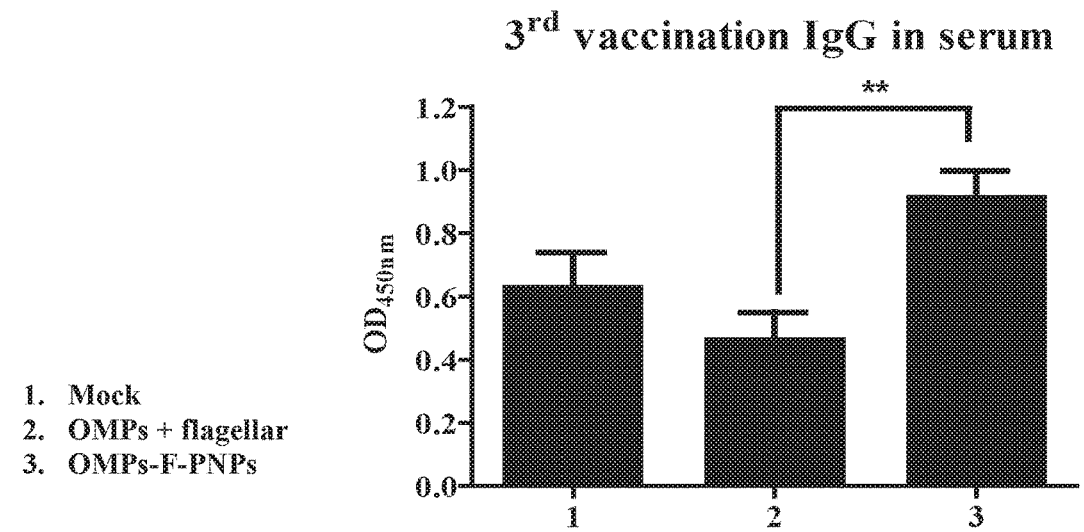
Figure 9A:
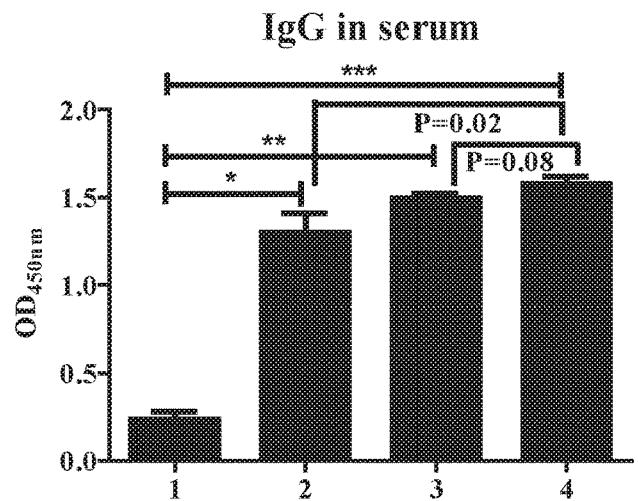
Figure 9B:
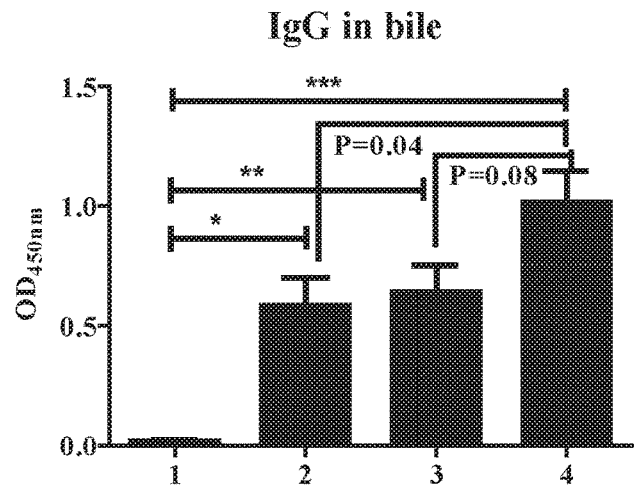
Figure 9C:
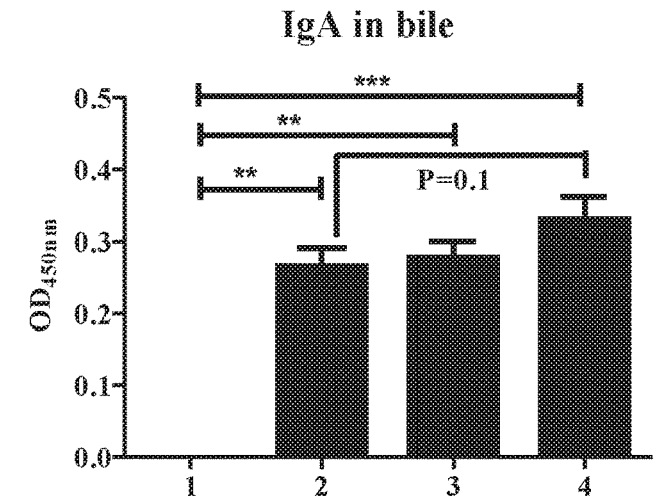
Figure 9D:
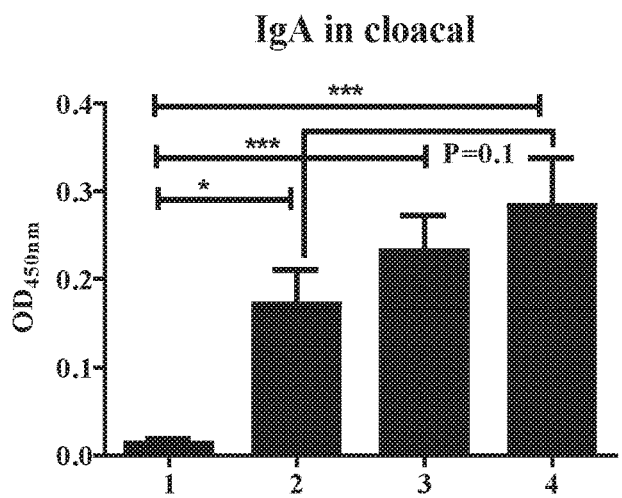
Figure 9E:
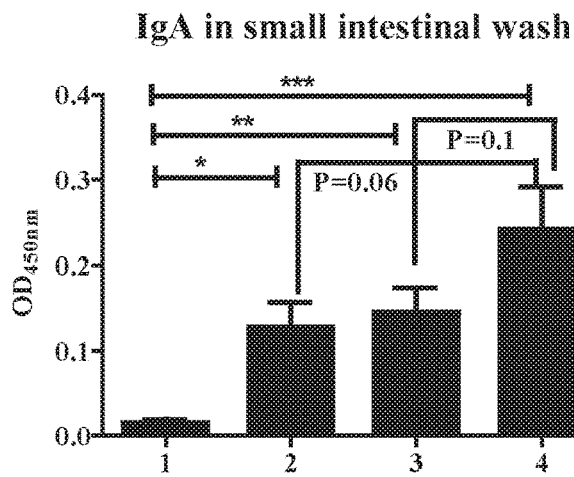
Figure 9F:
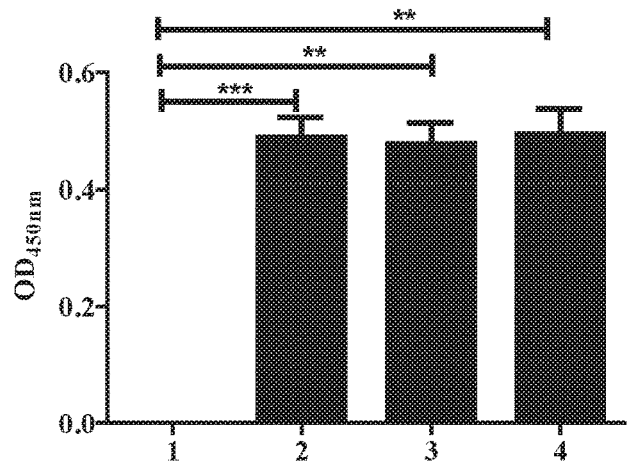

3.3. OMPs-F-PNPs and OMPs-F-CS NPs Induced OMPs Specific Humoral Immune Response For the nanovaccines received by the chickens at pre- and post-challenge, OMPs-specific IgG and IgA antibody responses were analyzed in serum, cloacal swab, bile, small intestine and tracheal wash samples. OMPs-specific IgG antibodies were detectable in serum after prime inoculation of OMPs-F-PNPs in chickens (FIG. 8A), and after 1st and 2nd booster vaccinations the antibody titers increased substantially compared to soluble antigens received group (FIG. 8B,C). After *S. enteritidis* challenge infection observed significantly increased OMPs-specific IgG and IgA antibody response in all the treatment groups compared to mock control (FIG. 9A-F). In particular, OMPs-F-PNPs vaccination significantly (P<0.0001) increased OMPs-specific IgG antibody response in serum and bile samples compared to mock group (FIG. 9A,B). OMPs-specific IgA antibody titers in OMPs-F-PNPs vaccinated chickens bile, cloacal swab, small intestine and tracheal wash samples were relatively at higher levels than control soluble antigens vaccinated group (FIG. 9C-F).

Figure 10A:
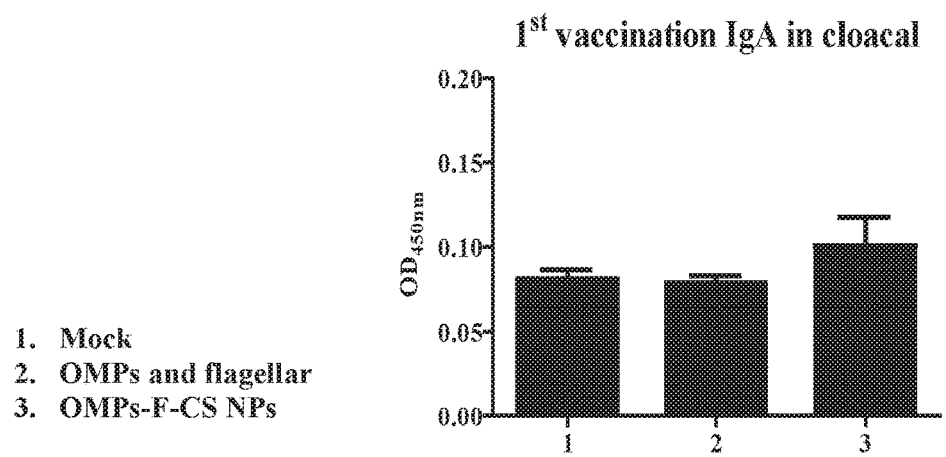
FIGS. 10A-10C. Pre-challenge OMPs-specific antibody response in chickens vaccinated orally with OMPs-F-CS NPs. Layer chickens were inoculated orally three times at three 3 week intervals with mock saline (group 1) or OMPs and flagellar proteins (group 2) or entrapped in NPs (OMPs-F-CS NPs) (group 3). OMPs-specific IgA antibody response in cloacal swabs (FIG. 10A-FIG. 10C) was analyzed by ELISA. Each bar is the mean±SEM of 8 to 10 chickens, and the data were analyzed by non-parametric Kruskal-Wallis test followed by p value differences in between the groups were determined by Mann-Whitney test. Asterisk refers to statistical difference between two indicated groups ($*P<0.05$ and $**P<0.001$).
Figure 10B:
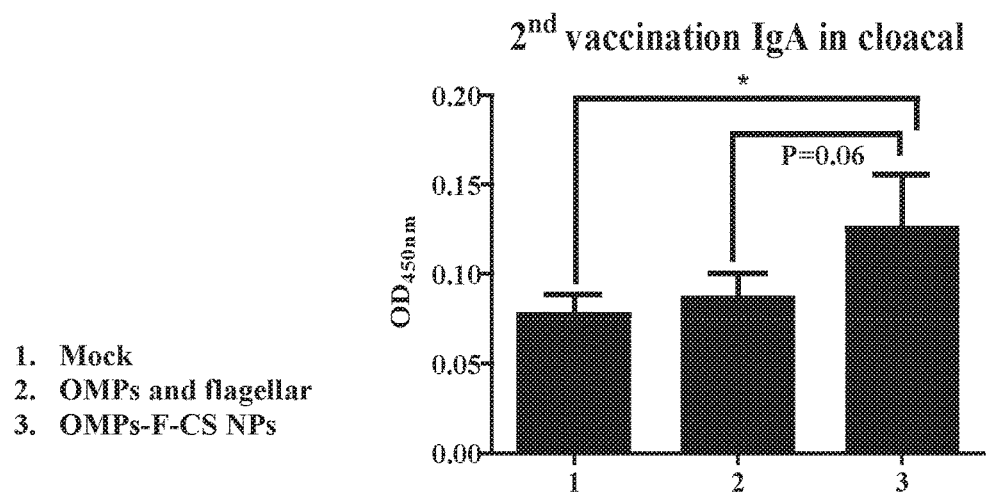
Figure 10C:
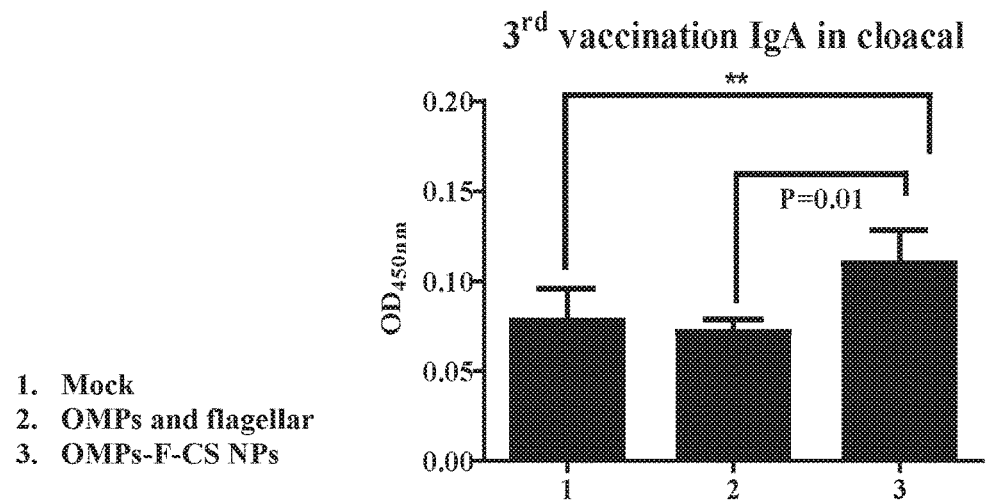
Figure 11A:
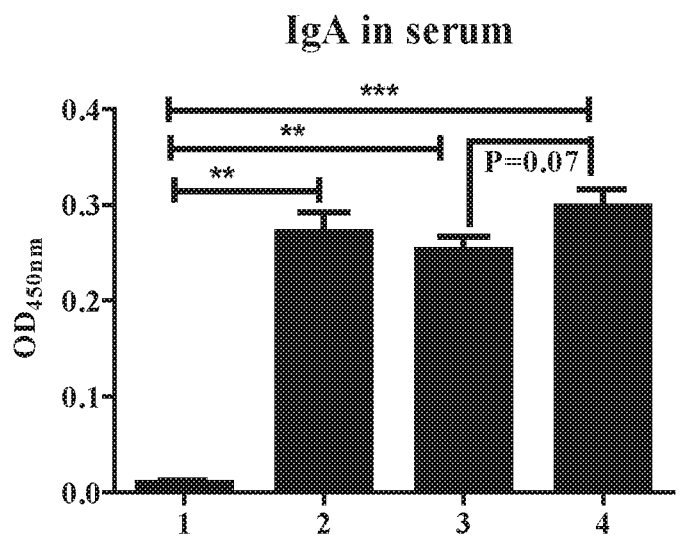
Figure 11B:
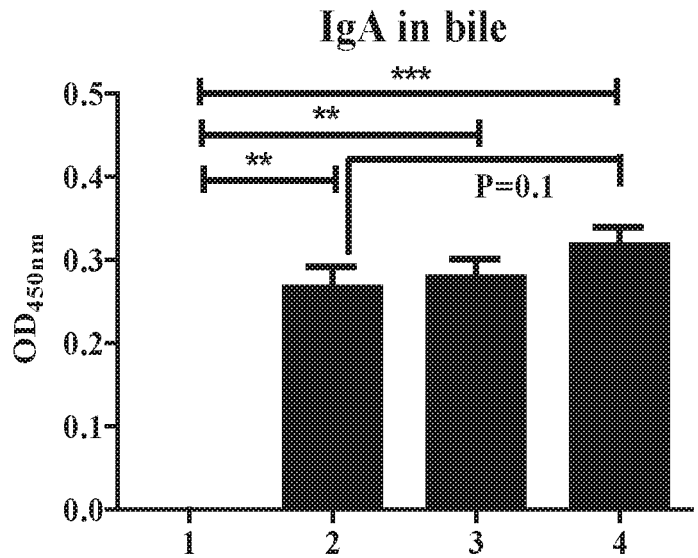
Figure 11C:
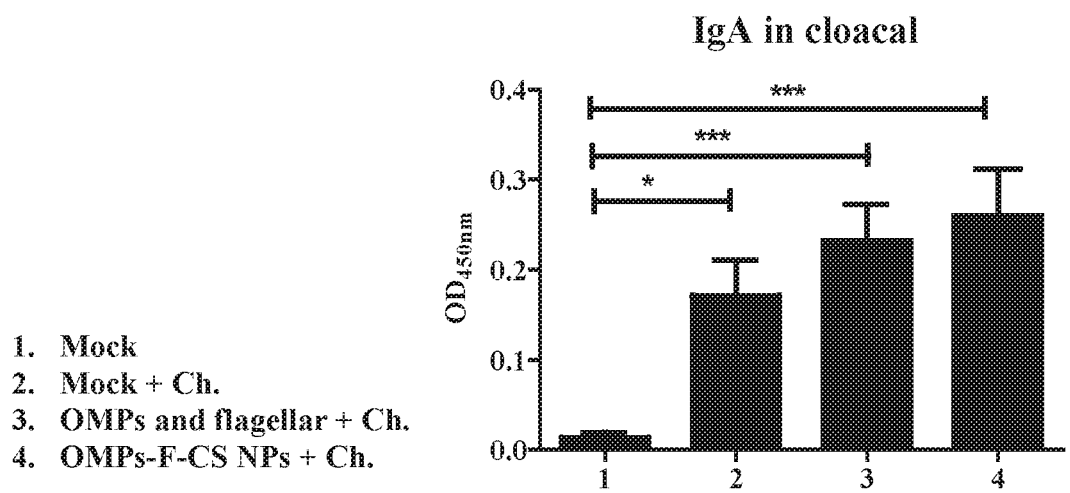
Figure 11D:
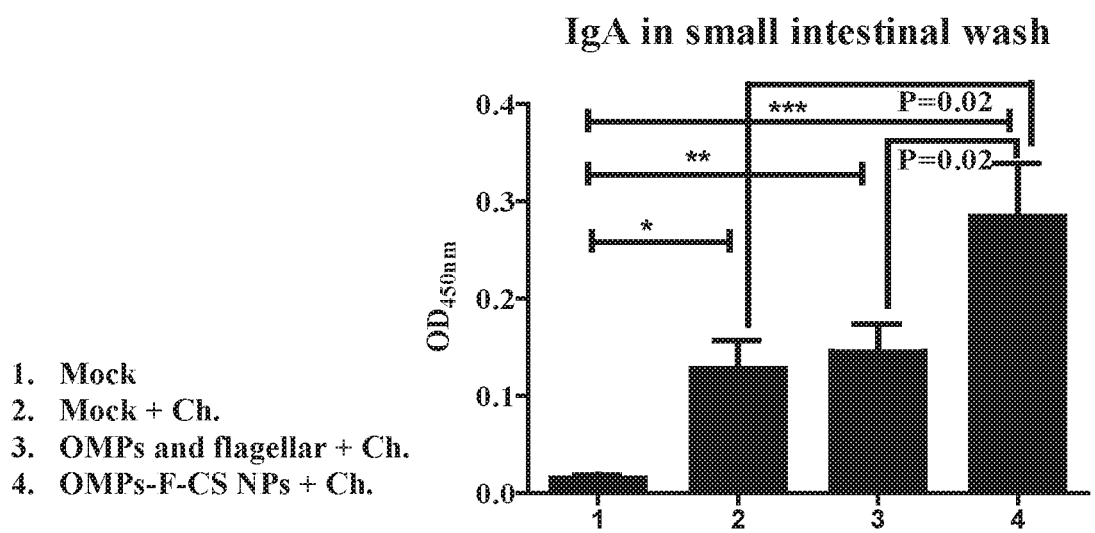
Figure 11E:
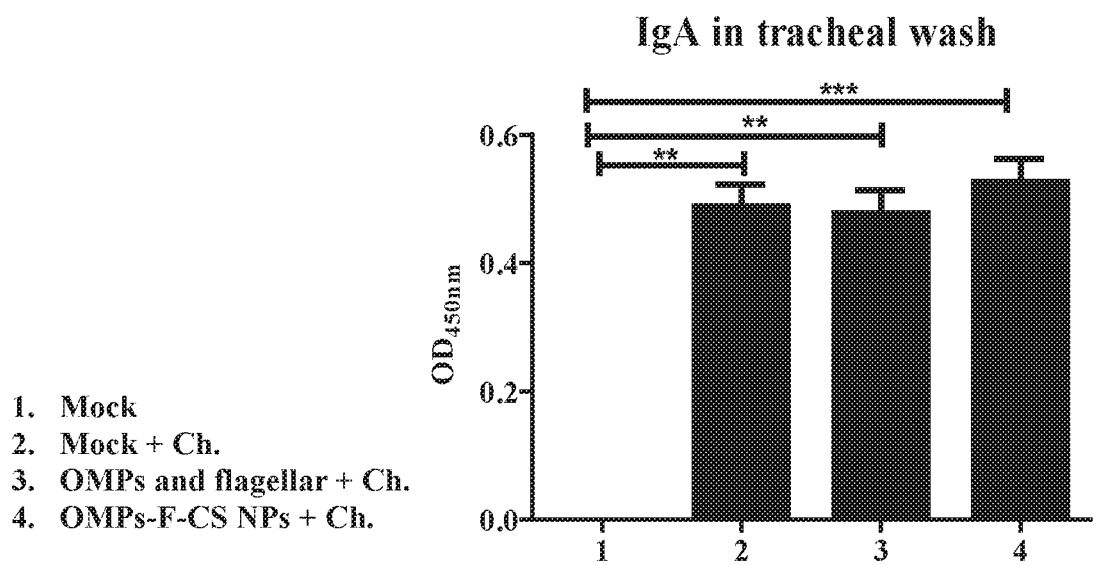
Figure 12A:
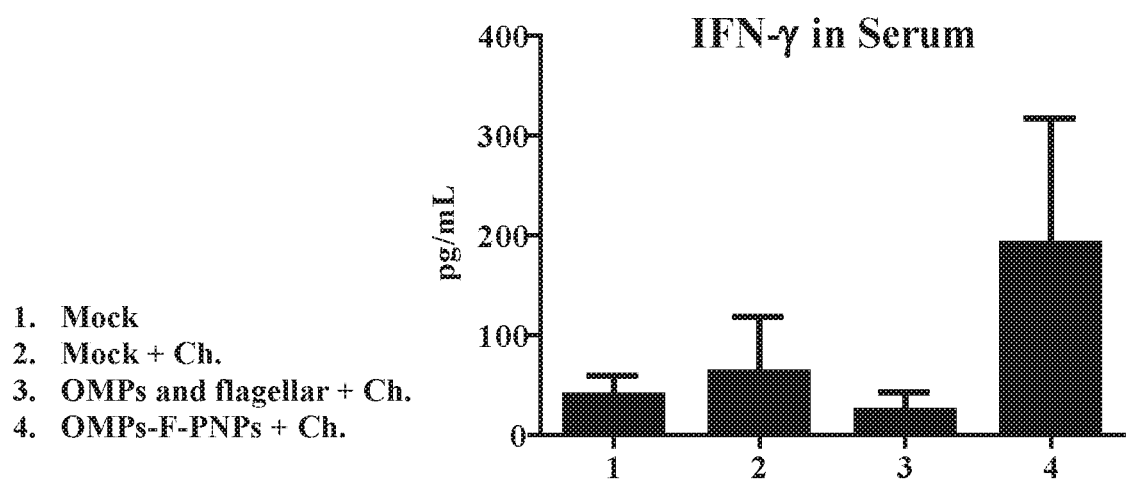
FIGS. 12A-12C. OMPs-specific cell-mediated immune response in OMPs-F-PNPs orally inoculated and Salmonella challenged chickens.
Figure 13A:
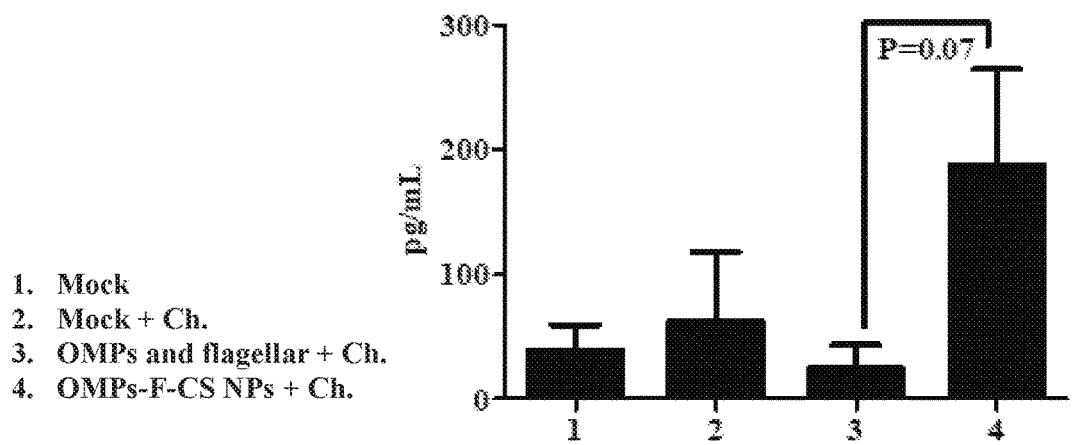
FIGS. 13A-13C. Post-challenge cell-mediated response in chickens vaccinated orally with OMPs-F-CS NPs. Layer chickens were vaccinated, challenged with live S. enteritidis and euthanized at DPC day 10 as described in the figure legend 11.

OMPs-F-CS NPs vaccinated birds OMPs-specific IgA antibody levels were enhanced in cloacal swabs after the first, second and third inoculation compared to mock control group (FIG. 10A-C). Specifically, after the third vaccination dose of the vaccination a significantly increased IgA response compared to both soluble antigens and mock control groups were detected (FIG. 10C). The bacterial challenge at DPC 10 induced significantly higher IgA antibody response in all the birds compared to mock (FIG. 11 A-E). Specifically, in OMPs-F-CS NPs-vaccinated chickens, specific IgA response in serum, bile, cloacal swab and tracheal wash samples were relatively higher compared to soluble antigens group (FIG. 11A-D). However, an increase in OMP-specific IgA level was significantly higher only in the small intestinal wash of OMPs-F-CS NPs vaccinated chickens compared to both mock-challenge and soluble antigens groups (FIG. 11E). OMPs-F-PNPs and OMPs-F-CS NPs induced OMPs specific cell-mediated immune response. OMPs-F-PNPs and OMPs-F-CS NPs vaccinated chickens had increased (but not significant) serum IFN-γ secretion compared to other treatment groups (FIG. 12A and FIG. 13A).

Figure 12B:
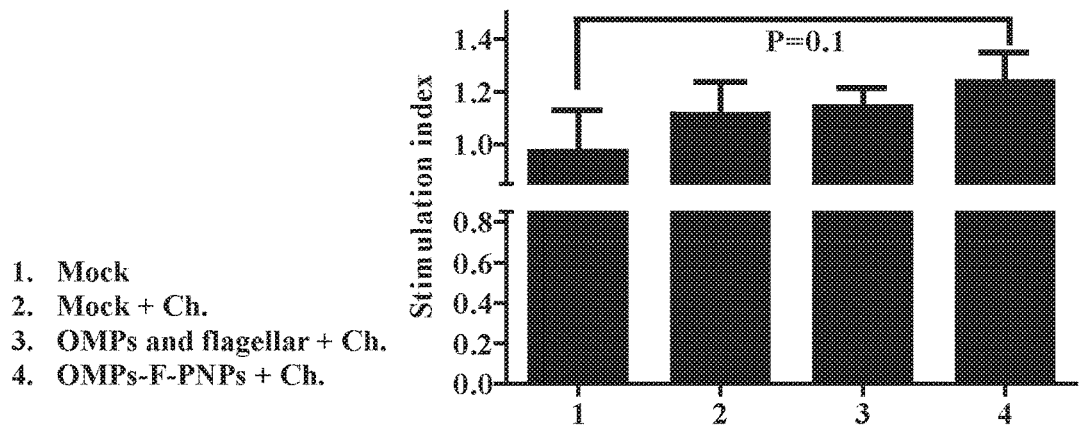
Figure 12C:
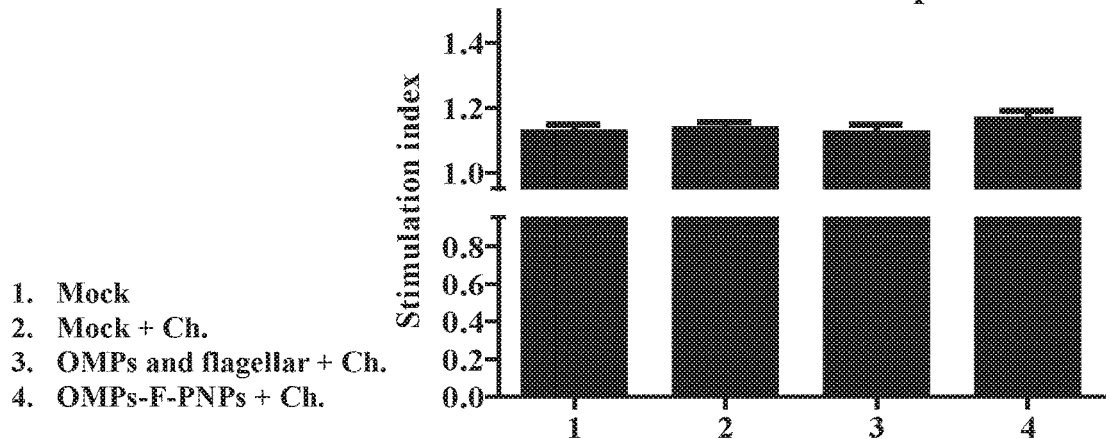
Figure 13B:
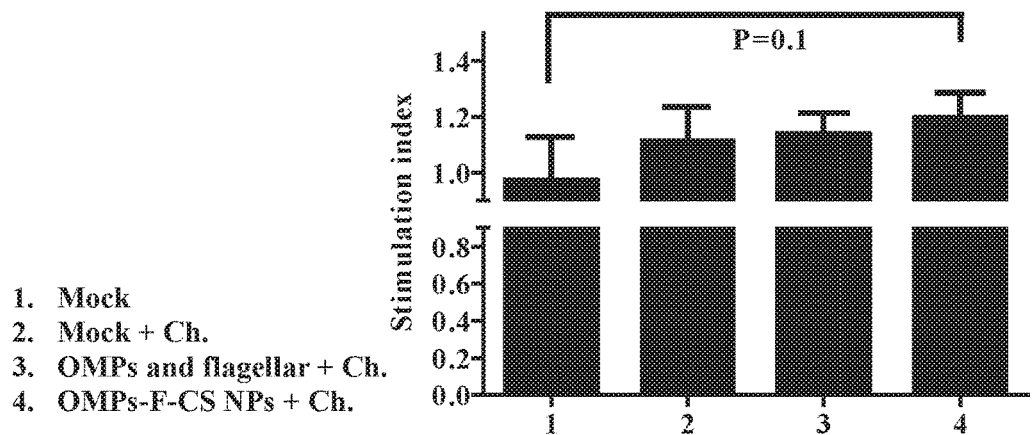
Figure 13C:
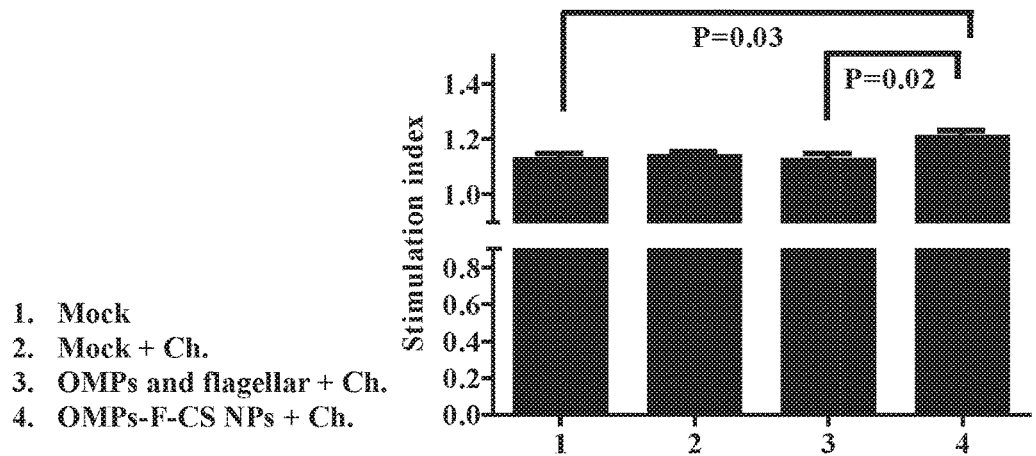

3.4. OMPs-F-PNPs and OMPs-F-CS NPs Induced OMPs Specific Cell-Mediated Immune Response The cell-mediated immune response induced by both the nanoparticle vaccines was measured after the bacterial challenge in birds by estimating OMPs specific lymphocytes stimulation index (SI) in blood and spleen by the cell proliferation assay. In both blood and spleen of OMPs-F-PNPs vaccinated birds an increased trend (but not significant) in SI value (P=0.1) was observed compared to mock group (FIG. 12 B&C). While in OMPs-F-CS NPs vaccinated chickens lymphocytes the SI value was in an increased trend in blood (FIG. 13B), and significantly higher in the spleen compared to both mock and soluble antigens received birds (FIG. 13 C).

Figure 14A:
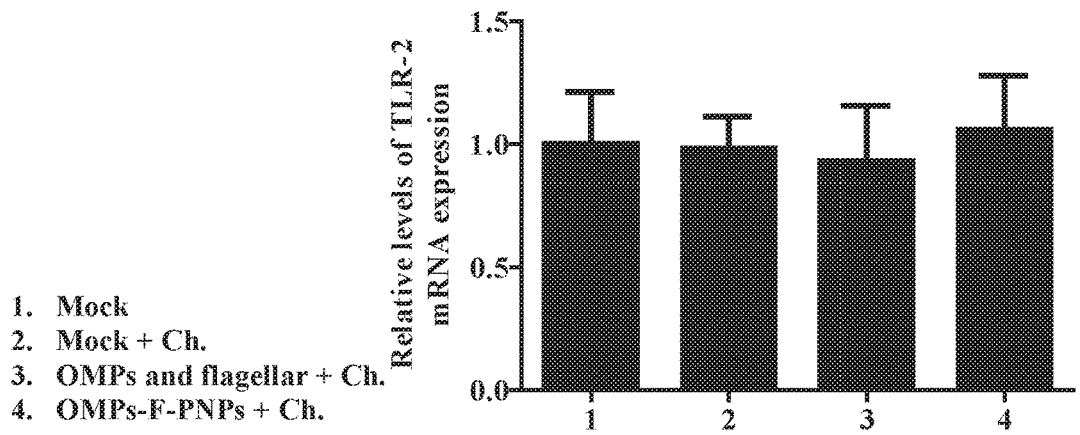
FIGS. 14A-14E. Expression of TLRs and cytokines mRNA in the cecal tonsils of OMPs-F-PNPs orally inoculated and *Salmonella* challenged chickens. The relative mRNA expression levels of (FIG. 14A) TLR-2.
Figure 14B:
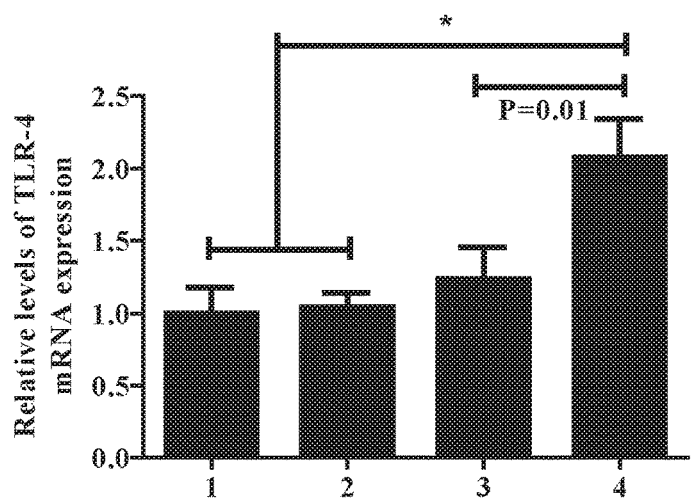
Figure 14C:
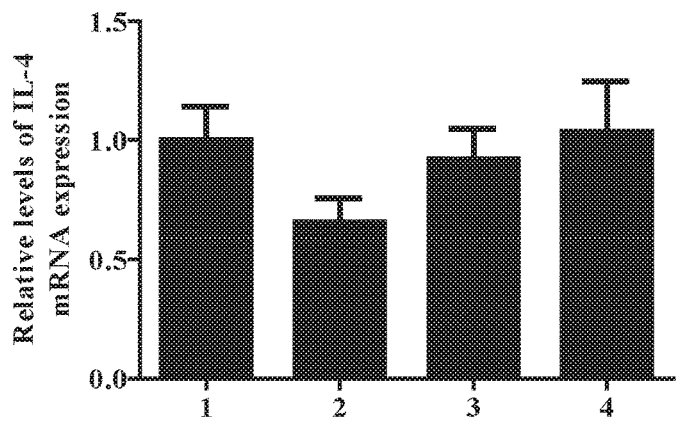
Figure 14D:
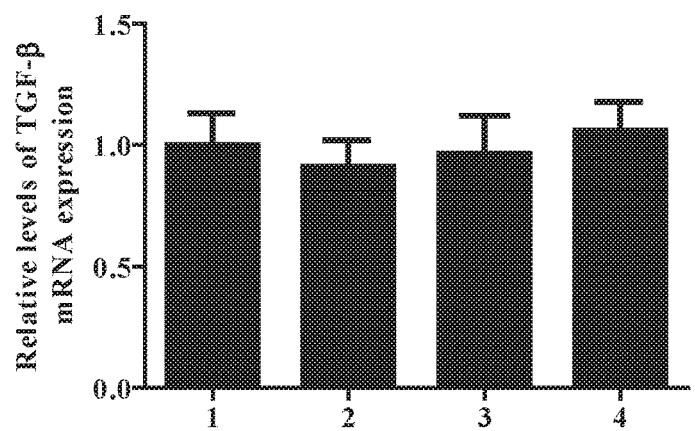
Figure 14E:
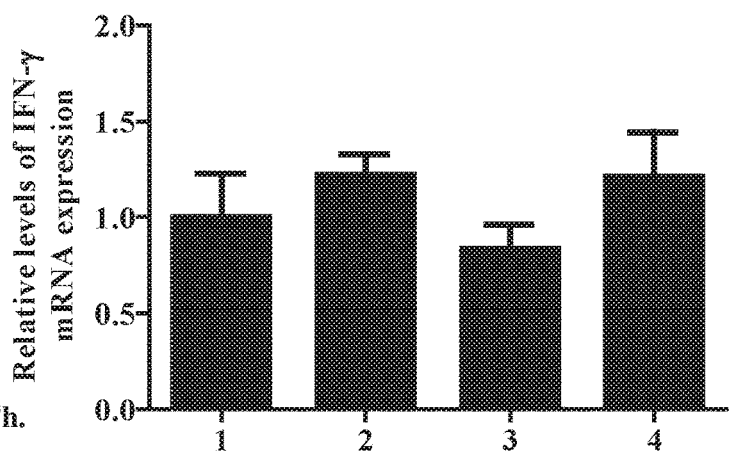
Figure 15A:
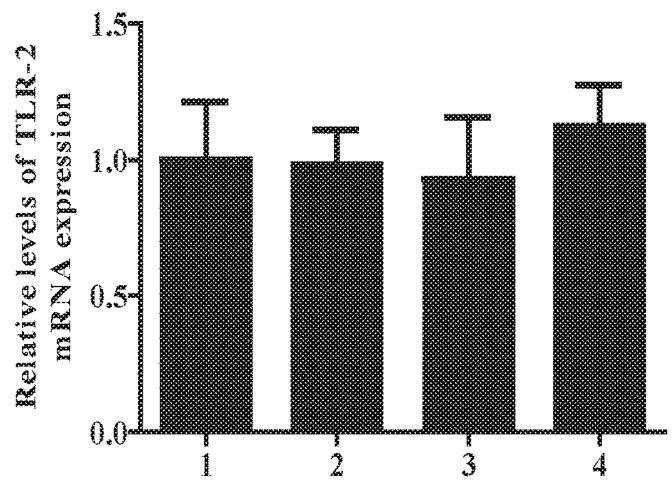
FIGS. 15A-15G. TLRs and cytokines mRNA expression profiles in the cecal tonsils of chickens. Layer chickens were vaccinated, challenged with live *S. enteritidis* and euthanized at DPC day 10 as described in the figure legend 6. The gene expression levels in the cecal tonsils were analyzed by quantitative RT-PCR. The relative mRNA expression levels of (FIG. 15A) TLR-2.
Figure 15B:
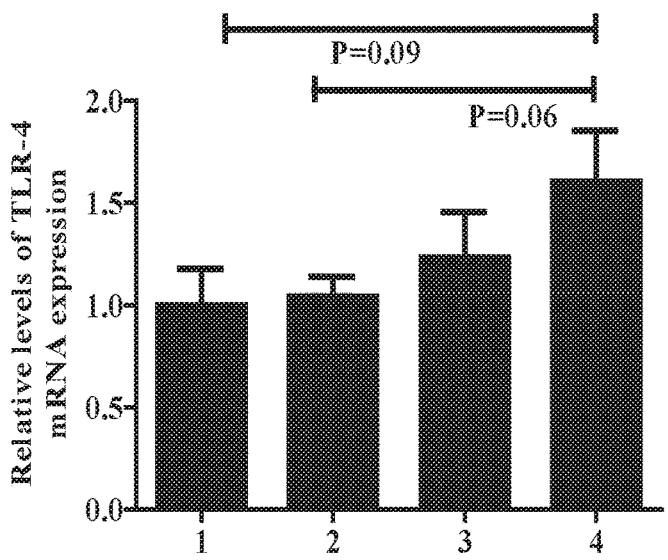
Figure 15C:
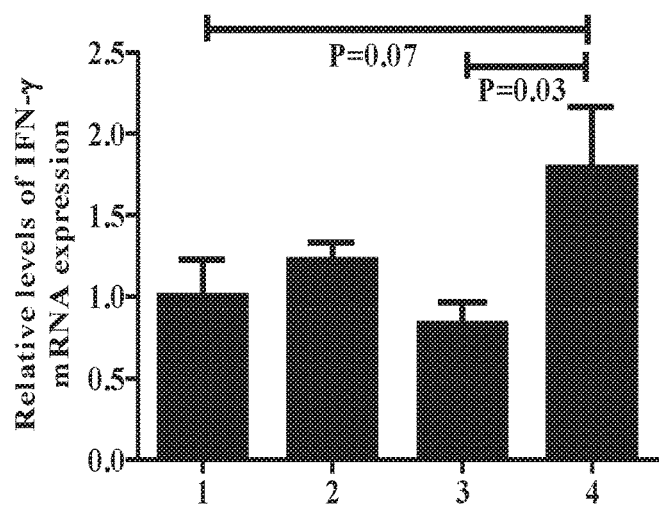
Figure 15D:
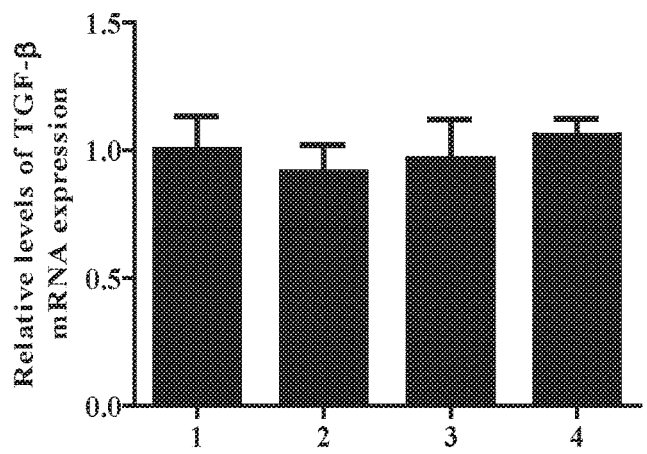
Figure 15E:
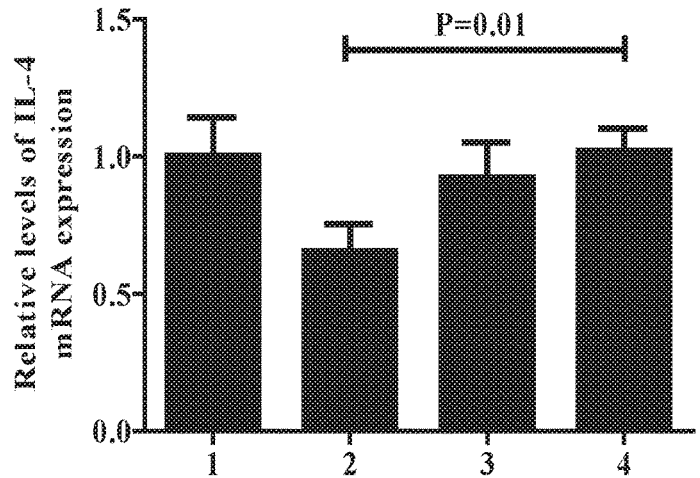
Figure 15F:
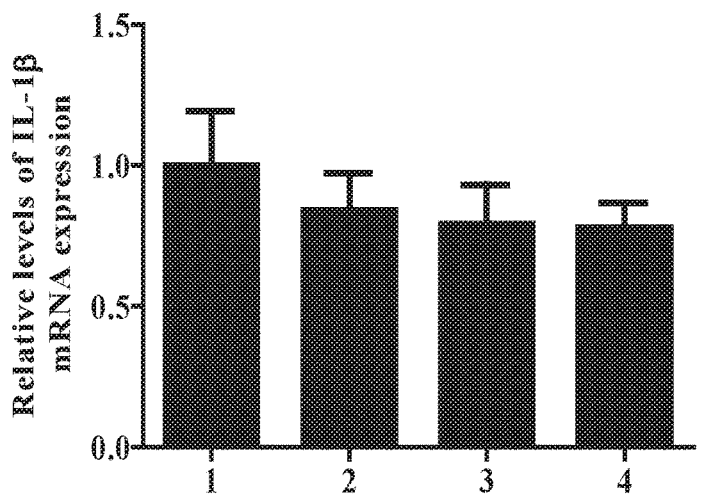
Figure 15G:
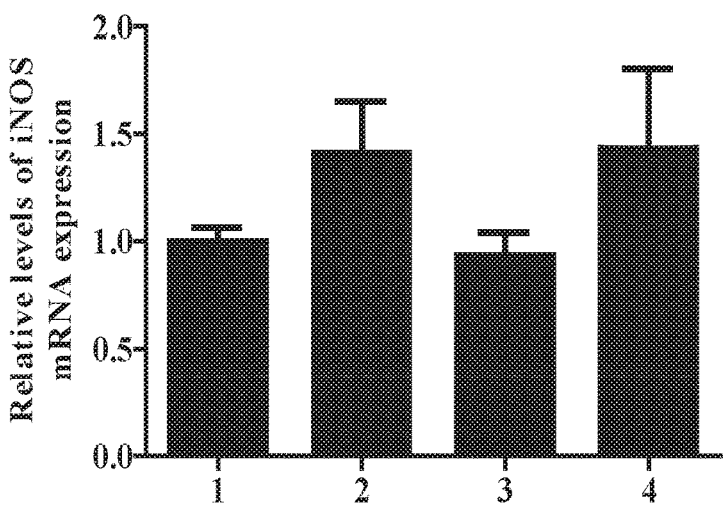

3.5. OMPs-F-PNPs and OMPs-F-CS NPs Upregulated the Expression of Genes of TLRs and Cytokines To determine the ability of OMPs-F-PNPs and OMPs-F-CS NPs to induce immunomodulatory activities, the mRNA expression levels of TLR-2, TLR-4 and cytokines Th1 (IFN-γ and Th2 (IL-4) were analyzed in the cecal tonsils of birds. In the OMPs-F-PNPs vaccinated chickens, significantly higher TLR-4 mRNA expression was observed compared to the soluble vaccine antigens group, but TLR-2 gene expression was unchanged (FIG. 14 A&B). The expression of IL-4 and TGF-β cytokines mRNA was also slightly upregulated in OMPs-F-PNPs vaccinated birds compared to mock and soluble antigens groups, while soluble antigens downregulated IL-4 mRNA expression (FIG. 14 C&D). OMPs-F-PNPs induced slightly higher IFN-γ mRNA expression in cecal tonsils compared to mock and soluble antigens groups, which was comparable to serum IFN-γ response (FIG. 14E). Upregulated TLR-2 mRNAs in OMPs-F-CS NPs vaccinated birds were documented whereas mock-challenged and soluble antigens vaccinated birds had down-regulated mRNA levels (FIG. 15A). OMPs-F-CS NPs vaccinated birds were not significantly elevated in TLR-4 mRNA levels compared to other treatment groups (FIG. 15B). But an increase in IFN-γ mRNA expression in OMPs-F-CS NPs vaccinated birds was significant compared to soluble antigens group (FIG. 15C). TGF-β expression was downregulated in mock-challenge and soluble antigens treated groups, while OMPs-F-CS NPs vaccination increased the mRNA levels (FIG. 15D). OMPs-F-CS NPs vaccination had significantly upregulated the expression of IL-4 compared to mock-challenge, while it was downregulated in soluble antigens group (FIG. 15E). Pro-inflammatory cytokine IL-10 mRNA expression was downregulated in OMPs-F-CS NPs-vaccinated birds compared to other groups (FIG. 15F). Nitric oxide synthase (iNOS) mRNA expression was upregulated in both OMPs-F-CS NPs and mock-challenge groups (FIG. 15G).

3.6. OMPs-F-PNPs Reduced the Bacterial Shedding in Chickens

Figure 16:
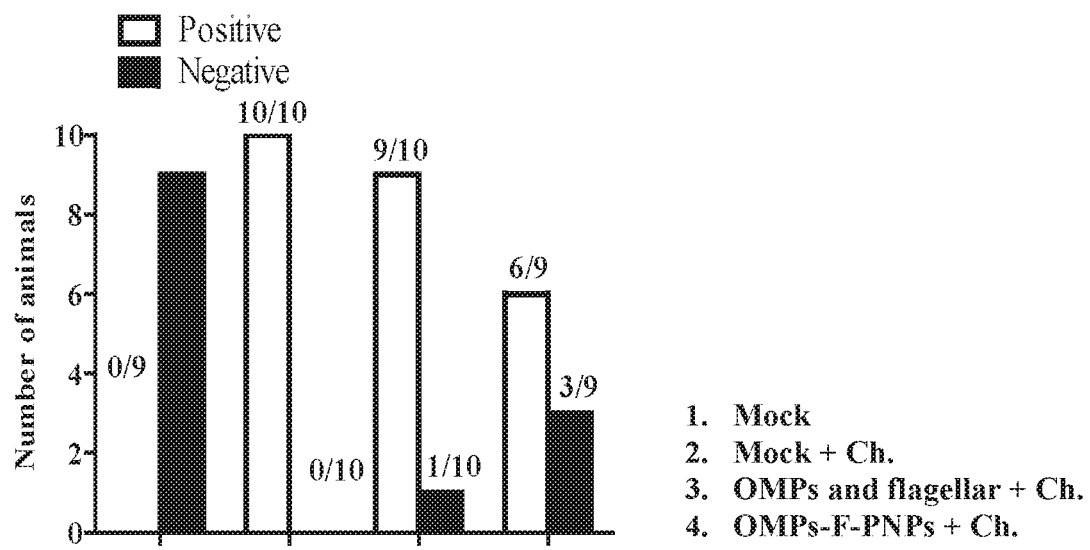
FIG. 16. Detection of live *S. enteritidis* in the cecal contents of chickens vaccinated orally with OMPs-F-PNPs. Layer chickens were vaccinated, challenged with live *S. enteritidis* and euthanized at day 10 post-challenge as described in the figure legend 9. Fresh cecal samples were tested for live *S. enteritidis* by culture method. Initially surviving bacteria was enriched in peptone water (2× concentration) for 12 h at 37° C., followed by streaking on the XLD-NA plates. Representative colonies from the plates were confirmed as *salmonella* by standard methods. Each bar represented the *S. enteritidis* positive/negative chickens in each of the groups.
Figure 17:
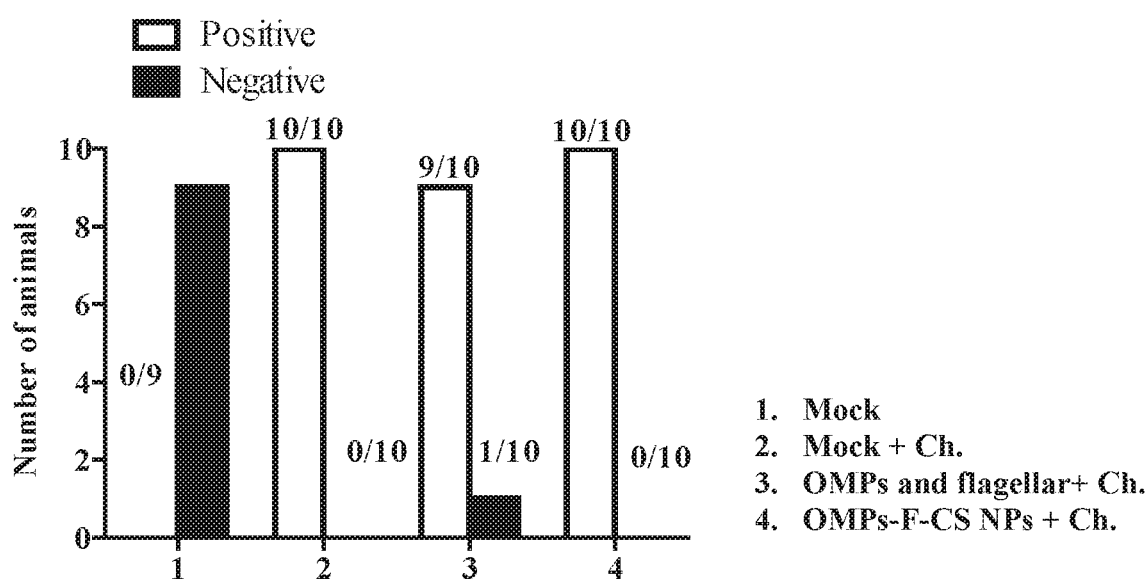
FIG. 17. Detection of live *S. enteritidis* in the cecal contents of chickens vaccinated orally with OMPs-F-CS NPs. Layer chickens were vaccinated, challenged with live *S. enteritidis* and euthanized at day 10 post-challenge as described in the figure legend 11. Fresh cecal samples were tested for live *S. enteritidis* by culture method. Initially surviving bacteria was enriched in peptone water (2× concentration) for 12 h at 37° C., followed by streaking on the XLD-NA plates. Representative colonies from the plates were confirmed as *salmonella* by standard methods. Each bar represented the *S. enteritidis* positive/negative chickens in each of the groups.

Finally, the presence of *S. enteritidis* was qualitatively evaluated in the enriched cecal samples of both the nanoparticle vaccines received birds by using direct plating method. These results revealed that all the mock and mock-challenge chickens were *S. enteritidis* negative (0/9) and positive (10/10), respectively. In soluble antigens vaccinated group 10% of the birds were negative at DPC 10 (1/10). Effect of OMPs-F-PNPs vaccination mediated absence of *S. enteritidis* in 33% birds (3/9) (FIG. 16); while none of the OMPs-F-CS NPs vaccinated birds were negative for live *Salmonella* (10/10) (FIG. 17).

Figure 18:
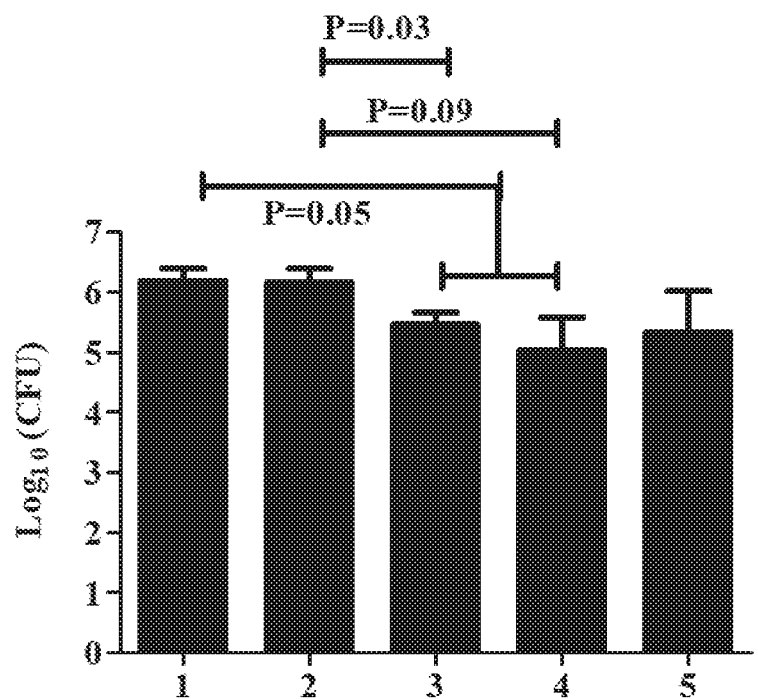
FIG. 18. Detection of live *S. enteritidis* in the whole cecum of chickens vaccinated orally or through drinking water or through feed delivered OMPs-F-CS NPs. Layer chickens vaccinated orally three times at three 3-week intervals with mock challenge saline (group 1) or 500 μg OMPs and flagellar protein (group 2) or same amount of protein loaded nanoparticles (OMPs-F-CS NPs) delivered in oral gavage needle (group 3) or same amount of protein loaded nanoparticles (OMPs-F-CS NPs) delivered in drinking water (group 4) or same amount of protein loaded nanoparticles (OMPs-F-CS NPs) delivered in feed (group 5). All the groups were challenged orally with 5×10$^6$ CFU/mL of live *S. enteritidis*, and euthanized at day 10 post-challenge. The collected whole cecum crushed in PBS and steaked in XLD-NA plates, incubated for 48 h at 37° C. to detect live *S. enteritidis*. Each bar is the mean±SEM of 4 to 5 chickens Log$_{10}$(CFU) values, and the data were analyzed by non-parametric Kruskal-Wallis test followed by p value differences in between the groups were determined by Mann-Whitney test.
Figure 19:
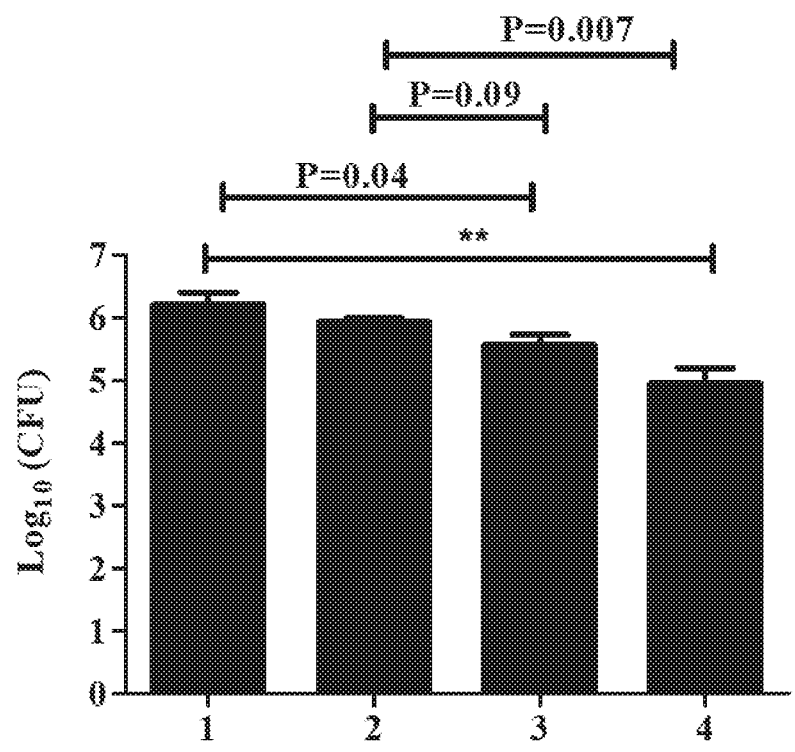
FIG. 19. Detection of live *S. enteritidis* in the whole cecum of chickens vaccinated orally with *Salmonella enteritidis* killed whole bacterium antigenic extracted (KAg) protein loaded and surface flagellar coated polyanhydride nanoparticles (KAg—F-PNPs) or KAg protein loaded and surface flagellar coated chitosan nanoparticles (KAg—F-CS NPs). Layer chickens vaccinated orally three times at three 3-week intervals with mock challenge saline (group 1) or 100 μg KAg proteins (group 2) or same amount of KAg loaded nanoparticles (KAg—F-PNPs) (group 3) or same amount of KAg loaded nanoparticles (KAg—F-CS NPs) (group 4). All the groups were challenged orally with 5×10$^6$ CFU/mL of live *S. enteritidis*, and euthanized at day 10 post-challenge. The collected whole cecum crushed in PBS and steaked in XLD-NA plates, incubated for 48 h at 37° C. to detect live *S. enteritidis*. Each bar is the mean±SEM of 5 chickens Log$_{10}$(CFU) values, and the data were analyzed by non-parametric Kruskal-Wallis test followed by p value differences in between the groups were determined by Mann-Whitney test (*P<0.05, P<0.01 and *P<0.001).

In additional experiments, the oral and drinking water method delivered OMPs-F-CS NPs vaccinated birds showed significantly reduced bacterial levels in cecum compared to $5 \times 10^6$ CFU/mL of *S. enteritidis* challenged birds. Further, compared to soluble protein vaccinated and challenged birds, the oral and drinking water method delivered OMPs-F-CS NPs vaccinated animals significant and non-significantly reduced bacterial shedding, respectively (FIG. 18). Moreover, feed delivered OMPs-F-CS NPs vaccinated birds non-significantly reduced bacterial levels compared to both mock challenge and soluble protein vaccinated birds (FIG. 18). The KAg—F-PNPs and KAg—F-CS NPs orally vaccinated birds significantly reduced *Salmonella* levels in cecum compared to $5 \times 10^6$ CFU/mL of *S. enteritidis* challenged birds (FIG. 19). KAg—F-CS NPs orally vaccinated birds had significantly reduced *Salmonella* levels compared to soluble KAg vaccinated birds (FIG. 19).

4. DISCUSSION

*Salmonella enterica* illness in poultry is one of the notable important and unavoidable issues in the US. Predominantly, *Salmonella enterica* serovar *enteritidis* remains as a high risk bacterial food poisoning around the globe [15]. An extensive usage of antibiotics in poultry has led to the threat of developing multiple antibiotic-resistant bacteria. This has been a major concern warranting the need of developing an effective vaccine to mitigate major zoonotic infections [15]. GI tract is the principal mucosal surface in the body, plays a pivotal role in controlling the invasion of pathogens and host defense. In the GI tract, GALT associated PPs in the small intestines and other lymphoid aggregates in the large intestines are involved in maintaining immune homeostasis. The PPs associated M cells are responsible for sampling and processing of mucosal foreign antigens and triggering the mucosal immune responses [53]. The goal of oral vaccination is targeting antigens to mucosal M cells and activating PPs immune cells, imitating the natural process of building immunity against enteric pathogens [54]. Keeping all this in mind, the immunogenic *Salmonella* antigens (OMPs and flagellar) containing biocompatible and mucoadhesive PNPs and CS NPs vaccines were formulated to mitigate Salmonellosis in poultry. For mimicking the entry of live *Salmonella* through PPs-M cells, the nanoparticles were surface labelled with flagellar protein.

Biodegradable polymers can be used as a vaccine delivery agent owing to their biocompatibility, biodistribution and sustained antigen release properties [55]. Due to unique physicochemical properties, engineered biodegradable polymer act as a potent adjuvant, and importantly deliver the vaccine cargo to desired receptors triggering specific immune responses [56]. Studies have established that the nanoparticle size, shape and surface charge determines their biological properties [57]. Polymeric nanoparticles of less than 500 nm are actively uptaken by APCs via pinocytosis and macropinocytosis. Methods were determined to successfully formulate immunogenic *Salmonella* antigens loaded PNPs and CS NPs using the solvent displacement and ionic gelation method, respectively. A uniform size dispersion, spherical shape, high loading efficiency and surface flagellar coating in nanoparticles of <500 nm size was achieved, ideal for APCs uptake. The vaccine proteins loading induced a slight change in the size and surface conformation of nanoparticles [59]. The formulated PNPs were of negative charge and CS NPs were positive charge, thus both are uptaken and function differently. Positively charged CS NPs are supposed to be highly mucoadhesive and attracted strongly to negatively charged mucosal epithelial membrane and uptaken by APCs. Negatively charged PNPs are relatively less uptaken up APCs, but they stay longer to facilitate delivery of antigens to immune cells [60].

Previous reports showed that even very high concentration of PNPs are biocompatible, and do not stimulate toxic biomarkers on vital organs compared to routine vaccine adjuvants, and quickly get distributed throughout the lymphoid organs inducing long-lasting immunity [61]. The TPP cross-linked CS NPs are stable and highly biocompatible excellent carriers of vaccine cargo [47]. It was shown that both the nanoparticle vaccine preparations are biocompatible to chicken RBCs. In spite of using a chemical cross linker PNPs maintained biocompatibility and stable in wide acid pH conditions, suggesting their stability for oral delivery [62]. Since the target site is a slightly acidic small intestine, the formulated nanoparticle vaccines are bioavailable. The stable nanoparticles protect vaccine proteins from the enzymatic degradation at acidic pH in the GI tract [63]. The CS NPs is stable when exposed to highly acidic (pH 2) environment over a long period of time, thus efficiently protecting antigens in the GI tract and considered as a suitable carrier for oral antigen delivery [64].

However, many bioadhesive polymers have low specific targeting ability in the GALT PPs, thus surface coating with specific ligands on such nanoparticles enhance the targeting potential to gut receptors. In a susceptible host live *Salmonella* adhere to the mucosal layer and enter PPs-M cells of the follicle associated epithelium of the small intestines. Like the live *Salmonella* flagellar protein, extracted *S. enteritidis* flagellin is also invasive and specifically target to PPs M cells [22]. Likewise, enriched flagellin surface coated PNPs oral treatment mimics the natural *Salmonella* invasion and colonization in the rat GI tract [36]. In an in vitro study using the M cell line, OVA loaded CS NPs are attracted and processed by M cells [65]. In chickens, orally treated flagellar coated PNPs and CS NPs were actively bound to intestinal mucosal layer and readily uptaken by PPs immune cells. As indicated by fluorescent microscopy results demonstrating uniform distribution of flagellar coated nanoparticles in the mucosal PPs sites, comparable to fluorescent dye labelled flagellin coated PNPs delivered by oral route in rats [36].

Furthermore, in chickens orally vaccinated with OMPs-F-PNPs and challenged with live *Salmonella* significantly higher systemic IgG and increasing trend in IgA antibody responses in the small intestines compared to soluble antigens was detected. The surface positive charge of OMPs-F-CS NPs influenced the significantly higher small intestinal IgA production. Protection against *Salmonella* infection is a much more complicated process and involves communication of both innate and adaptive immune systems [66]. An adjuvant based OMPs delivery in poultry significantly increase antibody titers and decrease bacterial shedding [20]. The OMPs are the major immunodominant proteins, and in orally vaccinated chickens they elicit high antibody titers [20]. But local intestinal IgA response contributes to clearance of bacterial shedding [67]. *S. enteritidis* extracted antigens covalently conjugated to starch microparticles delivered orally induces both local and systemic immune response in mice [68]. The flagellin coated OVA loaded PNPs oral vaccination prompted higher and balanced systemic antibody response, and also elicited a higher secretory IgA in mice. The cross-linked PNPs has adjuvant effects triggering the complement system and attract immature APCs that are stimulated by TLR2 and TLR4, and activates the innate immune system [22, 35, 69]. The flagellin coated PNPs are actively uptaken by the gut PPs and induces secretory IgA antibody response [22, 36]. The rVP1 an enterovirus antigen delivered through chitosan particles orally in mice induces broad spectrum immune response and proved as a favorable subunit vaccine [70]. The OMPs vaccine encapsulated CS NPs produce higher antibody titers and had better disease prevention in the fish system [71].

OMPs-F-PNPs vaccinated birds showed a trend in OMPs specific recall lymphocyte response in blood and spleen; promisingly, at much higher levels in OMPs-F-CS NPs vaccinated birds. These results show that both the nanoparticles vaccine have the capability to induce cell-mediated immune response in poultry. Detection of antigen specific lymphocyte proliferation is an acceptable method of proving the cell-mediated immunity in chickens vaccinated with *Salmonella* vaccine extract [72]. Splenocytes of OMPs vaccinated mice show significantly higher protein specific proliferative response than control [73]. OmpA vaccinated splenocytes co-cultured with APCs enhances T-cell proliferation, Th1 polarization and IFN-γ production in mice [74]. Splenocytes of OMPs and flagellar vaccinated chickens restimulated with vaccine antigens induces significantly higher IFN-γ and IL-2 production. Moreover, vaccine antigens encapsulated CS NPs immunized chickens induces significantly higher lymphocyte proliferation and effectively control the disease [47].

In this example, both the OMPs-F-PNPs and OMPs-F-CS NPs delivery system helped in targeting the vaccine cargo to intestinal PPs, and induced OMPs-specific antibody and T cell responses, indicating a reduction of the *Salmonella* colonization in birds. However, complete absence of *Salmonella* cecal colonization was observed only in 33% of birds immunized with OMPs-F-PNPs, and OMPs-F-CS NPs vaccination failed to completely clear bacterial colonization from any birds. The moderate protective efficacy of the vaccines is likely due to a very high bacterial challenge dose used in this study compared to an experimental infection [75]. In another experiment, a moderate dose of live bacterium was used for challenge and it was found that OMPs-F-CS NPs oral and drinking water method delivery, KAg-F-PNPs, and KAg-F-CS NPs oral delivery significantly reduced *Salmonella* burden in birds cecum.

5. CONCLUSION

In conclusion, biocompatible and biologically stable cationic and anionic nanoparticles vaccines were formulated, which specifically target the vaccine cargo to intestinal PPs of birds. For the first time, the efficacy of orally delivered nanoparticle based subunit vaccines was demonstrated against a *Salmonella* infection in birds. In vaccinated birds, PNPs vaccine predominantly induced antigen specific IgG response, and CS NPs vaccine elicited mucosal IgA and T cell responses. In addition, both *Salmonella* nanovaccines examined in this example induced balanced Th1 and Th2 cytokine mRNA expression levels. The robust immunity induced by both *Salmonella* nanovaccines helped to reduce bacterial burden. Thus, these study results show that both the nanoparticle formulations are suitable for oral delivery of subunit antigens or whole bacterium killed antigen against *Salmonella* in poultry.

TABLE 1

Experimental design showing assignment of layer chicken groups.

| Group | Experimental groups | No birds | Vaccination 1st dose (DPV 0/DPC 73) 2nd dose (DPV 21/DPC 52) 3rd dose (DPV 42/DPC 31) | Challenge (DPV 63/ DPC 0) |
|---|---|---|---|---|
| 1 | Mock | 9 | PBS | PBS |
| 2 | Mock + Ch. | 10 | PBS | S. enteritidis |
| 3 | OMPs and flagellar + Ch. | 10 | OMPs + flagellin | S. enteritidis |
| 4 | Polyanhydride nanovaccine + Ch. | 8 | OMPs-F-PNPs | S. enteritidis |
| 5 | Chitosan nanovaccine + Ch. | 10 | OMPs-F-CS NPs | S. enteritidis |

DPV—Day post- vaccination;
DPC—Day of post-challenge;
Ch—Challenge

REFERENCES

[1] Khan M I, Fadl A A, Venkitanarayanan K S. Reducing colonization of *Salmonella Enteritidis* in chicken by targeting outer membrane proteins. J Appl Microbiol. 2003; 95:142-5.

[2] Scallan E, Hoekstra R M, Angulo F J, Tauxe R V, Widdowson M A, Roy S L, et al. Foodborne illness acquired in the United States—major pathogens. Emerg Infect Dis. 2011; 17:7-15.

[3] Fabrega A, Vila J. *Salmonella enterica* serovar *typhimurium* skills to succeed in the host: virulence and regulation. Clin Microbiol Rev. 2013; 26:308-41.

[4] Majowicz S E, Musto J, Scallan E, Angulo F J, Kirk M, O'Brien S J, et al. The global burden of nontyphoidal *Salmonella* gastroenteritis. Clin Infect Dis. 2010; 50:882-9.

[5] Humphrey T, Jorgensen F. Pathogens on meat and infection in animals—Establishing a relationship using *campylobacter* and *salmonella* as examples. Meat science. 2006; 74:89-97.

[6] Lee S K, Chon J W, Song K Y, Hyeon J Y, Moon J S, Seo K H. Prevalence, characterization, and antimicrobial susceptibility of *Salmonella gallinarum* isolated from eggs produced in conventional or organic farms in South Korea. Poult Sci. 2013; 92:2789-97.

[7] Greig J D, Ravel A. Analysis of foodborne outbreak data reported internationally for source attribution. Int J Food Microbiol. 2009; 130:77-87.

[8] Varmuzova K, Faldynova M, Elsheimer-Matulova M, Sebkova A, Polansky O, Havlickova H, et al Immune protection of chickens conferred by a vaccine consisting of attenuated strains of *Salmonella Enteritidis, typhimurium* and *Infantis*. Vet Res. 2016; 47:94.

[9] Tennant S M, Levine M M. Live attenuated vaccines for invasive *Salmonella* infections. Vaccine. 2015; 33 Suppl 3:C36-41.

[10] Okamura M, Tachizaki H, Kubo T, Kikuchi S, Suzuki A, Takehara K, et al. Comparative evaluation of a bivalent killed *Salmonella* vaccine to prevent egg contamination with *Salmonella enterica* serovars *Enteritidis, typhimurium*, and *gallinarum* biovar *Pullorum*, using 4 different challenge models. Vaccine. 2007; 25:4837-44.

[11] Tran T Q, Quessy S, Letellier A, Desrosiers A, Boulianne M Immune response following vaccination against *Salmonella Enteritidis* using 2 commercial bacterins in laying hens. Can J Vet Res. 2010; 74:185-92.

[12] Kamble N M, Lee J H. Homologous prime-boost immunization with live attenuated *Salmonella enterica* serovar *Senftenberg* and its preventive efficacy against experimental challenge with various strains of *S. Senftenberg*. BMC Vet Res. 2017; 13:39.

[13] Wolfenden R E, Layton S L, Wolfenden A D, Khatiwara A, Gaona-Ramirez G, Pumford N R, et al. Development and evaluation of candidate recombinant *Salmonella*-vectored *Salmonella* vaccines. Poult Sci. 2010; 89:2370-9.

[14] Sheela R R, Babu U, Mu J, Elankumaran S, Bautista D A, Raybourne R B, et al Immune responses against *Salmonella enterica* serovar *enteritidis* infection in virally immunosuppressed chickens. Clin Diagn Lab Immunol. 2003; 10:670-9.

[15] Barrow P A. *Salmonella* infections: immune and non-immune protection with vaccines. Avian Pathol. 2007; 36:1-13.

[16] Lee Y J, Mo I P, Kang M S. Protective efficacy of live *Salmonella gallinarum* 9R vaccine in commercial layer flocks. Avian Pathol. 2007; 36:495-8.

[17] Panel E S. Opinion of the Scientific Panel on Biological Hazards on a request from the Commission related to the use of vaccines for the control of *Salmonella* in poultry. The EFSA Journal. 2004; 114:1-74.

[18] Okamura M, Ueda M, Noda Y, Kuno Y, Kashimoto T, Takehara K, et al Immunization with outer membrane protein A from *Salmonella enterica* serovar *Enteritidis* induces humoral immune response but no protection against homologous challenge in chickens. Poult Sci. 2012; 91:2444-9.

[19] Prejit, Agarwal R K, Porteen K, Dubal Z B, Asha K, Shweta S, et al. Evaluation of recombinant outer membrane protein based vaccine against *Salmonella typhimurium* in birds. Biologicals: journal of the International Association of Biological Standardization. 2013; 41:162-8.

[20] Meenakshi M, Bakshi C S, Butchaiah G, Bansal M P, Siddiqui M Z, Singh V P. Adjuvanted outer membrane protein vaccine protects poultry against infection with *Salmonella enteritidis*. Vet Res Commun. 1999; 23:81-90.

[21] Pore D, Mahata N, Pal A, Chakrabarti M K. Outer membrane protein A (OmpA) of *Shigella flexneri* 2a, induces protective immune response in a mouse model. PLoS One. 2011; 6:e22663.

[22] Salman H H, Irache J M, Gamazo C Immunoadjuvant capacity of flagellin and mannosamine-coated poly(anhydride) nanoparticles in oral vaccination. Vaccine. 2009; 27:4784-90.

[23] Kim S Y, Doh H J, Jang M H, Ha Y J, Chung S I, Park H J. Oral immunization with *Helicobacter pylori*-loaded poly(D, L-lactide-co-glycolide) nanoparticles. *Helicobacter*. 1999; 4:33-9.

[24] Vasserman Y, Pitcovski J. Genetic detoxification and adjuvant-activity retention of *Escherichia coli* enterotoxin LT. Avian Pathol. 2006; 35:134-40.

[25] Dhakal S, Hiremath J, Bondra K, Lakshmanappa Y S, Shyu D L, Ouyang K, et al. Biodegradable nanoparticle delivery of inactivated swine influenza virus vaccine provides heterologous cell-mediated immune response in pigs. J Control Release. 2017; 247:194-205.

[26] Dhakal S, Goodman J, Bondra K, Lakshmanappa Y S, Hiremath J, Shyu D L, et al. Polyanhydride nanovaccine against swine influenza virus in pigs. Vaccine. 2017; 35:1124-31.

[27] Annamalai T, Pina-Mimbela R, Kumar A, Binjawadagi B, Liu Z, Renukaradhya G J, et al. Evaluation of nanoparticle-encapsulated outer membrane proteins for the control of *Campylobacter jejuni* colonization in chickens. Poult Sci. 2013; 92:2201-11.

[28] Ulery B D, Nair L S, Laurencin C T. Biomedical Applications of Biodegradable Polymers. Journal of polymer science Part B, Polymer physics. 2011; 49:832-64.

[29] Piskin E. Biodegradable polymers as biomaterials. J Biomater Sci Polym Ed. 1995; 6:775-95.

[30] Sankar R, Karthik S, Subramanian N, Krishnaswami V, Sonnemann J, Ravikumar V. Nanostructured delivery system for Suberoylanilide hydroxamic acid against lung cancer cells. Materials science & engineering C, Materials for biological applications. 2015; 51:362-8.

[31] Garland M J, Singh T R, Woolfson A D, Donnelly R F. Electrically enhanced solute permeation across poly(ethylene glycol)-crosslinked poly(methyl vinyl ether-co-maleic acid) hydrogels: effect of hydrogel crosslink density and ionic conductivity. Int J Pharm. 2011; 406:91-8.

[32] Arbos P, Campanero M A, Arangoa M A, Renedo M J, Irache J M. Influence of the surface characteristics of PVM/MA nanoparticles on their bioadhesive properties. J Control Release. 2003; 89:19-30.

[33] Cerchiara T, Luppi B, Chidichimo G, Bigucci F, Zecchi V. Chitosan and poly(methyl vinyl ether-co-maleic anhydride) microparticles as nasal sustained delivery systems. Eur J Pharm Biopharm. 2005; 61:195-200.

[34] Agueros M, Areses P, Campanero M A, Salman H, Quincoces G, Penuelas I, et al. Bioadhesive properties and biodistribution of cyclodextrin-poly(anhydride) nanoparticles. Eur J Pharm Sci. 2009; 37:231-40.

[35] Reboucas Jde S, Irache J M, Camacho A I, Esparza I, Del Pozo V, Sanz M L, et al. Development of poly (anhydride) nanoparticles loaded with peanut proteins: the influence of preparation method on the immunogenic properties. Eur J Pharm Biopharm. 2012; 82:241-9.

[36] Salman H H, Gamazo C, Campanero M A, Irache J M. Salmonella-like bioadhesive nanoparticles. J Control Release. 2005; 106:1-13.

[37] Samal S K, Dash M, Van Vlierberghe S, Kaplan D L, Chiellini E, van Blitterswijk C, et al. Cationic polymers and their therapeutic potential. Chem Soc Rev. 2012; 41:7147-94.

[38] Bowman K, Leong K W. Chitosan nanoparticles for oral drug and gene delivery. Int J Nanomedicine. 2006; 1:117-28.

[39] Ilium L. Nanoparticulate systems for nasal delivery of drugs: a real improvement over simple systems? J Pharm Sci. 2007; 96:473-83.

[40] Wang J J, Zeng Z W, Xiao R Z, Xie T, Zhou G L, Zhan X R, et al. Recent advances of chitosan nanoparticles as drug carriers. Int J Nanomedicine. 2011; 6:765-74.

[41] Schipper N G, Varum K M, Artursson P. Chitosans as absorption enhancers for poorly absorbable drugs. 1: Influence of molecular weight and degree of acetylation on drug transport across human intestinal epithelial (Caco-2) cells. Pharm Res. 1996; 13:1686-92.

[42] Dodane V, Amin Khan M, Merwin J R. Effect of chitosan on epithelial permeability and structure. Int J Pharm. 1999; 182:21-32.

[43] van der Lubben I M, Verhoef J C, Borchard G, Junginger H E. Chitosan for mucosal vaccination. Adv Drug Deliv Rev. 2001; 52:139-44.

[44] Koppolu B, Zaharoff D A. The effect of antigen encapsulation in chitosan particles on uptake, activation and presentation by antigen presenting cells. Biomaterials. 2013; 34:2359-69.

[45] Ochoa-Reparaz J, Sesma B, Alvarez M, Jesus Renedo M, Irache J M, Gamazo C. Humoral immune response in hens naturally infected with Salmonella Enteritidis against outer membrane proteins and other surface structural antigens. Vet Res. 2004; 35:291-8.

[46] Quan S, Hiniker A, Collet J F, Bardwell J C. Isolation of bacteria envelope proteins. Methods Mol Biol. 2013; 966:359-66.

[47] Zhao K, Chen G, Shi X M, Gao T T, Li W, Zhao Y, et al. Preparation and efficacy of a live newcastle disease virus vaccine encapsulated in chitosan nanoparticles. PLoS One. 2012; 7:e53314.

[48] Sankar R, Ravikumar V. Biocompatibility and biodistribution of suberoylanilide hydroxamic acid loaded poly (DL-lactide-co-glycolide) nanoparticles for targeted drug delivery in cancer. Biomed Pharmacother. 2014; 68:865-71.

[49] Ochoa J, Irache J M, Tamayo I, Walz A, DelVecchio V G, Gamazo C. Protective immunity of biodegradable nanoparticle-based vaccine against an experimental challenge with Salmonella Enteritidis in mice. Vaccine. 2007; 25:4410-9.

[50] Ferreira A J, Ferreira C S, Knobl T, Moreno A M, Bacarro M R, Chen M, et al. Comparison of three commercial competitive-exclusion products for controlling Salmonella colonization of broilers in Brazil. J Food Prot. 2003; 66:490-2.

[51] Hamid N, Jain S K. Characterization of an outer membrane protein of Salmonella enterica serovar typhimurium that confers protection against typhoid. Clin Vaccine Immunol. 2008; 15:1461-71.

[52] Komoriya K, Shibano N, Higano T, Azuma N, Yamaguchi S, Aizawa S I. Flagellar proteins and type III-exported virulence factors are the predominant proteins secreted into the culture media of Salmonella typhimurium. Mol Microbiol. 1999; 34:767-79.

[53] Miller H, Zhang J, Kuolee R, Patel G B, Chen W. Intestinal M cells: the fallible sentinels? World J Gastroenterol. 2007; 13:1477-86.

[54] Azizi A, Kumar A, Diaz-Mitoma F, Mestecky J Enhancing oral vaccine potency by targeting intestinal M cells. PLoS Pathog. 2010; 6:e1001147.

[55] Renukaradhya G J, Narasimhan B, Mallapragada S K. Respiratory nanoparticle-based vaccines and challenges associated with animal models and translation. J Control Release. 2015; 219:622-31.

[56] Astete C E, Sabliov C M. Synthesis and characterization of PLGA nanoparticles. J Biomater Sci Polym Ed. 2006; 17:247-89.

[57] Morachis J M, Mahmoud E A, Almutairi A. Physical and chemical strategies for therapeutic delivery by using polymeric nanoparticles. Pharmacol Rev. 2012; 64:505-19.

[58] Reddy S T, van der Vlies A J, Simeoni E, Angeli V, Randolph G J, O'Neil C P, et al. Exploiting lymphatic transport and complement activation in nanoparticle vaccines. Nat Biotechnol. 2007; 25:1159-64.

[59] Satzer P, Svec F, Sekot G, Jungbauer A. Protein adsorption onto nanoparticles induces conformational changes: Particle size dependency, kinetics, and mechanisms. Engineering in life sciences. 2016; 16:238-46.

[60] Gutjahr A, Phelip C, Coolen A L, Monge C, Boisgard A S, Paul S, et al. Biodegradable Polymeric Nanoparticles-Based Vaccine Adjuvants for Lymph Nodes Targeting. Vaccines (Basel). 2016; 4.

[61] Huntimer L, Ramer-Tait A E, Petersen L K, Ross K A, Walz K A, Wang C, et al. Evaluation of biocompatibility and administration site reactogenicity of polyanhydride-particle-based platform for vaccine delivery. Advanced healthcare materials. 2013; 2:369-78.

[62] Liu L, Yao W, Rao Y, Lu X, Gao J. pH-Responsive carriers for oral drug delivery: challenges and opportunities of current platforms. Drug Deliv. 2017; 24:569-81.

[63] Singh B, Maharjan S, Jiang T, Kang S K, Choi Y J, Cho C S. Combinatorial Approach of Antigen Delivery Using M Cell-Homing Peptide and Mucoadhesive Vehicle to Enhance the Efficacy of Oral Vaccine. Mol Pharm. 2015; 12:3816-28.

[64] Gao P, Xia G, Bao Z, Feng C, Cheng X, Kong M, et al. Chitosan based nanoparticles as protein carriers for efficient oral antigen delivery. Int J Biol Macromol. 2016; 91:716-23.

[65] Slutter B, Plapied L, Fievez V, Sande M A, des Rieux A, Schneider Y J, et al. Mechanistic study of the adjuvant effect of biodegradable nanoparticles in mucosal vaccination. J Control Release. 2009; 138:113-21.

[66] Nagarajan A G, Balasundaram S V, Janice J, Karnam G, Eswarappa S M, Chakravortty D. SopB of Salmonella enterica serovar typhimurium is a potential DNA vaccine candidate in conjugation with live attenuated bacteria. Vaccine. 2009; 27:2804-11.

[67] Berthelot-Herault F, Mompart F, Zygmunt M S, Dubray G, Duchet-Suchaux M. Antibody responses in the serum and gut of chicken lines differing in cecal carriage of Salmonella enteritidis. Vet Immunol Immunopathol. 2003; 96:43-52.

[68] Strindelius L, Degling Wikingsson L, Sjoholm I. Extracellular antigens from Salmonella enteritidis induce effective immune response in mice after oral vaccination. Infect Immun 2002; 70:1434-42.

[69] Camacho A I, Da Costa Martins R, Tamayo I, de Souza J, Lasarte J J, Mansilla C, et al. Poly(methyl vinyl ether-co-maleic anhydride) nanoparticles as innate immune system activators. Vaccine. 2011; 29:7130-5.

[70] Zhang F, Hao C, Zhang S, Li A, Zhang Q, Wu W, et al. Oral immunization with recombinant enterovirus 71 VP1 formulated with chitosan protects mice against lethal challenge. Virol J. 2014; 11:80.

[71] Dubey S, Avadhani K, Mutalik S, Sivadasan S M, Maiti B, Girisha S K, et al. *Edwardsiella tarda* OmpA Encapsulated in Chitosan Nanoparticles Shows Superior Protection over Inactivated Whole Cell Vaccine in Orally Vaccinated Fringed-Lipped Peninsula Carp (*Labeo fimbriatus*). Vaccines (Basel). 2016; 4.

[72] Okamura M, Lillehoj H S, Raybourne R B, Babu U, Heckert R. Antigen-specific lymphocyte proliferation and interleukin production in chickens immunized with killed *Salmonella enteritidis* vaccine or experimental subunit vaccines. Avian Dis. 2003; 47:1331-8.

[73] Sood S, Rishi P, Vohra H, Sharma S, Ganguly N K. Cellular immune response induced by *Salmonella enterica* serotype *typhi* iron-regulated outer-membrane proteins at peripheral and mucosal levels. J Med Microbiol. 2005; 54:815-21.

[74] Lee J S, Jung I D, Lee C M, Park J W, Chun S H, Jeong S K, et al. Outer membrane protein a of *Salmonella enterica* serovar *typhimurium* activates dendritic cells and enhances Th1 polarization. BMC Microbiol. 2010; 10:263.

[75] Shanmugasundaram R, Kogut M H, Arsenault R J, Swaggerty C L, Cole K, Reddish J M, et al. Effect of *Salmonella* infection on cecal tonsil regulatory T cell properties in chickens. Poult Sci. 2015; 94:1828-35.

[76] Burkholder K M, Thompson K L, Einstein M E, Applegate T J, Patterson J A. Influence of stressors on normal intestinal microbiota, intestinal morphology, and susceptibility to *Salmonella enteritidis* colonization in broilers. Poult Sci. 2008; 87:1734-41.

[77] Binjawadagi B, Dwivedi V, Manickam C, Ouyang K, Torrelles J B, Renukaradhya G J. An innovative approach to induce cross-protective immunity against porcine reproductive and respiratory syndrome virus in the lungs of pigs through adjuvanted nanotechnology-based vaccination. Int J Nanomedicine. 2014; 9:1519-35.

[78] Binjawadagi B, Dwivedi V, Manickam C, Ouyang K, Wu Y, Lee U, et al. Adjuvanted poly(lactic-co-glycolic) acid nanoparticle-entrapped inactivated porcine reproductive and respiratory syndrome virus vaccine elicits cross-protective immune response in pigs. Int J Nanomedicine. 2014; 9:679-94.

[79] van Ginkel F W, Nguyen H H, McGhee J R. Vaccines for mucosal immunity to combat emerging infectious diseases. Emerg Infect Dis. 2000; 6:123-32.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

We claim:

1. A composition comprising isolated *Salmonella enteritidis* outer membrane proteins (OMPs) and an isolated flagellar protein, wherein the *S. enteritidis* OMPs and the flagellar protein are entrapped in chitosan nanoparticles or polyanhydride nanoparticles.

2. The composition of claim 1, wherein the composition comprises the chitosan nanoparticles.

3. The composition of claim 1, wherein the composition comprises the polyanhydride nanoparticles.

4. The composition of claim 1, wherein the flagellar protein is also present on the surface of the nanoparticles.

5. The composition of claim 1, further comprising an adjuvant.

6. The composition of claim 1, wherein the composition is formulated for oral delivery.

7. The composition of claim 1, wherein the flagellar protein is *Salmonella enteritidis* flagellar protein.

8. A vaccine comprising the composition of claim 1 in a pharmaceutically acceptable carrier.

9. A vaccine comprising the composition of claim 7 in a pharmaceutically acceptable carrier.

10. A method of eliciting an immune response in a bird against *Salmonella enteritidis* comprising orally administering to the bird one or more doses of the vaccine of claim 9.

11. The method of claim 10, wherein the composition comprises the chitosan nanoparticles.

12. The method of claim 10, wherein the composition comprises the polyanhydride nanoparticles.

13. The method of claim 10, wherein the flagellar protein is also present on the surface of the nanoparticles.

14. The method of claim 10, wherein the composition further comprises an adjuvant.

* * * * *